(12) United States Patent
Sugimoto et al.

(10) Patent No.: US 9,079,874 B2
(45) Date of Patent: Jul. 14, 2015

(54) α-LIPOIC ACID NANOPARTICLES AND METHODS FOR PREPARING THEREOF

(75) Inventors: Kazuhisa Sugimoto, Osaka (JP); Hiromi Nishiura, Osaka (JP); Yoko Yamaguchi, Kawasaki (JP); Keiichi Hirata, Kawasaki (JP); Yoshiki Kubota, Kawasaki (JP)

(73) Assignees: Ezaki Glico Co., Ltd., Osaka (JP); Nanoegg Research Laboratories, Inc., Kanagawa (JP)

( * ) Notice: Subject to any disclaimer, the term of this patent is extended or adjusted under 35 U.S.C. 154(b) by 877 days.

(21) Appl. No.: 12/746,795

(22) PCT Filed: Dec. 12, 2008

(86) PCT No.: PCT/JP2008/072699
§ 371 (c)(1),
(2), (4) Date: Nov. 30, 2010

(87) PCT Pub. No.: WO2009/078366
PCT Pub. Date: Jun. 25, 2009

(65) Prior Publication Data
US 2011/0065781 A1  Mar. 17, 2011

(30) Foreign Application Priority Data
Dec. 14, 2007 (JP) ................................. 2007-324041

(51) Int. Cl.
*A61K 31/385* (2006.01)
*C07D 339/04* (2006.01)
*A61K 9/00* (2006.01)
*A61K 9/20* (2006.01)
*A61K 9/51* (2006.01)
*B82Y 5/00* (2011.01)
*A61K 9/14* (2006.01)

(52) U.S. Cl.
CPC ............ *C07D 339/04* (2013.01); *A61K 9/0014* (2013.01); *A61K 9/0019* (2013.01); *A61K 9/0095* (2013.01); *A61K 9/2018* (2013.01); *A61K 9/5115* (2013.01); *B82Y 5/00* (2013.01); *A61K 9/14* (2013.01)

(58) Field of Classification Search
CPC ...................................................... A61K 31/385
USPC .................................................. 514/440, 540
See application file for complete search history.

(56) References Cited

U.S. PATENT DOCUMENTS

| 2002/0044991 | A1 |  | 4/2002 | Auweter et al. |
| 2003/0054042 | A1 |  | 3/2003 | Liversidge et al. |
| 2004/0081670 | A1 |  | 4/2004 | Behnam |
| 2004/0258757 | A1 |  | 12/2004 | Bosch et al. |
| 2006/0122113 | A1 | * | 6/2006 | Pinchasi et al. ................ 514/12 |
| 2006/0193920 | A1 | * | 8/2006 | Bosch et al. .................. 424/489 |
| 2006/0287384 | A1 |  | 12/2006 | Behnam |
| 2007/0077286 | A1 | * | 4/2007 | Ishihara et al. .............. 424/449 |
| 2007/0258926 | A1 |  | 11/2007 | Yamaguchi et al. |
| 2008/0274193 | A1 | * | 11/2008 | Yamaguchi et al. ......... 424/489 |
| 2009/0131537 | A1 | * | 5/2009 | Wille, Jr. ...................... 514/725 |
| 2009/0226408 | A1 | * | 9/2009 | Kishida et al. .............. 424/94.4 |

FOREIGN PATENT DOCUMENTS

| JP | 2002-204673 A |  | 7/2002 |
| JP | 2004-161739 A |  | 6/2004 |
| JP | 2005-505568 A |  | 2/2005 |
| JP | 2005-536512 A |  | 12/2005 |
| JP | 2006-028031 |  | 2/2006 |
| JP | 2006-083147 A |  | 3/2006 |
| JP | 2006-199589 A |  | 8/2006 |
| JP | 2006-219467 |  | 8/2006 |
| JP | 2007-091686 A |  | 4/2007 |
| JP | 2007-513994 |  | 5/2007 |
| JP | 2007-302570 |  | 11/2007 |
| JP | 2008-206517 |  | 9/2008 |
| WO | 02/085328 |  | 10/2002 |
| WO | 2005/037267 A1 |  | 4/2005 |
| WO | 2005/037268 |  | 4/2005 |
| WO | 2005/060935 A1 |  | 7/2005 |
| WO | WO 2005060935 A1 | * | 7/2005 |
| WO | 2005/070413 A1 |  | 8/2005 |
| WO | WO 2005070413 A1 | * | 8/2005 |
| WO | 2005/089412 |  | 9/2005 |
| WO | WO 2006137441 A1 | * | 12/2006 |

OTHER PUBLICATIONS

Gopihath et al., "A brief review on disintegrants", Journal Chemical and Pharmaceutical Sciences, vol. 5, Jul.-Sep. 2012.
Official Action dated Aug. 23, 2013 in corresponding Japanese Application No. 2010-253310.
International Search Report and Written Opinion for corresponding International Application No. PCT/JP2008/072699 mailed Mar. 24, 2009.
Form PCT/ISA/237 for Application No. PCT/JP2008/072699 dated Mar. 24, 2009.

\* cited by examiner

*Primary Examiner* — Kendra D Carter
*Assistant Examiner* — Jason A Deck
(74) *Attorney, Agent, or Firm* — Renner, Otto, Boisselle & Sklar, LLP

(57) ABSTRACT

Provision of a stable α-lipoic acid. A method for producing α-lipoic acid nanoparticles, the method comprising the steps of: preparing an aqueous dispersion liquid containing α-lipoic acid and a nonionic surfactant; adding a divalent metal salt into the aqueous dispersion liquid, wherein the divalent metal salt is a divalent metal halide, a divalent metal acetate or a divalent metal gluconate; and adding an alkali metal carbonate or an alkali metal phosphate into the aqueous dispersion liquid which has been added with the divalent metal salt, thereby forming α-lipoic acid nanoparticles.

9 Claims, 19 Drawing Sheets

| | Control | α-Lipoic acid nanoparticle |
|---|---|---|
| At the initiation of test |  |  |
| At the completion of test |  |  |

Evaluation criteria for Mouse wrinkle

| Score | Criteria | Example |
|---|---|---|
| 1 | State in which wrinkles are absent |  |
| 2 | State in which fine wrinkles are observed overall |  |
| 3 | State in which some deep and long wrinkles are observed |  |
| 4 | State in which deep and long wrinkles are observed overall |  |

| | Before test | After 6 weeks |
|---|---|---|
| Unapplied |  |  |
| Score | 4.0 | 3.8 |
| Commercial product |  |  |
| Score | 3.8 | 3.8 |
| α-Lipoic acid nanoparticles |  |  |
| Score | 4.0 | 3.0 |

| | | Before test | After 16 weeks |
|---|---|---|---|
| Subject 1 | α-Lipoic acid nanoparticles |  |  |
| | α-Lipoic acid |  |  |
| Subject 2 | α-Lipoic acid nanoparticles |  |  |
| | Unapplied |  |  |

α-LIPOIC ACID NANOPARTICLES AND METHODS FOR PREPARING THEREOF

TECHNICAL FIELD

The present invention relates to nanoparticles comprising α-lipoic acid, and a method for producing thereof.

BACKGROUND ART

α-Lipoic acid is one kind of coenzyme which is contained in the living body and acts on the glycolytic metabolism and the cycling through the TCA cycle, and is a substance in the form of yellow crystals having the structural formula $C_8H_{14}O_2S_2$, the molecular weight of 206.3, and the melting point of 60 to 62° C. α-Lipoic acid is also present in the human body, and is contained in many foods such as broccoli and red meat. Therefore, α-lipoic acid can be said to be a highly safe substance. In terms of function, α-lipoic acid is recognized as having strong antioxidant capacity in the living body thereby reducing oxidative stress, and as a chelating agent that is effective in the discharge of heavy metals. α-Lipoic acid is currently formulated into pharmaceutical products as "thioctic acid," and thioctic acid preparations are usually sold as injections. As the efficacy and effect of the thioctic acid preparations, supplementation upon an increase in the demand of thioctic acid (at the time of vigorous physical labor), Leigh syndrome (subacute necrotic encephalomyelitis), and toxic (due to streptomycin or kanamycin) and noise-induced (occupational) inner ear hearing impairment are described in Drugs in Japan, Ethical Drugs (Non-Patent Document 1).

α-Lipoic acid had been approved for use in foods and cosmetics as a result of recent relaxation of regulations, and therefore, further applications thereof in these fields are expected.

α-Lipoic acid is in the form of a yellow powder, but since it is hardly soluble in water, its uses are limited. Furthermore, α-lipoic acid is very unstable to heat and light, and is difficult to be present stably in the preparation. Furthermore, it is a problem of α-lipoic acid that it has a characteristic sulfurous odor, and the odor becomes stronger when α-lipoic acid is degenerated and that it becomes gummy by heat. Thus, when α-lipoic acid is used in foods, cosmetics and pharmaceutical products, there is a serious problem in terms of the product quality and after-use feel.

In order to solve such problems as described above, Patent Document 1 suggests a water-soluble preparation containing α-lipoic acid or a pharmacologically acceptable salt thereof, and a sulfite or a hydrate thereof.

Patent Document 2 suggests a method for preparing a water-soluble preparation by dissolving α-lipoic acid in an organic solvent such as ethanol, subsequently adding an emulsifying agent and a polyhydric alcohol thereto, and bringing α-lipoic acid to an emulsified state by the physical action of an emulsifying machine or the like.

Furthermore, Patent Document 3 and Patent Document 4 suggest methods for preparing a water-soluble α-lipoic acid preparation, which methods enhance dispersibility in water and emulsification stability by mixing α-lipoic acid with an organic solvent such as ethanol, an emulsifying agent or a polyhydric alcohol.

However, the methods of bringing an emulsified state as described in these patent documents require a special apparatus called emulsifying machine, and when the particle size of the emulsification liquid is large, and when the distribution of the size of particle diameter is non-uniform, the emulsified state becomes easily separable. Furthermore, in other methods, it has been pointed out that since the dispersion of α-lipoic acid by emulsification is incomplete, the sulfurous odor characteristic to α-lipoic acid is strongly generated during storage.

Meanwhile, there are documents related to nanoparticle formation from retinoic acid. Patent Documents 5 to 8 disclose polyvalent metal inorganic salt-coated retinoic acid nanoparticles.

However, since retinoic acid is completely different from α-lipoic acid in structure, it would not be easily conceivable and had never been believed that α-lipoic acid is used instead of the retinoic acid of Patent Documents 5 to 8.

More detailed description will be given in this regard. First, as can be seen from the structures shown below, α-lipoic acid and retinoic acid have completely different structures except that they both contain one carboxyl group. Furthermore, α-lipoic acid is also completely different from retinoic acid in that α-lipoic acid contains sulfur atoms in the molecule and does not have any double bond. From the points as discussed above, it would not be easily conceivable to use α-lipoic acid instead of retinoic acid in the methods described in Patent Documents 5 to 8.

[Chem. 1] α-Lipoic Acid
Retinoic Acid

Secondly, retinoic acid is said to be an important in vivo hormone, which is, in the living body, involved with the growth and differentiation of cells, maintenance of homeostasis of the living body, morphogenesis, and the expression control of various genes by means of the binding to intranuclear retinoic acid receptors is proposed as a mechanism of action. On the other hand, as a coenzyme of the glycolytic system, α-lipoic acid catalyzes the oxidative decarbonation reaction from pyruvic acid to acetyl CoA, and thus is said to be an indispensable nutrient for cellular respiration and energy production. Furthermore, as a well-known function of α-lipoic acid, an antioxidant action is known. From the points as discussed above, retinoic acid and α-lipoic acid are completely different in terms of the functions in the living body and the expected pharmacological effects, and therefore, even from the viewpoint of the effectiveness demanded when its industrial application is believed, it would not be easily conceivable to use α-lipoic acid as a substitute for retinoic acid in the methods described in the Patent Documents 5 to 8.

Thirdly, it is reported in p. 410 of Non-Patent Document 2 that the pKa value of retinoic acid is 6.4, and it is described in the Discussion section on p. 411 that the pKa increases to 7 to 8 as retinoic acid forms micelles. On the other hand, Non-Patent Document 3 describes that the pKa value of α-lipoic acid is 4.76. From the points as described above, α-lipoic acid and retinoic acid are completely different in the properties related to dissociation. Therefore, it would not be easily conceivable to use α-lipoic acid as a substitute for retinoic acid in the methods described in Patent Documents 5 to 8.

Patent Document 1: Japanese Laid-open Patent Publication No. 2005-2096
Patent Document 2: Japanese Laid-open Patent Publication No. 2006-129841
Patent Document 3: Japanese Laid-open Patent Publication No. 2006-257010
Patent Document 4: Japanese Laid-open Patent Publication No. 2007-16000
Patent Document 5: Japanese Laid-open Patent Publication No. 2004-161739
Patent Document 6: International Publication No. 2005/037267 pamphlet Patent Document 7: International Publication No. 2005/037268 pamphlet Patent Document 8: International Publication No. 2005/070413 pamphlet Non-Patent Document 1: Drugs in Japan, Ethical Drugs, Edition of 2007, Jiho, Inc., p. 1327 (2006)

Non-Patent Document 2: Robbert Creton, et al., Int. J. Dev. Biol., 39:409-414 (1995)

Non-Patent Document 3: Lester J. Reed, et al., JOURNAL OF THE AMERICAN CHEMICAL SOCIETY, Vol. 75:1267 (1953)

DISCLOSURE OF THE INVENTION

Problems to be Solved by the Invention

The present invention is intended to solve the problems described above, and it is an object of the invention to provide stable α-lipoic acid.

Means to Solve the Problems

The inventors of the present invention conducted intensive studies in order to solve the problems as described above, and as a result, they found that when a nonionic surfactant, a divalent metal ion, and a carbonate ion or a phosphate ion are used in a specific order, stable α-lipoic acid nanoparticles can be obtained. Thus, the inventors completed the present invention based on this finding.

The present invention utilizes the amphiphilicity of α-lipoic acid. α-Lipoic acid is hardly soluble in water under acidic conditions or neutral conditions, but if an alkali is added, the mixture becomes a transparent liquid. The α-lipoic acid in an alkali solution is believed to form spherical micelles in water. It is believed that if a nonionic surfactant is subsequently added to the α-lipoic acid, mixed micelles of α-lipoic acid and the nonionic surfactant are formed. Furthermore, it is believed that when divalent metal cations are allowed to bind to the negative charges of the lipoic acid ions by further adding a halide, acetate or gluconate of the divalent metal to the mixed micelles, and thereby preventing aggregation and precipitation of α-lipoic acid, spherical- or oval-shaped micelles in which the divalent metal ions are bound to the surface of the lipoic acid, are formed. Furthermore, divalent anions are added thereto, and the divalent anions are allowed to adsorb (bind) to the metal ions at the micelle surface, thereby neutralizing the charge at the micelle surface. As a result, it is believed that a coating of a polyvalent metal inorganic salt is formed at the micelle surface, and thus, α-lipoic acid nanoparticles coated with the polyvalent metal inorganic salt are prepared. Since this production method of nanoparticles uses α-lipoic acid micelles as a template, the encapsulation ratio corresponds to the concentration excluding monodisperse α-lipoic acid molecules, and thus, is thought to be close to 100%. It is thought that the hydrophilic group of the nonionic surfactant is exposed at the surface of the subject nanoparticles. The nanoparticles of the present invention are dispersed transparently in water. Also, although the crystals of the polyvalent metal inorganic salt such as $CaCO_3$ do not dissolve in water, the crystals are believed to adopt a vaterite or amorphous structure at the nanoparticle surface, which dissolves slowly in the living body, and thus a DDS effect of sustained release of α-lipoic acid is expected.

The inventors of the present invention also found that α-lipoic acid is solubilized in a certain type of nonionic surfactant, and that by dispersing this solubilized product in water, mixed micelles of α-lipoic acid and the nonionic surfactant are formed. By adding a halide, acetate or gluconate of a divalent metal to these mixed micelles of the α-lipoic acid-dissolved nonionic surfactant, a divalent metal cation is allowed to bind to the negative charge of the α-lipoic acid ion. It is believed that, during this, the presence of the surfactant prevents aggregation and precipitation of α-lipoic acid, and that thereby, spherical- or oval-shaped micelles having the divalent metal ion bound to the surface of the lipoic acid are formed. A divalent anion (an alkali metal carbonate or alkali metal phosphate) is further added to these micelles, and the divalent anion is allow to adsorb (bind) to the metal ion at the micelle surface to thereby neutralize the charge of the micelle surface. Thus, it is thought that as a result, a coating of a polyvalent metal inorganic salt is formed at the micelle surface, and polyvalent metal inorganic salt-coated α-lipoic acid nanoparticles are prepared.

In order to achieve the objects described above, the present invention provides, for example, the following means:

(Item 1) A method for producing α-lipoic acid nanoparticles, the method comprising the steps of:

preparing an aqueous dispersion liquid containing α-lipoic acid and a nonionic surfactant;

adding a divalent metal salt into the aqueous dispersion liquid, wherein the divalent metal salt is a divalent metal halide, a divalent metal acetate or a divalent metal gluconate; and adding an alkali metal carbonate or an alkali metal phosphate into the aqueous dispersion liquid wherein the divalent metal salt has been added, thereby forming α-lipoic acid nanoparticles.

(Item 2) The method according to Item 1, wherein the step of preparing an aqueous dispersion liquid containing α-lipoic acid and a nonionic surfactant, comprises: dissolving α-lipoic acid in the nonionic surfactant which is in a liquid form, to obtain a surfactant solution; and adding water or a liquid containing water to the surfactant solution to obtain the aqueous dispersion liquid.

(Item 3) The method according to Item 1, wherein the step of preparing an aqueous dispersion liquid containing α-lipoic acid and a nonionic surfactant, comprises: producing a mixture of α-lipoic acid, an alkaline substance and water to prepare an α-lipoic acid-containing aqueous dispersion liquid; and adding the nonionic surfactant into the α-lipoic acid-containing aqueous dispersion liquid.

(Item 4) The method according to any one of Items 1 to 3, wherein the divalent metal salt is selected from the group consisting of calcium chloride, calcium bromide, calcium fluoride, calcium iodide, magnesium chloride, magnesium bromide, magnesium fluoride, magnesium iodide, zinc chloride, zinc bromide, zinc fluoride, zinc iodide, calcium acetate, magnesium acetate, zinc acetate, calcium gluconate, magnesium gluconate and zinc gluconate.

(Item 5) The method according to any one of Items 1 to 4, wherein the divalent metal salt is selected from the group consisting of calcium chloride, magnesium chloride and zinc gluconate.

(Item 6) The method according to any one of Items 1 to 5, wherein the alkali metal carbonate or alkali metal phosphate is selected from the group consisting of sodium carbonate, potassium carbonate, sodium hydrogen carbonate, potassium hydrogen carbonate, sodium phosphate and potassium phosphate.

(Item 7) The method according to any one of Items 1 to 6, wherein the alkali metal carbonate or alkali metal phosphate is selected from the group consisting of sodium carbonate and disodium hydrogen phosphate.

(Item 8) The method according to any one of Items 1 to 7, wherein the nonionic surfactant is selected from the group consisting of polyoxyethylene hydrogenated castor oils, polyoxyethylene alkyl ethers, polyoxyethylene sorbitan fatty acid esters, polyoxyethylene polyoxypropylene alkyl ethers, sucrose fatty acid esters and polyglycerin fatty acid esters.

(Item 9) The method according to Item 8, wherein the HLB value of the nonionic surfactant is 10 or more.

(Item 10) The method according to any one of Items 1 to 9, wherein the nonionic surfactant is selected from the group consisting of polyoxyethylene (degree of polymerization 10 to 20) octyldodecylether, polyoxyethylene (degree of polymerization 10 to 20) stearyl ether, polyoxyethylene (degree of polymerization 10 to 20) polyoxypropylene (degree of polymerization 4 to 8) cetyl ether, polyoxyethylene (degree of polymerization 20 to 100) hydrogenated castor oil, and sucrose lauric acid ester.

(Item 11) The method according to any one of Items 2 and 4-10, wherein in the step of preparing an aqueous dispersion liquid containing α-lipoic acid and a nonionic surfactant, polyethylene glycol is mixed into the nonionic surfactant, prior to the dissolving of α-lipoic acid in the nonionic surfactant; or water containing polyethylene glycol is used as the liquid containing water, in the step of adding a liquid containing water to the surfactant solution.

(Item 12) α-Lipoic acid nanoparticles comprising α-lipoic acid, a nonionic surfactant, a divalent metal ion, and a carbonate ion or a phosphate ion.

(Item 13) The α-lipoic acid nanoparticles according to Item 12, wherein the divalent metal ion is a calcium ion, a zinc ion or a magnesium ion.

(Item 14) The α-lipoic acid nanoparticles according to Item 12 or 13, wherein the nonionic surfactant is selected from the group consisting of polyoxyethylene hydrogenated castor oils, polyoxyethylene alkyl ethers, polyoxyethylene sorbitan fatty acid esters, polyoxyethylene polyoxypropylene alkyl ethers, sucrose fatty acid esters and polyglycerin fatty acid esters.

(Item 15) The α-lipoic acid nanoparticles according to any one of Items 12 to 14, further comprising polyethylene glycol.

(Item 16) An external preparation for skin, comprising the α-lipoic acid nanoparticles according to any one of Items 12 to 15.

(Item 17) A pharmaceutical product comprising the α-lipoic acid nanoparticles according to any one of Items 12 to 15.

(Item 18) A composition for oral cavity, comprising the α-lipoic acid nanoparticles according to any one of Items 12 to 15.

(Item 19) A food comprising the α-lipoic acid nanoparticles according to any one of Items 12 to 15.

The present invention also provides, for example, the following means:

(Item A1) A method for producing α-lipoic acid nanoparticles, the method comprising the steps of:

producing a mixture of α-lipoic acid, an alkaline substance and water to prepare an α-lipoic acid-containing aqueous dispersion liquid;

adding the nonionic surfactant into the aqueous dispersion liquid;

adding a divalent metal salt into the aqueous dispersion liquid wherein the nonionic surfactant has been added, wherein the divalent metal salt is a divalent metal halide, a divalent metal acetate or a divalent metal gluconate; and adding an alkali metal carbonate or an alkali metal phosphate into the aqueous dispersion liquid wherein the divalent metal salt has been added, thereby forming α-lipoic acid nanoparticles.

(Item A2) The method according to Item A1, wherein the divalent metal salt is selected from the group consisting of calcium chloride, calcium bromide, calcium fluoride, calcium iodide, magnesium chloride, magnesium bromide, magnesium fluoride, magnesium iodide, zinc chloride, zinc bromide, zinc fluoride, zinc iodide, calcium acetate, magnesium acetate, zinc acetate, calcium gluconate, magnesium gluconate and zinc gluconate.

(Item A3) The method according to Item A1, wherein the divalent metal salt is selected from the group consisting of calcium chloride, magnesium chloride and zinc gluconate.

(Item A4) The method according to Item A1, wherein the alkali metal carbonate or alkali metal phosphate is selected from the group consisting of sodium carbonate, potassium carbonate, sodium hydrogen carbonate, potassium hydrogen carbonate, sodium phosphate and potassium phosphate.

(Item A5) The method according to Item A1, wherein the alkali metal carbonate or alkali metal phosphate is selected from the group consisting of sodium carbonate and disodium hydrogen phosphate.

(Item A6) The method according to Item A1, wherein the nonionic surfactant is selected from the group consisting of polyoxyethylene hydrogenated castor oils, polyoxyethylene alkyl ethers, polyoxyethylene sorbitan fatty acid esters, polyoxyethylene polyoxypropylene alkyl ethers, sucrose fatty acid esters and polyglycerin fatty acid esters.

(Item A7) The method according to Item A6, wherein the HLB value of the nonionic surfactant is 10 or more.

(Item A8) The method according to Item A1, wherein the nonionic surfactant is selected from the group consisting of polyoxyethylene (degree of polymerization 10 to 20) octyl dodecyl ether, polyoxyethylene (degree of polymerization 10 to 20) stearyl ether, polyoxyethylene (degree of polymerization 10 to 20) polyoxypropylene (degree of polymerization 4 to 8) cetyl ether, polyoxyethylene (degree of polymerization 20 to 100) hydrogenated castor oil, and sucrose lauric acid ester.

(Item A9) α-Lipoic acid nanoparticles comprising α-lipoic acid, a nonionic surfactant, a divalent metal ion, and a carbonate ion or a phosphate ion.

(Item A10) The α-lipoic acid nanoparticles according to Item A9, wherein the divalent metal ion is a calcium ion, a zinc ion or a magnesium ion.

(Item A11) The α-lipoic acid nanoparticles according to Item A9, wherein the nonionic surfactant is selected from the group consisting of polyoxyethylene hydrogenated castor oils, polyoxyethylene alkyl ethers, polyoxyethylene sorbitan fatty acid esters, polyoxyethylene polyoxypropylene alkyl ethers, sucrose fatty acid esters and polyglycerin fatty acid esters.

(Item A12) An external preparation for skin, comprising the α-lipoic acid nanoparticles according to Item A9.

(Item A13) A pharmaceutical product comprising the α-lipoic acid nanoparticles according to Item A9.

(Item A14) A composition for oral cavity, comprising the α-lipoic acid nanoparticles according to Item A9.

(Item A15) A food comprising the α-lipoic acid nanoparticles according to Item A9.

Effect of the Invention

The method for preparing nanoparticles of the present invention uses α-lipoic acid micelles as templates, and thus the encapsulation ratio corresponds to the concentration excluding monodisperse α-lipoic acid molecules, thereby being close to 100%. It is believed that at the surface of the nanoparticles of the present invention, the hydrophilic group of the nonionic surfactant is exposed, and thus the nanoparticles are dispersed transparently in water. Furthermore, at the surface of the nanoparticles, a polyvalent metal inorganic salt is believed to adopt a vaterite or amorphous structure, which dissolves slowly in the living body, and thus a DDS effect of sustained release of α-lipoic acid is expected. Furthermore, since the nanoparticles of the present invention are coated with a polyvalent metal inorganic salt at the surface, generation of the sulfurous odor characteristic to α-lipoic acid can be significantly suppressed.

BEST MODE FOR CARRYING OUT THE INVENTION

Figure 1:
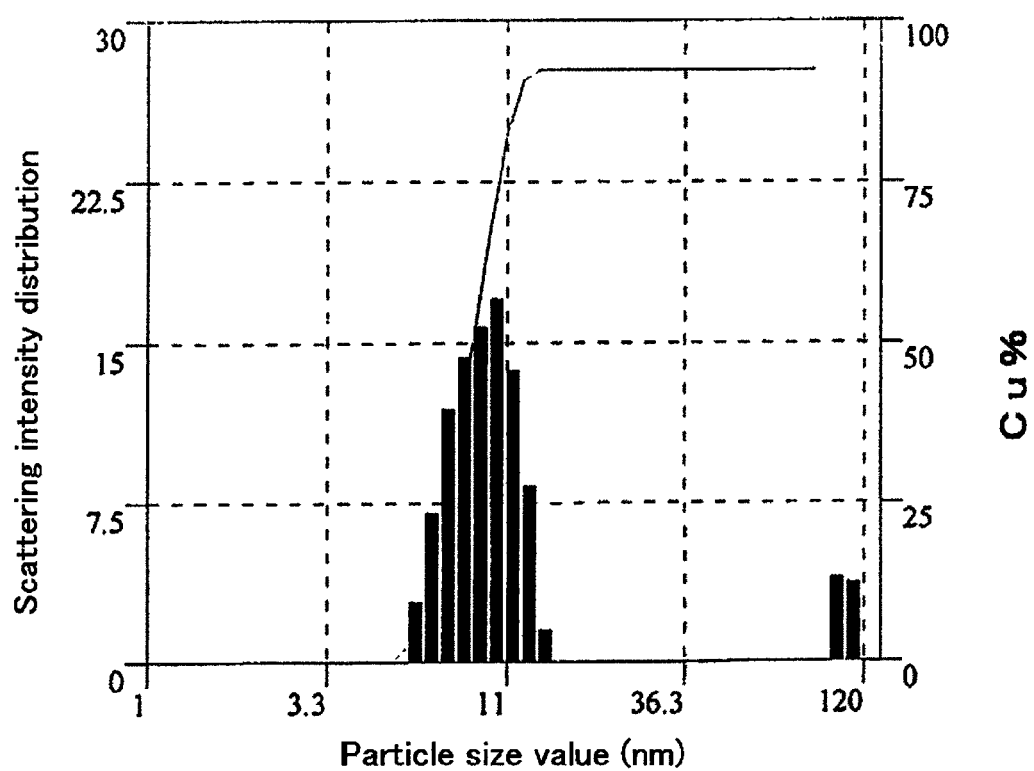
FIG. 1 shows the result of the particle size distribution of the α-lipoic acid-$MgCO_3$ nanoparticles produced by using distilled water in Example 1, as measured by using a light scattering photometer (Otsuka Electronics Co., Ltd., ELS-710TY).

Hereinafter, the present invention will be described in detail.

(1. Material for α-Lipoic Acid Nanoparticles)

The α-lipoic acid nanoparticles of the present invention are produced using α-lipoic acid, a nonionic surfactant, a divalent metal salt, and an alkali metal carbonate or alkali metal phosphate. Those ordinarily skilled in the art can use other materials as necessary, such as an alkaline aqueous solution, in the production method of the present invention.

(1a. α-Lipoic Acid)

α-Lipoic acid that is used in the present invention may be any α-lipoic acid that is known in the art. The α-lipoic acid is also known as thioctic acid. The α-lipoic acid may be any of R,S-(+/−)-α-lipoic acid, R-(+)-α-lipoic acid, and S-(−)-α-lipoic acid. The α-lipoic acid may be in the form of an acid or may be in the form of a salt. Any commercially available α-lipoic acid may be used. The α-lipoic acid can be in the form of a powder or crystals.

(1b. Nonionic Surfactant)

The nonionic surfactant that is used in the present invention may be any surfactant as long as it is nonionic. Examples of the nonionic surfactant used in the present invention include, but are not particularly limited to, polyoxyethylene hydrogenated castor oils, polyoxyethylene alkyl ethers, polyoxyethylene sorbitan fatty acid esters, polyoxyethylene polyoxypropylene alkyl ethers, polyglycerin fatty acid esters, sucrose fatty acid esters, propylene glycol fatty acid esters, monoglycerin fatty acid esters, diglycerin fatty acid esters, sorbitan fatty acid esters, polyoxyethylene fatty acid esters, and the like. As for the nonionic surfactant used in the present inventions, those having an HLB value of about 10 or more are particularly preferable. As for the nonionic surfactant used in the present inventions, a nonionic surfactant which is selected from the group consisting of polyoxyethylene hydrogenated castor oil, polyoxyethylene alkyl ethers, polyoxyethylene sorbitan fatty acid esters, polyoxyethylene polyoxypropylene alkyl ethers, sucrose fatty acid esters and polyglycerin fatty acid esters, and which has an HLB value of about 10 or more, is particularly preferable. According to the present invention, it is more particularly preferable that the nonionic surfactant be selected from the group consisting of polyoxyethylene (degree of polymerization 10 to 20) octyl dodecyl ether, polyoxyethylene (degree of polymerization 10 to 20) stearyl ether, polyoxyethylene (degree of polymerization 10 to 20) polyoxypropylene (degree of polymerization 4 to 8) cetyl ether, polyoxyethylene (degree of polymerization 20 to 100) hydrogenated castor oil and sucrose lauric acid ester. In the present inventions, one kind of nonionic surfactant may be used, or two or more kinds of nonionic surfactant may be used in combination. The HLB value of the polyoxyethylene sorbitan fatty acid ester is preferably about 10 or more, more preferably about 12 or more, and most preferably about 14 or more. The HLB value of the polyoxyethylene sorbitan fatty acid ester is preferably about 20 or less, more preferably about 18 or less, and most preferably about 16 or less.

The nonionic surfactant may be those which are solid at room temperature (that is, a surfactant having a melting point which is higher than room temperature), or may be those which are liquid at room temperature (that is, a surfactant having a melting point which is lower than room temperature). The term "nonionic surfactant in a liquid form" is used in the present specification in relation to both the embodiment of using a nonionic surfactant which is a liquid at room temperature and the embodiment of using a nonionic surfactant which is a solid at room temperature, in a liquid form by heating to melt.

As used in the present specification, the "HLB value" refers to the Hydrophile Lipophile Balance value, and is generally calculated by $20 \times M_H/M$, wherein $M_H$ is the molecular weight of the hydrophilic group moiety, and M is the molecular weight of the whole molecule. The HLB value is 0 when the amount of hydrophilic groups in the molecule is 0%, and is 20 when the amount of hydrophilic groups is 100%. The HLB value indicates, in connection with the surfactant, the size and strength of the hydrophilic and hydrophobic groups that form the surfactant molecule, so that a surfactant having high hydrophobicity has a small HLB value, and a surfactant having high hydrophilicity has a large HLB value.

Examples of the polyoxyethylene hydrogenated castor oils that are preferably used in the present invention includes polyoxyethylene hydrogenated castor oils having any degree of polymerization of ethylene oxide. For example, polyoxyethylene hydrogenated castor oils having the degree of polymerization of ethylene oxide of about 10 or more are preferred, and polyoxyethylene hydrogenated castor oils having the degree of polymerization of ethylene oxide of about 200 or less are preferred. Examples of even more preferable polyoxyethylene hydrogenated castor oils include polyoxyethylene hydrogenated castor oil 40, polyoxyethylene hydrogenated castor oil 60, and polyoxyethylene hydrogenated castor oil 80. Note that these numbers indicate the extent of the degree of polymerization of ethylene oxide, and for example, polyoxyethylene hydrogenated castor oil 40 indicates that the number of added moles of ethylene oxide is 40.

Examples of the polyoxyethylene alkyl ethers that are preferably used in the present invention include polyoxyethylene alkyl ethers having any degree of polymerization of ethylene oxide. Polyoxyethylene alkyl ethers having the degree of polymerization of ethylene oxide of about 10 or more are preferred, and polyoxyethylene alkyl ethers having the degree of polymerization of ethylene oxide of about 20 or less are preferred. Examples of even more preferable polyoxyethylene alkyl ethers include, for example, polyoxyethylene (20) stearyl ether (also described as POE (20) stearyl ether), polyoxyethylene (20) octyl dodecyl ether (also described as POE (20) octyl dodecyl ether) and polyoxyethylene (20) isostearyl ether (POE (20) isostearyl ether). This number of (20) indicates that the degree of polymerization of ethylene oxide is 20.

Examples of the polyoxyethylene sorbitan fatty acid esters that are preferably used in the present invention include polyoxyethylene sorbitan fatty acid esters having any degree of polymerization of ethylene oxide. Polyoxyethylene sorbitan fatty acid esters having the degree of polymerization of ethylene oxide of about 10 or more are preferred, and polyoxyethylene sorbitan fatty acid esters having the degree of polymerization of ethylene oxide of about 20 or less are preferred. Examples of even more preferable polyoxyethylene sorbitan fatty acid esters include, for example, polyoxyethylene (20) sorbitan monooleate (also described as POE (20) sorbitan monooleate), polyoxyethylene (20) sorbitan monolaurate (also described as POE (20) sorbitan monolaurate), polyoxyethylene (20) sorbitan monostearate (also described as POE (20) sorbitan monostearate), polyoxyethylene (20) sorbitan monopalmitate (also described as POE (20) sorbitan monopalmitate), and polyoxyethylene (20) sorbitan trioleate (also described as POE (20) sorbitantrioleate). This number of (20) indicates that the degree of polymerization of ethylene oxide is 20.

Examples of the polyoxyethylene polyoxypropylene alkyl ethers that are preferably used in the present invention include polyoxyethylene polyoxypropylene ethers having any degree of polymerization of ethylene oxide. Polyoxyethylene polyoxypropylene alkyl ethers having the degree of polymerization of the polyoxyethylene moiety of about 10 or more are preferred, and polyoxyethylene polyoxypropylene alkyl ethers having the degree of polymerization of the polyoxyethylene moiety of about 20 or less are preferred. Polyoxyethylene polyoxypropylene alkyl ethers having the degree of polymerization of the polyoxypropylene moiety of about 4 or more are preferred, and polyoxyethylene polyoxypropylene alkyl ethers having the degree of polymerization of the polyoxypropylene moiety of about 8 or less are preferred. Examples of the even more preferable polyoxyethylene polyoxypropylene alkyl ether include, for example, polyoxyethylene (20) polyoxypropylene (8) cetyl ether (also described as POE (20) POP (8) cetyl ether), polyoxyethylene (20) polyoxypropylene (4) cetyl ether (also described as POE (20) POP (4) cetyl ether), polyoxyethylene (34) polyoxypropylene (23) cetyl ether (also described as POE (34) POP (23) cetyl ether), polyoxyethylene polyoxyethylene propylene decyl tetradecyl ether (also described as POEPOE propylene decyl tetradecyl ether), and polyoxyethylene (20) isostearyl ether (also described as POE (20) isostearyl ether).

Examples of the polyglycerin fatty acid esters that are preferably used in the present invention include, for example, decaglycerin monolaurate, decaglycerin monomyristate, decaglycerin monooleate and decaglycerin monostearate. The HLB value of the polyglycerin fatty acid ester used is not particularly limited, but the HLB value is preferably about 8 or more, more preferably about 10 or more, and even more preferably about 12 or more. The HLB value is preferably about 20 or less, more preferably about 19 or less, and even more preferably about 18 or less.

Examples of the sucrose fatty acid esters that are preferably used in the present invention include, for example, sucrose stearic acid ester, sucrose palmitic acid ester, sucrose myristic acid ester and sucrose lauric acid ester. Among them, sucrose lauric acid ester is more preferably used.

In the present inventions, the content of the surfactant in the α-lipoic acid nanoparticles varies with the kinds of surfactant. The amount of the surfactant is preferably about one-fold or more, more preferably about 2-fold or more, even more preferably about 3-fold or more, particularly preferably about 4-fold or more, and most preferably about 5-fold or more, of the weight of α-lipoic acid. The amount of the surfactant is preferably about 40-fold or less, more preferably about 35-fold or less, even more preferably about 30-fold or less, particularly preferably about 25-fold or less, and most preferably about 20-fold or less, of the weight of α-lipoic acid. If the amount of the surfactant relative to the amount of α-lipoic acid is too small, the nanoparticles may become prone to aggregate, and it may become difficult to obtain transparent and stable particles. If the amount of surfactant relative to the amount of α-lipoic acid is too large, even if the amount of addition is increased, the effect obtainable thereby does not significantly increase, and there may occur problems such as that the α-lipoic acid content is relatively decreased, the handling at the time of use becomes poor, and when the subject nanoparticles are used in foods, the taste derived from the surfactant is manifested, thereby lowering the product value.

(1c. Divalent Metal Salt)

In the present inventions, a divalent metal salt is used. Examples of the divalent metal salt that can be used include divalent metal halides, divalent metal acetates and divalent metal gluconates.

The divalent metal acetate is a salt formed of acetic acid and a divalent metal, and is also referred to as acetic acid divalent metal salt. The divalent metal gluconate is a salt formed of gluconic acid and a divalent metal, and is also referred to as gluconic acid divalent metal salt. The divalent metal salt is preferably selected from the group consisting of calcium chloride, calcium bromide, calcium fluoride, calcium iodide, magnesium chloride, magnesium bromide, magnesium fluoride, magnesium iodide, zinc chloride, zinc bromide, zinc fluoride, zinc iodide, calcium acetate, magnesium acetate, zinc acetate, calcium gluconate, magnesium gluconate and zinc gluconate, and is more preferably selected from the group consisting of magnesium chloride, calcium chloride and zinc gluconate. Commercially available divalent metal salts can be used. One kind of divalent metal salt may be used, or two or more kinds of divalent metal salts may be used in mixture. It is preferable to use one kind of divalent metal salt.

(1d. Alkali Metal Carbonate or Alkali Metal Phosphate)

In the present inventions, an alkali metal carbonate or an alkali metal phosphate is used. Examples of the alkali metal in the alkali metal carbonate or alkali metal phosphate include sodium, potassium, lithium, rubidium, cesium and francium. The alkali metal is preferably sodium or potassium, and is more preferably sodium. Examples of the alkali metal carbonate that can be used in the present inventions include, for example, sodium carbonate, potassium carbonate, sodium hydrogen carbonate and potassium hydrogen carbonate, and sodium carbonate is preferred. Examples of the alkali metal phosphate that can be used in the present inventions include, for example, sodium phosphate and potassium phosphate. The sodium phosphate may be sodium metaphosphate, disodium hydrogen phosphate, sodium dihydrogen phosphate, trisodium phosphate, sodium pyrophosphate or sodium hydrogen pyrophosphate, and is preferably disodium hydrogen phosphate. The potassium phosphate may be potassium dihydrogen phosphate, dipotassium hydrogen phosphate or tripotassium phosphate, and is preferably dipotassium hydrogen phosphate.

Commercially available alkali metal carbonates and alkali metal phosphates can be used. One kind of alkali metal carbonate or alkali metal phosphate may be used, and two or more kinds of alkali metal carbonate or alkali metal phosphate may be used in mixture. It is preferable to use one kind of alkali metal carbonate or alkali metal phosphate.

(1e. Additive)

In the present inventions, an additive can be used. The additive is preferably a water-soluble polymer. Examples of the additive include polyethylene glycol, Plant-derived macromolecules, microorganism-derived macromolecules, animal-derived macromolecules, starches and dextrins, celluloses, vinylic-type macromolecules and acrylic-type macromolecules.

It is believed that by using the additive, a micelle aggregation suppressive effect and dispersive effect by adsorbing the water-soluble polymer to the micelle surface; a micelle aggregation suppressive effect by steric hindrance caused by the presence of polymer compounds in the water (continuous phase) between micelles; and a micelle aggregation suppressive effect by viscosity increase, and the like may be obtained.

Polyethylene glycol is a substance represented by $HO(CH_2CH_2O)_nH$. Polyethylene glycol is a polyether having a structure which is believed to be produced by dehydration polycondensation of ethylene glycol, and having hydroxyl groups at both ends. Various polyethylene glycols having a molecular weight of about 200 to about 20,000 are known. Polyethylene glycol is liquid when the molecular weight is about 200 to about 600, and is solid when the molecular weight exceeds about 1000. Since polyethylene glycol is a polymer, it is usually marketed as mixtures of molecules having various molecular weights. The number average molecular weight of polyethylene glycol is preferably about 500 or more, more preferably about 600 or more, even more preferably about 700 or more, still more preferably about 800 or more, particularly preferably about 900 or more, and most preferably about 1,000 or more. The number average molecular weight of polyethylene glycol is preferably about 10,000 or less, more preferably about 9,000 or less, even more preferably about 8,000 or less, still more preferably about 7,000 or less, particularly preferably about 6,500 or less, and most preferably about 20,000 or less. Examples of polyethylene glycol that is preferably used in the present inventions include polyethylene glycol 1000, polyethylene glycol 4000, and polyethylene glycol 6000.

Plant-derived macromolecules refer to macromolecules extracted or purified from plants. Examples of the plant-derived macromolecules include gum arabic, tragacanth gum, galactan, guar gum, locust bean gum, carrageenan, pectin, quince seed (*Cyclonia oblonga* seed) extract, brown alga powder, and the like.

Microorganism-derived macromolecules refer to macromolecules extracted or purified from microorganisms. Examples of the microorganism-derived macromolecules include xanthan gum, dextran, pullulan and the like.

Animal-derived macromolecules refer to macromolecules extracted or purified from animals. Examples of the animal-derived macromolecules include collagen, casein, albumin, gelatin, hyaluronic acid, and the like.

Starches and dextrins refer to starch and dextrin, as well as chemical modification products, enzymatic treatment products and physical treatment products thereof. The starches are preferably chemically modified starches. Examples of the starches include carboxymethyl starch, methylhydroxy starch, and the like.

Celluloses refer to celluloses, and chemical modification products, enzymatic treatment products and physical treatment products thereof. Examples of the celluloses include methylcellulose, nitrocellulose, ethylcellulose, methylhydroxypropylcellulose, hydroxyethylcellulose, cellulose sulfate, hydroxypropylcellulose, carboxymethylcellulose, crystalline cellulose, cellulose powders, and the like.

Vinylic-type macromolecules refer to macromolecules obtained by polymerizing vinyl monomers. Examples of the vinylic-type macromolecules include polyvinyl alcohol, polyvinyl methyl ether, polyvinylpyrrolidone, carboxyvinyl polymers, and the like.

Acrylic-type macromolecules refer to macromolecules obtained by polymerizing acrylic monomers. Examples of the acrylic-type macromolecules include polyacrylic acid and salts thereof, polyacrylimide, and the like.

(2. Method for Producing α-Lipoic Acid Nanoparticles)

The method for producing α-lipoic acid nanoparticles of the present invention comprises the steps of: preparing an aqueous dispersion liquid containing α-lipoic acid and a nonionic surfactant; adding a divalent metal salt into the aqueous dispersion liquid, wherein the divalent metal salt is a divalent metal halide, a divalent metal acetate or a divalent metal gluconate; and adding an alkali metal carbonate or an alkali metal phosphate into the aqueous dispersion liquid wherein the divalent metal salt has been added, thereby forming α-lipoic acid nanoparticles.

In a preferred embodiment, the step of preparing an aqueous dispersion liquid containing α-lipoic acid and a nonionic surfactant, comprises: dissolving α-lipoic acid in the nonionic surfactant which is in a liquid form, to obtain a surfactant solution; and adding water or a liquid containing water to the surfactant solution to obtain the aqueous dispersion liquid. In this embodiment, α-lipoic acid nanoparticles can be produced by carrying out steps including "2a-1", "2b-1", "2c" and "2d" described below.

In another preferred embodiment, the step of preparing an aqueous dispersion liquid containing α-lipoic acid and a nonionic surfactant, comprises: producing a mixture of α-lipoic acid, an alkaline substance and water to prepare an α-lipoic acid-containing aqueous dispersion liquid; and adding the nonionic surfactant into the α-lipoic acid-containing aqueous dispersion liquid. In this embodiment, α-lipoic acid nanoparticles can be produced by carrying out steps including "2a-2", "2b-2", "2c" and "2d" described below.

In a specific preferred embodiment, the method of the present invention is a method for producing α-lipoic acid nanoparticles and comprise the steps of: producing a mixture of α-lipoic acid, an alkaline substance and water to prepare an α-lipoic acid-containing aqueous dispersion liquid (it is believed that, in the aqueous dispersion liquid, the α-lipoic acid forms micelles); adding the nonionic surfactant into the aqueous dispersion liquid (it is believed that mixed micelles of the α-lipoic acid with the nonionic surfactant form); adding a divalent metal salt into the aqueous dispersion liquid, wherein the divalent metal salt is a divalent metal halide, a divalent metal acetate or a divalent metal gluconate; and adding an alkali metal carbonate or an alkali metal phosphate into the aqueous dispersion liquid wherein the divalent metal salt has been added, thereby forming α-lipoic acid nanoparticles.

(2a-1. Step of Dissolving α-Lipoic Acid in Nonionic Surfactant in Liquid Form)

An embodiment of initially dissolving α-lipoic acid in a nonionic surfactant will be described. In this embodiment, the nonionic surfactant is used as a solvent. That is, a surfactant solution is prepared. In this embodiment, first, α-lipoic acid is dissolved in a nonionic surfactant in a liquid form, and thereby a surfactant solution is obtained. This α-lipoic acid may be added directly to the nonionic surfactant, or may be added indirectly. The phrase "added indirectly" refers to adding after mixed with another substance. For example, α-lipoic acid may be added to the nonionic surfactant after being mixed with an additive. α-Lipoic acid is usually marketed in the form of crystals or powder. In this embodiment, α-lipoic acid dissolves almost completely in the nonionic surfactant in a liquid form. If the nonionic surfactant is liquid at room temperature, this dissolution operation can be carried out at room temperature, but if necessary, the nonionic surfactant may be heated and then the dissolution operation can be carried out. If the nonionic surfactant is solid at room temperature, the nonionic surfactant is heated to a liquid form, and then this dissolution operation is carried out. Upon preparing this surfactant solution, the nonionic surfactant may have the above-mentioned additive added therein, as necessary.

When this surfactant solution is prepared, preferably, water is not used. That is, the amount of water incorporated upon preparing a surfactant solution is preferably set at about 50 parts by weight or less, more preferably about 20 parts by weight or less, even more preferably about 10 parts by weight or less; still more preferably about 5 parts by weight or less, and particularly preferably about 1 part by weight or less, relative to 100 parts by weight of α-lipoic acid. The lower limit of the water amount is not particularly defined, but conditions in which water of about 0.001 parts by weight or more, about 0.01 parts by weight or more, or about 0.1 parts by weight or more, relative to 100 parts by weight of α-lipoic acid is mixed may be employed.

α-Lipoic acid can be dissolved in alcohol, but in the present inventions, it is preferable not to use alcohol substantially. When alcohol is used, adverse effects may be exerted on the efficiency of micelle formation by α-lipoic acid. Therefore, for example, it is preferable to set the amount of use of the alcohol at about 10 parts by weight or less, more preferably at about 5 parts by weight or less, even more preferably at about 1 part by weight or less, particularly preferably at about 0.5 parts by weight or less, and most preferably at about 0.1 parts by weight or less, relative to 100 parts by weight of α-lipoic acid. Provided that, in the case of using alcohol according to necessity, the lower limit of the amount of use of the alcohol is not particularly defined, but for example, it is possible to set the amount of use of the alcohol at about 0.01 parts by weight or more, relative to 100 parts by weight of α-lipoic acid.

It is noted that in the embodiment that will be described later, an alkaline compound is used when α-lipoic acid is dissolved, but in the present embodiment, there is no need to use an alkaline compound to dissolve α-lipoic acid. In the present embodiment, when α-lipoic acid is dissolved in the nonionic surfactant, preferably, the dissolution operation is carried out without using any material other than α-lipoic acid and the nonionic surfactant. For example, the dissolution operation can be carried out without substantially using an alkaline compound. Therefore, in regard to the amount of the alkaline compound used upon carrying out the dissolution operation, for example, the amount of use of the alkaline compound can be set at 5 parts by weight or less, can be set at about 1 part by weight or less, can be set at about 0.5 parts by weight or less, can be set at about 0.1 parts by weight or less, can be set at about 0.05 parts by weight or less, and can also be set at about 0.01 parts by weight or less, relative to 100 parts by weight of α-lipoic acid.

It is noted that when water is added after α-lipoic acid is dissolved in the nonionic surfactant, alkali may be added simultaneously with water, or alkaline water (for example, an aqueous solution of a basic compound) may be added, as necessary.

A nonionic surfactant which has a melting point above room temperature, is preferably heated to melt. The heating may be carried out such that the temperature of the nonionic surfactant used reaches the temperature which is sufficient for the nonionic surfactant to melt. Since it is feared that heating may decompose α-lipoic acid, excessive heating, such that the temperature of the nonionic surfactant reaches about 70° C. or above, is not preferable. The temperature of the nonionic surfactant at the time of adding α-lipoic acid, is preferably higher than the melting temperature of this nonionic surfactant, and is preferably (melting point+20° C.) or lower, more preferably (melting point+15° C.) or lower, and most preferably (melting point+10° C.) or lower.

During the production of a mixture of the nonionic surfactant and α-lipoic acid, another substance may be additionally mixed, as long as the substance does not substantially exert any adverse effects on the mixing (micelle formation) of α-lipoic acid and the nonionic surfactant. For example, the mixture may be produced by mixing the nonionic surfactant and an additive (for example, polyethylene glycol) and then adding α-lipoic acid. Alternatively, an additive (for example, polyethylene glycol) may be added to a mixture of nonionic surfactant and α-lipoic acid.

It is preferable to stir the mixture satisfactorily after α-lipoic acid has been added.

The amount of α-lipoic acid is selected such that the concentration of α-lipoic acid in the α-lipoic acid-containing aqueous dispersion liquid obtained in step 2b-1 is at or above the critical micelle concentration. The concentration of α-lipoic acid in the α-lipoic acid-containing aqueous dispersion liquid is preferably about 0.1% by weight or more, more preferably about 0.5% by weight or more, and more preferably about 1.0% by weight or more. The concentration of α-lipoic acid in the α-lipoic acid-containing aqueous dispersion liquid is preferably about 20% by weight or less, more preferably about 16% by weight or less, even more preferably about 14% by weight or less, particularly preferably about 12% by weight or less, and most preferably about 10% by weight or less.

The amount of the nonionic surfactant used to dissolve α-lipoic acid can be arbitrarily selected, but when the amount of α-lipoic acid is taken as 100, the amount of the nonionic surfactant is, on the basis of weight, preferably about 100% or more, more preferably about 200% or more, even more preferably about 300% or more, particularly preferably about 400% or more, and most preferably about 500% or more. The amount of the nonionic surfactant that is added through this step is, when the amount of α-lipoic acid is taken as 100%, on a weight basis, preferably about 4000% or less, more preferably about 3500% or less, even more preferably about 3000% or less, particularly preferably about 2500% or less, and most preferably about 2000% or less.

(2b-1. Step of Obtaining α-Lipoic Acid-Containing Aqueous Dispersion Liquid by Adding Water to a Mixture of Nonionic Surfactant and α-Lipoic Acid)

Subsequently, an α-lipoic acid-containing aqueous dispersion liquid is obtained by adding water to the mixture of the nonionic surfactant and α-lipoic acid. During the production of the α-lipoic acid-containing aqueous dispersion liquid, another substance may be additionally mixed, as long as the substance does not substantially exert adverse effects on the mixing (micelle formation) of α-lipoic acid and the nonionic surfactant.

It is thought that when water is added and mixed with the mixture of the nonionic surfactant and α-lipoic acid, mixed micelles of α-lipoic acid and the nonionic surfactant are spontaneously formed. In this embodiment, since it is believed that mixed micelles are formed from a state in which the α-lipoic acid and the nonionic surfactant are regularly arranged, at one time through the addition of water, it is thought that the mixed micelles can be formed very stably. It is preferable to satisfactorily stir the solution after water has been added. The stirring is preferably continued for a certain length of time. The stirring time is preferably about 10 minutes or longer, more preferably about 20 minutes or longer, even more preferably about 25 minutes or longer, and most preferably about 30 minutes or longer. There is no particular upper limit in the stirring time. For example, the stirring time can be set at any value, such as about 48 hours or less, about 24 hours or less, about 18 hours or less, about 12 hours or less, about 6 hours or less, about 4 hours or less, about 2 hours or less, about 1 hour or less, about 50 minutes or less, about 40 minutes or less, or about 35 minutes or less.

In this manner, an aqueous dispersion liquid containing α-lipoic acid and a nonionic surfactant is obtained.

(2a-2. Step of Mixing α-Lipoic Acid and Alkali)

In the method of the present invention according to the embodiment of initially mixing α-lipoic acid with an alkali, first, a mixture of α-lipoic acid, the alkaline substance and water is produced, and thus an α-lipoic acid-containing aqueous dispersion liquid is prepared. α-Lipoic acid is usually marketed in the form of crystals or powder. When α-lipoic acid is added to water, α-lipoic acid undergoes dispersion but is never completely dissolved. α-Lipoic acid is dissolved in alcohol, but in the present inventions, it is preferable not to use alcohol. If alcohol is used, adverse effects may be exerted on the efficiency of micelle formation by α-lipoic acid. The alkaline substance may be any alkaline substance, but is preferably a strong base, and more preferably sodium hydroxide.

The α-lipoic acid-containing aqueous dispersion liquid can be produced by, for example, first adding α-lipoic acid into water to mix them, and adding an alkaline solution to the mixture to mix therewith. The α-lipoic acid-containing aqueous dispersion liquid can also be produced by adding α-lipoic acid into water to mix them, and adding an alkaline substance to the mixture to mix therewith. The α-lipoic acid-containing aqueous dispersion liquid can also be produced by adding α-lipoic acid into an alkaline solution, and mixing them. The α-lipoic acid-containing aqueous dispersion liquid can also be produced by adding α-lipoic acid and an alkaline substance into water, and mixing them.

During the production of the α-lipoic acid-containing aqueous dispersion liquid, another substance may be additionally mixed thereinto, as long as the substance does not substantially exert adverse effects on the mixing (micelle formation) of α-lipoic acid and the alkali.

The amount of α-lipoic acid used for the production of the α-lipoic acid-containing aqueous dispersion liquid, is selected such that the concentration of α-lipoic acid in the α-lipoic acid-containing aqueous dispersion liquid is at or above the critical micelle concentration. The concentration of α-lipoic acid in the α-lipoic acid-containing aqueous dispersion liquid is preferably about 0.1% by weight or more, more preferably about 0.5% by weight or more, and even more preferably about 1.0% by weight or more. The concentration of α-lipoic acid in the α-lipoic acid-containing aqueous dispersion liquid is preferably about 20% by weight or less, more preferably about 16% by weight or less, even more preferably about 14% by weight or less, particularly preferably about 12% by weight or less, and most preferably about 10% by weight or less.

The amount of the alkaline substance used for the production of the α-lipoic acid-containing aqueous dispersion liquid can be any amount, as long as the amount is capable of allowing α-lipoic acid to be dispersed in water. The amount of the alkaline substance is preferably an amount that brings the pH of the α-lipoic acid-containing aqueous dispersion liquid to about 6.5 or higher. The amount of the alkaline substance is preferably an amount that brings the pH of the α-lipoic acid-containing aqueous dispersion liquid to about 13.5 or lower, more preferably an amount that brings the pH of the α-lipoic acid-containing aqueous dispersion liquid to about 13.0 or lower, and particularly preferably an amount that brings the pH of the α-lipoic acid-containing aqueous dispersion liquid to about 12.5 or lower.

In this manner, an α-lipoic acid-containing aqueous dispersion liquid is obtained.

(2b-2. Step of Adding α-Lipoic Acid-Containing Aqueous Dispersion Liquid and Nonionic Surfactant)

Subsequently, a nonionic surfactant is added to this α-lipoic acid-containing aqueous dispersion liquid. Since the surfaces of the micelles of α-lipoic acid are in the state of being covered with negative charges, divalent metal ions, for example, calcium ions ($Ca^{2+}$), can easily be adsorbed (bound) to cause an exchange reaction with sodium ions. In this case, since divalent metal ions have higher adsorption capacity (binding capacity) as compared with sodium ions, the micelles having the divalent metal ions adsorbed thereto become insoluble in water as the charges at the micelle surface, become difficult to dissociate, and the micelles precipitate. When precipitation occurs, aggregation between particles occurs, and very large particles are formed. In order to prevent aggregation of particles at this stage, a nonionic surfactant is added. The nonionic surfactant forms mixed micelles together with α-lipoic acid, and protrudes hydrophilic groups at the micelle surface. Thus, it is thought that even if polyvalent metal ions are adsorbed (bound) to the micelle surface, the presence of the hydrophilic group protruded at the micelle surface prevents the precipitation of micelles.

The amount of the nonionic surfactant that is added in this step can be arbitrarily selected, but when the concentration of α-lipoic acid is taken as 100, the amount of the nonionic surfactant is, on a weight basis, preferably about 100% or more, more preferably about 200% or more, even more preferably about 300% or more, particularly preferably about 400% or more, and most preferably about 500% or more. The amount of the nonionic surfactant that is added in this step, when the concentration of α-lipoic acid is taken as 100%, on a weight basis, is preferably about 4000% or less, more preferably about 3500% or less, even more preferably about 3000% or less, particularly preferably about 2500% or less, and most preferably about 2000% or less.

It is speculated that mixed micelles of α-lipoic acid and the nonionic surfactant are spontaneously formed when the nonionic surfactant is added to the α-lipoic acid-containing aqueous dispersion liquid to mix. It is preferable to satisfactorily stir the solution after the nonionic surfactant has been added. The stirring is preferably continued for a certain length of time. The stirring time is preferably about 10 minutes or longer, more preferably about 20 minutes or longer, even more preferably about 25 minutes or longer, and most preferably about 30 minutes or longer. There is no particular upper limit in the stirring time. For example, the stirring time can be set at any value, such as about 48 hours or less, about 24 hours or less, about 18 hours or less, about 12 hours or less, about 6 hours or less, about 4 hours or less, about 2 hours or less, about 1 hour or less, about 50 minutes or less, about 40 minutes or less, or about 35 minutes or less.

In this manner, an aqueous dispersion liquid containing α-lipoic acid and a nonionic surfactant is obtained.

(2c. Step of Adding Divalent Metal Salt)

Subsequently, a divalent metal salt is added to the aqueous dispersion liquid prepared in the above step 2b-1 or step 2b-2. The divalent metal salt may be directly added to this aqueous dispersion liquid, or may be added in the form of an aqueous solution, but preferably, the divalent metal salt is added as an aqueous solution of the divalent metal salt.

The aqueous dispersion liquid to which the divalent metal salt is to be added, can be directly used as received from the previous step, but preferably, the pH is adjusted immediately before the metal salt is added, in accordance with the metal salt used.

The inventors of the present invention found that with regard to α-lipoic acid, the pH that is preferable for the dispersion of α-lipoic acid is different from the pH that is preferable for the addition of the divalent metal salt, and that when the divalent metal ion is added to the aqueous dispersion liquid containing the mixed micelles containing α-lipoic acid and the nonionic surfactant, there exists a pH value which is preferable depending on the kind of metal ion. This pH is desirably about 12.0 or lower when the divalent metal ion is $Mg^{2+}$, about 12.0 or lower in the case of $Ca^{2+}$, and about 9.5 or lower in the case of $Zn^{2+}$, and more desirably about 11.5 or lower in the case of $Mg^{2+}$, about 11.5 or lower in the case of $Ca^{2+}$, and about 8.8 or lower in the case of $Zn^{2+}$.

When the divalent metal salt is calcium chloride, calcium bromide, calcium fluoride, calcium iodide, calcium acetate or calcium gluconate, the pH of the aqueous dispersion liquid immediately before the addition of divalent metal salt is preferably about 3.4 or higher, more preferably about 3.6 or higher, particularly preferably about 3.8 or higher, and most preferably about 4.0 or higher; and the pH of the aqueous dispersion liquid immediately before the addition of divalent metal salt is preferably about 12.0 or lower, more preferably about 11.9 or lower, particularly preferably about 11.7 or lower, and most preferably about 11.5 or lower.

When the divalent metal salt is magnesium chloride, magnesium bromide, magnesium fluoride, magnesium iodide, magnesium acetate or magnesium gluconate, the pH of the aqueous dispersion liquid immediately before the addition of divalent metal salt is preferably about 3.4 or higher, more preferably about 3.6 or higher, particularly preferably about 3.8 or higher, and most preferably about 4.0 or higher; and the pH of the aqueous dispersion liquid immediately before the addition of divalent metal salt is preferably about 12.0 or lower, more preferably about 11.9 or lower, particularly preferably about 11.7 or lower, and most preferably about 11.5 or lower.

When the divalent metal salt is zinc chloride, zinc bromide, zinc fluoride, zinc iodide, zinc acetate or zinc gluconate, the pH of the aqueous dispersion liquid immediately before the addition of divalent metal salt is preferably about 3.5 or higher, more preferably about 3.7 or higher, and most preferably about 3.9 or higher; and the pH of the aqueous dispersion liquid immediately before the addition of divalent metal salt is preferably about 9.5 or lower, more preferably about 9.2 or lower, and most preferably about 8.8 or lower.

The amount of the divalent metal salt added in this step can be arbitrarily selected, but when the concentration of α-lipoic acid is taken as 100, the amount is, on a molar basis, preferably about 10% or more, more preferably about 20% or more, even more preferably about 30% or more, particularly preferably about 40% or more, and most preferably about 50% or more. The amount of the divalent metal salt added in this step, when the concentration of α-lipoic acid is taken as 100%, on a molar basis, is preferably about 200% or less, more preferably about 160% or less, even more preferably about 140% or less, particularly preferably about 120% or less, and most preferably about 100% or less.

It is thought that by adding the divalent metal salt into the aqueous dispersion liquid and mixing therewith, divalent metal ions bind to the negative charges at the surface of the mixed micelles, and thereby aggregation and precipitation of the micelles of α-lipoic acid are prevented. It is preferable to satisfactorily stir the solution after the divalent metal salt has been added. The stirring is preferably continued for a certain length of time. The stirring time is preferably about 10 minutes or longer, more preferably about 20 minutes or longer, even more preferably about 25 minutes or longer, and most preferably about 30 minutes or longer. There is no particular upper limit in the stirring time. For example, the stirring time can be set at any value, such as about 48 hours or less, about 24 hours or less, about 18 hours or less, about 12 hours or less, about 6 hours or less, about 4 hours or less, about 2 hours or less, about 1 hour or less, about 50 minutes or less, about 40 minutes or less, or about 35 minutes or less.

(2d. Step of Adding Alkali Metal Carbonate or Alkali Metal Phosphate)

Subsequently, an alkali metal carbonate or an alkali metal phosphate is added to this aqueous dispersion liquid to which the divalent metal salt has been added.

The amount of the alkali metal carbonate and alkali metal phosphate (also referred to as "salt carrying a divalent anion") can be selected to be any amount, but when the amount of the divalent metal salt added is taken as 1, the amount of the salt carrying a divalent anion is, on a molar basis, preferably about 0.01 or more, more preferably about 0.02 or more, and even more preferably about 0.1 or more. When the amount of the divalent metal salt added is taken as 1, the amount of the salt carrying a divalent anion is, on a molar basis, preferably about 0.80 or less, more preferably about 0.70 or less, and even more preferably about 0.60 or less. In a particular embodiment, when the amount of the divalent metal salt added is taken as 1, the amount of the salt carrying a divalent anion may be, for example, on a molar basis, about 0.60 or less, about 0.50 or less, or about 0.40 or less. When the amount of the divalent metal salt added is taken as 1, the amount of the salt carrying a divalent anion is most preferably 0.2 on a molar basis. If the amount of the salt carrying a divalent anion is too small relative to the amount of the divalent metal salt, the positive charge at the micelle surface is not neutralized, and the efficiency of preventing the aggregation and precipitation of micelles may be lowered. If the amount of the salt carrying a divalent anion is too large relative to the amount of the divalent metal salt, precipitation may become prone to occur.

For example, when the molar ratio of magnesium chloride and sodium carbonate is set at 1:1, precipitation occurs when the mixture is left to stand for a whole day, but when the molar ratio is set at 1:0.01 to 0.8, and particularly up to 1:0.4, the mixture remains transparent and precipitation does not occur even when left to stand for a long period time. When the mixture becomes turbid or precipitation occurs, it is because the particle size of the formed particles is too large. If the particle size is too large, skin permeability becomes poor, and there would be inconvenience even in the case of performing injection. However, when the mixture is transparent and precipitation does not occur, the particle size of the formed particles is small, and the distribution is narrow. Therefore, skin permeability is good, and inconvenience does not occur upon performing injection.

In this manner, α-lipoic acid nanoparticles are formed in an aqueous dispersion liquid.

The amount of the salt carrying a divalent anion that is added in this step can be selected to be any amount, but when the concentration of α-lipoic acid is taken as 100, the amount is, on a molar basis, preferably about 0.1% or more, more preferably about 0.5% or more, even more preferably about 1.0% or more, particularly preferably about 1.5% or more, and most preferably about 2.0% or more. The amount of the salt carrying a divalent anion that is added in this step is, when the concentration of α-lipoic acid is taken as 100%, on a molar basis, preferably about 80% or less, more preferably about 74% or less, even more preferably about 68% or less, particularly preferably about 62% or less, and most preferably about 60% or less. In a particular embodiment, the amount of the salt carrying a divalent anion that is added in this step is, when the concentration of α-lipoic acid is taken as 100%, for example, on a molar basis, about 50% or less, about 46% or less, about 44% or less, about 42% or less, or about 40%.

It is thought that by adding the salt carrying a divalent anion into the aqueous dispersion liquid which has been added with a divalent metal salt and mixing therewith, the divalent anions bind to the divalent metal ions that are bound to the micelle surface. It is thought that by binding the divalent anions to the divalent metal salt that is bound to the micelle surface, the charge at the micelle surface is substantially neutralized. It is thought that at the micelle surface, the divalent metal ions and the divalent anions bind to each other to form a polyvalent metal inorganic salt. It is thought that as such, a coating of a polyvalent metal inorganic salt is formed at the micelle surface, and as a result, precipitation due to binding between micelles is prevented.

It is preferable to satisfactorily stir the solution after the alkali metal carbonate or alkali metal phosphate has been added. The stirring is preferably continued for a certain length of time. The stirring time is preferably about 10 minutes or longer, more preferably about 20 minutes or longer, even more preferably about 25 minutes or longer, and most preferably about 30 minutes or longer. There is no particular upper limit in the stirring time. For example, the stirring time can be set at any value, such as about 48 hours or less, about 24 hours or less, about 18 hours or less, about 12 hours or less, about 6 hours or less, about 4 hours or less, about 2 hours or less, about 1 hour or less, about 50 minutes or less, about 40 minutes or less, or about 35 minutes or less.

(2e. Other Steps)

By carrying out the respective steps described above, nanoparticles of α-lipoic acid are formed in an aqueous dispersion liquid. This aqueous dispersion liquid can be dried to obtain a powder, as necessary. Drying can be carried out according to any method that is known in the art. The drying is carried out by, for example, freeze-drying, spray drying, drum drying or the like. Freeze-drying is preferred. The powder containing the α-lipoic acid nanoparticles produced according to the method of the present invention is, if added to water, easily dispersed to form a transparent liquid.

(3. α-Lipoic Acid Nanoparticles)

The α-lipoic acid nanoparticles of the present invention contain α-lipoic acid, a nonionic surfactant, a divalent metal ion, and a carbonate ion or a phosphate ion.

The amount of the nonionic surfactant in the α-lipoic acid nanoparticles of the present invention, when the concentration of α-lipoic acid is taken as 100, on a weight basis, is preferably about 100% or more, more preferably about 200% or more, even more preferably about 300% or more, particularly preferably about 400% or more, and most preferably about 500% or more. The amount of the nonionic surfactant in the α-lipoic acid nanoparticles of the present invention, when the concentration of α-lipoic acid is taken as 100%, on a weight basis, is preferably about 4000% or less, more preferably about 3500% or less, even more preferably about 3000% or less, particularly preferably about 2500% or less, and most preferably about 2000% or less.

The amount of the divalent metal ion in the α-lipoic acid nanoparticles of the present invention, when the concentration of α-lipoic acid is taken as 100, on a molar basis, is preferably about 10% or more, more preferably about 20% or more, even more preferably about 30% or more, particularly preferably about 40% or more, and most preferably about 50% or more. The amount of the divalent metal ion in the α-lipoic acid nanoparticles of the present invention, when the concentration of α-lipoic acid is taken as 100%, on a molar basis, is preferably about 200% or less, more preferably about 160% or less, even more preferably about 140% or less, particularly preferably about 120% or less, and most preferably about 100% or less.

The amount of the carbonate ion or phosphate ion (also referred to as divalent anion) in the α-lipoic acid nanoparticles of the present invention, when the concentration of α-lipoic acid is taken as 100, on a molar basis, is preferably about 0.1% or more, more preferably about 0.5% or more, even more preferably about 1.0% or more, particularly preferably about 1.5% or more, and most preferably about 2.0% or more. The amount of the carbonate ion or phosphate ion in the α-lipoic acid nanoparticles of the present invention, when the concentration of α-lipoic acid is taken as 100%, on a molar basis, is preferably about 80% or less, more preferably about 74% or less, even more preferably about 68% or less, particularly preferably about 62% or less, and most preferably about 60% or less. In a particular embodiment, the amount of the salt carrying a divalent anion that is added in this step, when the concentration of α-lipoic acid is taken as 100%, on a molar basis, is for example, about 50% or less, about 46% or less, about 44% or less, about 42% or less, or about 40% or less.

The divalent metal ion in the α-lipoic acid nanoparticles of the present invention is preferably calcium ion, zinc ion or magnesium ion.

When the amount of the divalent metal ion in the α-lipoic acid nanoparticles of the present invention is taken as 1, the amount of the divalent anion, on a molar basis, is preferably about 0.01 or more, more preferably about 0.10 or more, and even more preferably about 0.20 or more. When the amount of the divalent metal ion in the α-lipoic acid nanoparticles of the present invention is taken as 1, the amount of the divalent anion, on a molar basis, is preferably about 0.80 or less, more preferably about 0.50 or less, and even more preferably about 0.40 or less. When the amount of the divalent metal ion in the α-lipoic acid nanoparticles of the present invention is taken as 1, the amount of the divalent anion is most preferably about 0.2 on a molar basis.

(4. Uses of α-Lipoic Acid Nanoparticles)

The α-lipoic acid nanoparticles of the present invention can be used in various applications where α-lipoic acid has been conventionally used. Examples of these applications include an external preparation for skin, a pharmaceutical product (including injection liquid), a composition for oral cavity and a food.

(4a. External Preparation for Skin Containing α-Lipoic Acid Nanoparticles)

The external preparation for skin of the present invention contains the α-lipoic acid nanoparticles of the present invention.

In the present specification, the term "external preparation for skin" refers to a preparation to be used for the skin, which achieves a desired effect when in contact with the skin. The present invention is particularly effective in the applications where the preparation is continuously contacted with the skin for a long period of time (for example, an application where the preparation is continuously contacted with the skin for about one hour or longer, or an application where the preparation is continuously contacted with the skin for about 5 hours or longer).

A preferred example of the external preparation for skin is a cosmetic preparation.

Preferred examples of the cosmetic preparations include skin care cosmetic preparations. Specific examples of the cosmetic preparations include skin care cosmetic preparations such as skin lotion, emulsion and cream; cosmetics such as foundation, eye shadow, lipstick and rouge for cheek; hair cosmetic preparations, emollient cream, emollient lotion, cream, cream rinse, cold cream, vanishing cream, lotion, facial mask, gel, face pack, soap, body soap, shampoo, conditioner, rinse, bath agent, bath medicine, face wash, shaving cream, hair cream, hair lotion, hair treatment, hair pack, gloss, lip cream, cake, and the like. The present invention is particularly effective in applications in which a moisturizing effect is desired. For example, the present invention is effective as a skincare cosmetic preparation. The invention is particularly effective in applications contacting with the skin for a long period of time, but also effective in applications such as face wash and shampoo where it is washed away after use for a short period of time.

As described above, cosmetics are also included in the cosmetic preparations. Cosmetics are classified into cosmetics for cleaning, cosmetics for hair, basic cosmetics, makeup cosmetics, fragrant cosmetics, cosmetics for sun-burn, cosmetics for anti-sunburn, nail cosmetics, eye liner cosmetics, eye shadow cosmetics, rouge for cheek, lip cosmetics, oral cavity cosmetics, and the like. The present invention is effective in any application of them.

Furthermore, the external preparation for skin may be a pharmaceutical product or a quasi-drug. For example, the α-lipoic acid nanoparticles may be blended to an ointment containing a pharmaceutically effective component.

Blending of α-lipoic acid nanoparticles to an external preparation for skin (for example, cosmetic or quasi drug such as emulsion, skin lotion, cream, shampoo, or face wash) results in an external preparation for skin that is effective in the prevention and treatment of wrinkles, spots, freckles, pigmentation and the like. The external preparation for skin of the present invention also increases skin moisturization and is effective for alleviation of symptoms such as dry skin, skin roughening, allergy and atopic dermatitis. The external preparation for skin of the present invention activates skin metabolism by exerting an antioxidant capacity. Further, the external preparation for skin of the present invention rapidly removes melanin dye and active oxygen generated by ultraviolet irradiation, thus exhibiting a whitening effect, and is effective for preventing skin damage. Therefore, the external preparation for skin containing the α-lipoic acid nanoparticles of the present invention is effective to alleviate adverse effect on the skin caused by drying and ultraviolet ray, to improve pigmentation disorder such as spots or freckles, and to delay aging phenomena such as dullness, wrinkles, sag and alopecia.

Examples of the dosage forms of the external preparation for skin of the present invention include ointments, thickening gel systems, lotions, water in oil emulsions, oil in water emulsions, solids, sheets, powders, gels, mousse and sprays. The external preparation for skin may be a product in the shape of a sheet impregnated with the preparation such as a makeup removing facial mask.

When the dosage form of the external preparation for skin is a lotion, emulsion, thickening gel system or the like, in terms of improvement of its effect, it is preferable to blend among the components above, in particular among the thickeners, a water-soluble thickener consisting of, for example, a plant-derived macromolecule such as gum arabic, tragacanth gum, galactan, guar gum, carrageenan, locust bean gum, pectin, quince seed (*Cyclonia oblonga* seed) extract, or brown algae powder; a microbial-derived macromolecule such as xanthan gum, dextran, or pullulan; an animal-derived macromolecule such as collagen, casein, albumin, gelatin or hyaluronic acid; starches such as carboxymethyl starch or methylhydroxy starch; celluloses such as methylcellulose, nitrocellulose, ethyl cellulose, methylhydroxypropyl cellulose, hydroxyethyl cellulose, cellulose sulfate salt, hydroxypropyl cellulose, carboxymethyl cellulose, crystalline cellulose, or cellulose powder; a vinyl-type macromolecule such as polyvinyl alcohol, polyvinyl methyl ether, polyvinyl pyrrolidone or carboxy vinyl polymer; an acrylic-type macromolecule such as polyacrylic acid or the salt thereof or polyacrylimide; an organic thickener such as glycyrrhizic acid or alginic acid; an inorganic thickener such as bentonite, hectolite, labonite, magnesium aluminum silicate, or silicic anhydride; in combination with a lower alcohol such as ethanol or isopropanol among the alcohols.

The external preparation for skin of the present invention can be produced by a known method.

In the present specification, the concept of the external preparation for skin also encompasses clothes containing the α-lipoic acid nanoparticles used in the utilization methods in which, by binding the α-lipoic acid nanoparticles to the fibers, mixing the α-lipoic acid nanoparticles into the fiber material, impregnating the α-lipoic acid nanoparticles into fibers, or applying the α-lipoic acid nanoparticles on the surface of fabric, the α-lipoic acid nanoparticles are transdermally absorbed when the clothes (for example, underwear or the like) produced from the fibers or fabric are contacted with the skin. Binding of the α-lipoic acid nanoparticles to fibers can be carried out by, for example, crosslinking or the like. The method of binding a compound to fibers, the method of mixing a compound into a fiber material, the method of impregnating a compound into fibers, the method of applying a compound on the surface of fabric, and the like are known in the art.

Adding of the α-lipoic acid nanoparticles synthesized by the method of the present invention, into a external preparation for skin, does not require any special process, and the α-lipoic acid nanoparticles are added together with the raw materials in the early stage of the production process of the external preparation for skin, or added in the middle of the production process, or added at the final stage of the production process. In regard to the mode of addition, conventional methods such as mixing, kneading, dissolution, immersion, spreading, spraying and applying are selected in accordance with the kind and properties of the external preparation for skin. The external preparation for skin synthesized by the method of the present invention can be prepared according to the methods that are known to those skilled in the art.

When the content of the α-lipoic acid nanoparticles contained in the external preparation for skin of the present invention is converted to α-lipoic acid, the content is preferably about 0.002% by weight or more, more preferably about 0.01% by weight or more, even more preferably about 0.1% by weight or more, particularly preferably about 0.5% by weight or more, and most preferably about 1.0% by weight or more. When the content of the α-lipoic acid nanoparticles contained in the external preparation for skin of the present invention is converted to α-lipoic acid, the content is preferably about 10% by weight or less, more preferably about 8% by weight or less, even more preferably about 5% by weight or less, particularly preferably about 4% by weight or less, and most preferably about 3% by weight or less.

(4b. Sustained Release External Preparation for Skin Containing α-Lipoic Acid Nanoparticles)

The external preparation for skin of the present invention may be a sustained release preparation. The sustained release preparation may be a solid, a semi-solid or a liquid, but is preferably a liquid.

Addition of the α-lipoic acid nanoparticles synthesized by the method of the present invention, into a sustained release preparation, does not require any special process, and the α-lipoic acid nanoparticles are added together with the raw materials in the early stage of the production process of the sustained release preparation, or added in the middle of the production process, or added at the final stage of the production process. In regard to the mode of addition, conventional methods such as mixing, kneading, dissolution, immersion, spreading, spraying and applying, are selected in accordance with the kind and properties of the sustained release preparation. The sustained release preparation of the present invention can be prepared according to the methods that are known to those skilled in the art.

When the content of the α-lipoic acid nanoparticles contained in the sustained release preparation of the present invention is converted to α-lipoic acid, the content is preferably about 0.002% by weight or more, more preferably about 0.01% by weight or more, even more preferably about 0.1% by weight or more, particularly preferably about 0.5% by weight or more, and most preferably about 1.0% by weight or more. When the content of the α-lipoic acid nanoparticles contained in the sustained release preparation of the present invention is converted to α-lipoic acid, the content is preferably about 10% by weight or less, more preferably about 8% by weight or less, even more preferably about 5% by weight or less, particularly preferably about 4% by weight or less, and most preferably about 3% by weight or less.

(4c. Composition for Oral Cavity Containing α-Lipoic Acid Nanoparticles)

The composition for oral cavity of the present invention contains the α-lipoic acid nanoparticles of the present invention. The composition for oral cavity may be any composition for oral cavity. The composition for oral cavity may be a solid, a semisolid or a liquid, but is preferably a liquid. Examples of the composition for oral cavity include toothpaste (for example, cream toothpaste, powdered toothpaste, and the like), dental cream, oral rinse (including mouthwash), mouth spray, disintegrative film, gel, and troche.

Adding of the α-lipoic acid nanoparticles synthesized by the method of the present invention, into a composition for oral cavity, does not require any special process, and the α-lipoic acid nanoparticles are added together with the raw materials in the early stage of the production process of the composition for oral cavity, or added in the middle of the production process, or added at the final stage of the production process. In regard to the mode of addition, conventional methods such as mixing, kneading, dissolution, immersion, spreading, spraying and applying, are selected in accordance with the kind and properties of the composition for oral cavity. The composition for oral cavity of the present invention can be prepared according to the methods that are known to those skilled in the art.

When the content of the α-lipoic acid nanoparticles contained in the composition for oral cavity of the present invention is converted to α-lipoic acid, the content is preferably about 0.002% by weight or more, more preferably about 0.01% by weight or more, even more preferably about 0.1% by weight or more, particularly preferably about 0.5% by weight or more, and most preferably about 1.0% by weight or more. When the content of the α-lipoic acid nanoparticles contained in the composition for oral cavity of the present invention is converted to α-lipoic acid, the content is preferably about 10% by weight or less, more preferably about 8% by weight or less, even more preferably about 5% by weight or less, particularly preferably about 4% by weight or less, and most preferably about 3% by weight or less.

(4e. Food Containing α-Lipoic Acid Nanoparticles)

The food of the present invention contains the α-lipoic acid nanoparticles of the present invention. The food may be any food. The food may be a solid, a semisolid or a liquid, but is preferably a liquid. The food is preferably a health food, and more preferably a health beverage, but the food is not limited thereto. The health food may be used for the same conventional applications as those of the α-lipoic acid contained in the health food. Examples of the use and efficacy of the health food include wrinkles, spots, freckles, pigmentation and the like.

The food may be, for example, frozen desserts (ice cream, ice milk, iced dessert, and the like), favorite beverages (for example, refreshing beverages, carbonated drinks (cider, lemonade, and the like), flavoring drinks, alcohol drinks, powdered juice and the like), dairy products (milk, yogurt, ice cream, butter, margarine, cheese, whipping cream, and the like), confectionery (Western confectionery, Japanese confectionery, snacks, and the like, for example, bean jam, bean jelly, buns with bean-jam filling, chocolate, gum, jelly, agar, almond jelly, cake, castella, cookies, rice crackers, tablet confectionery, and the like), bread, rice cake, fishery processed products (kamaboko (boiled fish paste), chikuwa (fish sausage), and the like), meat processed products (sausage, ham, and the like), fruit processed products (jam, marmalade, fruit sauce, and the like), seasonings (dressing, mayonnaise, miso, and the like), noodles (wheat noodles, buckwheat noodles, and the like), pickles, and bottled products and canned products of meat, fish and fruits, and the like.

Adding of the α-lipoic acid nanoparticles synthesized by the method of the present invention, into a food, does not require any special process, and the α-lipoic acid nanoparticles are added together with the raw materials in the early stage of the production process of the food, or added in the middle of the production process, or added at the final stage of the production process. In regard to the mode of addition, conventional methods such as mixing, kneading, dissolution, immersion, spreading, spraying and applying, are selected in accordance with the kind and properties of the food. The food of the present invention can be prepared according to the methods that are known to those skilled in the art.

When the content of the α-lipoic acid nanoparticles contained in the food of the present invention is converted to α-lipoic acid, the content is preferably about 0.01% by weight or more, more preferably about 0.05% by weight or more, even more preferably about 0.1% by weight or more, particularly preferably about 0.5% by weight or more, and most preferably about 1.0% by weight or more. When the content of the α-lipoic acid nanoparticles contained in the food of the present invention is converted to α-lipoic acid, the content is preferably about 10% by weight or less, more preferably about 8% by weight or less, even more preferably about 5% by weight or less, particularly preferably about 4% by weight or less, and most preferably about 3% by weight or less.

(4f. Pharmaceutical Product Containing α-Lipoic Acid Nanoparticles)

The pharmaceutical product of the present invention contains the α-lipoic acid nanoparticles of the present invention. The pharmaceutical product may be any pharmaceutical product. The form of the pharmaceutical product may be any form. The pharmaceutical product of the present invention may be a powder, a granule, a tablet, a capsule, a pill, a liquid, a dispersion, an ointment, a cream or the like. When the pharmaceutical product of the present invention is used for the applications of oral administration, the pharmaceutical product of the present invention is preferably in the form of a tablet, powdered preparation, liquid for internal use, capsule or the like. When the pharmaceutical product of the present invention is used for the applications of parenteral administration, the pharmaceutical product is preferably an injectable preparation, an ointment or a cream, but is not limited thereto. By using the pharmaceutical product of the present invention, a sustained release effect can be obtained as the α-lipoic acid nanoparticles slowly degrade in the body.

The pharmaceutical product of the present invention may be used for the same conventional applications as those of conventional pharmaceutical products containing α-lipoic acid as a main ingredient. Examples of the use and efficacy of the pharmaceutical product of the present invention include supplementation upon an increase in the demand of thioctic acid (at the time of vigorous physical labor), Leigh syndrome (subacute necrotic encephalomyelitis), and toxic (due to streptomycin or kanamycin) and noise-induced (occupational) inner ear hearing impairment. Also, the pharmaceutical product of the present invention may be an infusion preparation or an injectable preparation for the detoxification of heavy metals. The pharmaceutical product of the present invention may also be a pharmaceutical product for oral administration intended for the treatment of diabetes.

Adding of the α-lipoic acid nanoparticles synthesized by the method of the present invention, into a pharmaceutical product, does not require any special process, and the α-lipoic acid nanoparticles are added together with the raw materials in the early stage of the production process of the pharmaceutical product, or added in the middle of the production process, or added at the final stage of the production process. In regard to the mode of addition, conventional methods such as mixing, kneading, dissolution, immersion, spreading, spraying and applying, are selected in accordance with the kind and properties of the pharmaceutical product. The pharmaceutical product of the present invention can be prepared according to the methods that are known to those skilled in the art.

When the content of the α-lipoic acid nanoparticles contained in the pharmaceutical product of the present invention is converted to α-lipoic acid, the content is preferably about 0.01% by weight or more, more preferably about 0.05% by weight or more, even more preferably about 0.1% by weight or more, particularly preferably about 0.5% by weight or more, and most preferably about 1.0% by weight or more. When the content of the α-lipoic acid nanoparticles contained in the pharmaceutical product of the present invention is converted to α-lipoic acid, the content is preferably about 10% by weight or less, more preferably about 8% by weight or less, even more preferably about 5% by weight or less, particularly preferably about 4% by weight or less, and most preferably about 3% by weight or less.

EXAMPLES

In the following Examples and Comparative Examples, the following substances were used as the reagents:

α-Lipoic acid: α-lipoic acid, special grade, manufactured by Wako Pure Chemical Industries, Ltd. (purity 98% or higher, powder form);

Sucrose lauric acid ester: Ryoto Sugar Ester L-1695 (HLB value about 15; linked fatty acid about 99%; monoester about 80%; di-, tri-, and poly-ester about 20%) manufactured by Mitsubishi-Kagaku Foods Corporation;

Polyoxyethylene (60) hydrogenated castor oil: NIKKOL HCO-60 (HLB about 14; paste to solid, white to pale yellow in color) manufactured by Nikko Chemicals Co., Ltd.;

Polyoxyethylene octyl dodecyl ether: EMULGEN 2020G-HA (HLB value 13.0) manufactured by Kao Corporation;

POE (20) POP (8) cetyl ether: NIKKOL PBC44 (HLB about 12.5; solid, white to pale yellow in color) manufactured by Nikko Chemicals Co., Ltd.;

POE (20) stearyl ether: NIKKOL BS-20 (HLB 18.0; solid, white to pale yellow in color) manufactured by Nikko Chemicals Co., Ltd.;

Polyoxyethylene (20) sorbitan monooleic acid ester: Polysorbate (80) (HLB about 15; colorless transparent liquid) manufactured by NOF Corp.;

$MgCl_2$: commercially available product, reagent grade;

$CaCl_2$: commercially available product, reagent grade;

Zinc gluconate: commercially available product, reagent grade;

$Na_2CO_3$: commercially available product, reagent grade; and $Na_2HPO_4$: commercially available product, reagent grade.

Example 1

Production of α-Lipoic Acid-$MgCO_3$ Nanoparticles

Example 1A 0.5 g of α-lipoic acid was added to 9 mL of ion-exchanged water and mixed, and 5M NaOH was added to this mixed liquid to adjust the pH of the mixed liquid to 7.2. When the pH reached 7.2, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of Ryoto Sugar Ester L-1695, and stirred satisfactorily. Stirring was carried out for about 30 minutes, and then 20 μL of 0.5 M $MgCl_2$ was added to the resulting solution and stirred. Stirring was carried out for 30 minutes, and then 20 μL of 0.1M $Na_2CO_3$ was added to this solution, and then further stirred. Thereby, a transparent dispersion liquid containing α-lipoic acid-$MgCO_3$ nanoparticles was obtained. This transparent dispersion liquid was stirred for a whole day (24 hours), and then the dispersion liquid was freeze-dried overnight to obtain a paste. When these α-lipoic acid-$MgCO_3$ nanoparticles were to be used in other tests, the paste after freeze-drying was redispersed in distilled water to a predetermined concentration before use. This paste after freeze-drying was added to distilled water, satisfactorily redispersed, and thereby, a transparent dispersion liquid was obtained. This indicates that the α-lipoic acid-$MgCO_3$ nanoparticles are stable after freeze-drying.

Example 1B

A paste containing α-lipoic acid-$MgCO_3$ nanoparticles was obtained by the same procedure as that in Example 1A, except that the same amount of distilled water was used instead of the ion-exchanged water for the preparation of the stock solution. When these α-lipoic acid-$MgCO_3$ nanoparticles were to be used in other tests, the paste after freeze-drying was redispersed in distilled water to a predetermined concentration before use. This paste after freeze-drying was added to distilled water. This paste was satisfactorily redispersed, and thereby a transparent dispersion liquid was obtained. This indicates that the α-lipoic acid-$MgCO_3$ nanoparticles are stable after freeze-drying.

Example 2

Production of α-Lipoic Acid-$MgCO_3$ Nanoparticles

Example 2A 0.25 g of α-lipoic acid was added to 9 mL of ion-exchanged water and mixed, and 5M NaOH was added to this mixed liquid to adjust the pH of the mixed liquid to 7.1. When the pH reached 7.1, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of Ryoto Sugar Ester L-1695, and stirred satisfactorily. Stirring was carried out for about 30 minutes, and then 20 μL of 0.5 M $MgCl_2$ was added to the resulting solution and stirred. Stirring was carried out for 30 minutes, and then 20 μL of 0.1M $Na_2CO_3$ was added to this solution, and then further stirred. Thereby, a transparent dispersion liquid containing α-lipoic acid-$MgCO_3$ nanoparticles was obtained. This transparent dispersion liquid was stirred for a whole day (24 hours), and then the dispersion liquid was freeze-dried overnight to obtain a paste. When these α-lipoic acid-$MgCO_3$ nanoparticles were to be used in other tests, the paste after freeze-drying was redispersed in distilled water to a predetermined concentration before use. This paste after freeze-drying was added to distilled water, satisfactorily redispersed, and thereby, a transparent dispersion liquid was obtained. This indicates that the α-lipoic acid-$MgCO_3$ nanoparticles are stable after freeze-drying.

Example 2B

A paste containing α-lipoic acid-$MgCO_3$ nanoparticles was obtained by the same procedure as that in Example 2A, except that the same amount of distilled water was used instead of the ion-exchanged water for the preparation of the stock solution. When these α-lipoic acid-$MgCO_3$ nanoparticles were to be used in other tests, the paste after freeze-drying was redispersed in distilled water to a predetermined concentration before use. This paste after freeze-drying was added to distilled water. This paste was satisfactorily redispersed, and thereby a transparent dispersion liquid was obtained. This indicates that the α-lipoic acid-$MgCO_3$ nanoparticles are stable after freeze-drying.

Comparative Example 1

Production of α-Lipoic Acid Dispersion Liquid

Comparative Example 1A 0.5 g of α-lipoic acid was added to 9 mL of ion-exchanged water and mixed, and 5M NaOH was added to this mixed liquid to adjust the pH of the mixed liquid to 7.2. When the pH reached about 7.2, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of Ryoto Sugar Ester L-1695, and stirred satisfactorily. This dispersion liquid was stirred for a whole day (24 hours), and then the dispersion liquid was freeze-dried overnight to obtain a paste.

Comparative Example 1B

A paste was obtained by the same procedure as that in Comparative Example 1A, except that the same amount of distilled water was used instead of the ion-exchanged water for the preparation of the stock solution.

Measurement Example 1

Figure 2:
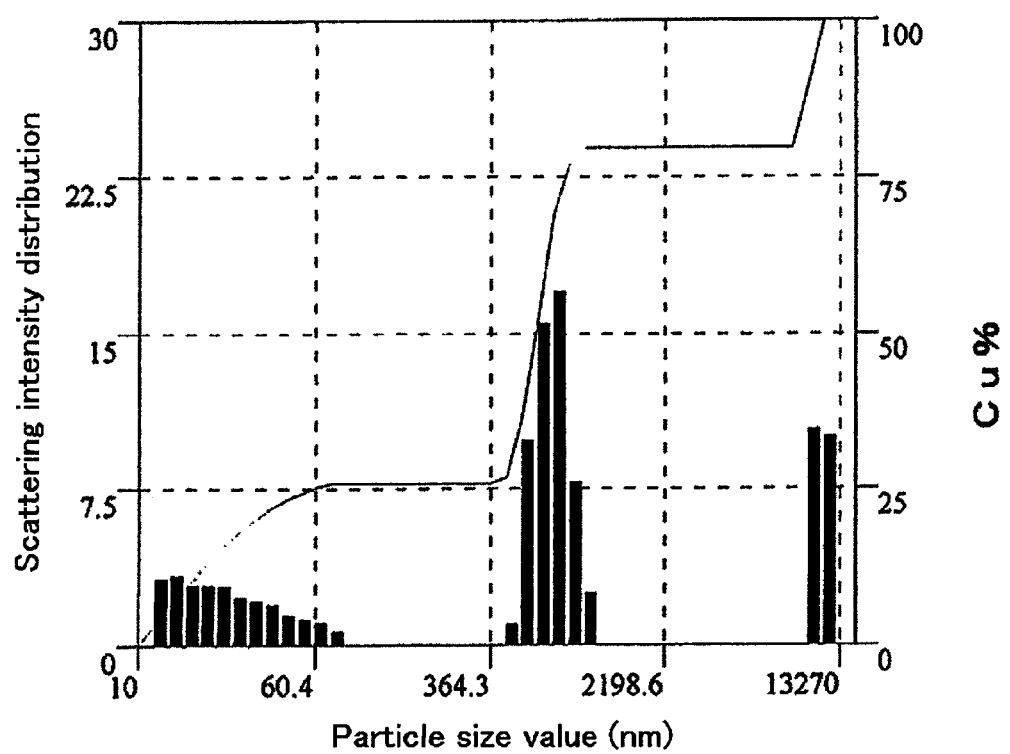
FIG. 2 shows the result of the particle size distribution of the α-lipoic acid nanoparticles produced by using ion-exchanged water in Comparative Example 1A, measured by using a light scattering photometer (Otsuka Electronics Co., Ltd., ELS-710TY).

Measurement of Particle Size 0.3 g of each of the paste of α-lipoic acid-$MgCO_3$ nanoparticles produced and used in Example 1A and the paste of α-lipoic acid nanoparticles of Comparative Example 1A produced without adding magnesium chloride and sodium carbonate were respectively added to 3 mL of water, left to stand at 4° C. for about 3 hours, and then stirred for one minute to disperse. The particle sizes were measured using a light scattering photometer (Otsuka Electronics Co., Ltd., ELS-710 TY). As a result, it was confirmed that the particle size of the α-lipoic acid-$MgCO_3$ nanoparticles produced in Example 1A was about 10 nm, and the particle size of the α-lipoic acid nanoparticles of Comparative Example 1A produced without adding magnesium chloride and sodium carbonate was about 760 nm. The particle sizes when distilled water was used and when ion-exchanged water was used were almost the same. The results obtained by using Otsuka Electronics Co., Ltd., ELS-710TY for measuring the particle size distribution of the α-lipoic acid-$MgCO_3$ nanoparticles produced by using distilled water in Example 1A is shown in FIG. 1, and the results obtained by using a light scattering photometer (Otsuka Electronics Co., Ltd., ELS-710TY) for measuring the particle size distribution of the α-lipoic acid nanoparticles produced by using distilled water in Comparative Example 1A is presented in FIG. 2.

Example 3

Production of α-Lipoic Acid-$MgCO_3$ Nanoparticles

Example 3A 0.5 g of α-lipoic acid was added to 9 mL of ion-exchanged water and mixed, and 5M NaOH was added to this mixed liquid to adjust the pH of the mixed liquid to 7.0. When the pH reached 7.0, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then 20 μL of 0.5 M $MgCl_2$ was added to the resulting solution and stirred. Stirring was carried out for 30 minutes, and then 20 μL of 0.1M $Na_2CO_3$ was added to this solution, and then further stirred. Thereby, a transparent dispersion liquid containing α-lipoic acid-$MgCO_3$ nanoparticles was obtained.

Example 3B

A transparent dispersion liquid containing α-lipoic acid-$MgCO_3$ nanoparticles was obtained by the same procedure as that in Example 3A, except that the same amount of distilled water was used instead of the ion-exchanged water for the preparation of the stock solution.

Example 4

Production of α-Lipoic Acid-$MgCO_3$ Nanoparticles

Example 4A 0.5 g of α-lipoic acid was added to 9 mL of ion-exchanged water and mixed, and 5M NaOH was added to this mixed liquid to adjust the pH of the mixed liquid to 7.3. When the pH reached 7.3, the powder of α-lipoic acid disappeared, and a transparent appearance such as in a solution was obtained. Ion-exchanged water was added to this solution to result in a volume of 10 mL. This solution was used as a stock solution, and an aliquot of 50 μL was collected. This was added to 0.95 mL of distilled water containing 0.02 g of EMULGEN 2020G-HA, and stirred satisfactorily. Stirring was carried out for about 30 minutes, and then 10 μL of 0.5 M $MgCl_2$ was added to the solution and stirred. Stirring was carried out for 30 minutes, and then 5 μL of 0.1M $Na_2CO_3$ was added to this solution, and then further stirred. Thereby, a transparent dispersion liquid containing α-lipoic acid-$MgCO_3$ nanoparticles was obtained.

Example 4B

A transparent dispersion liquid containing α-lipoic acid-$MgCO_3$ nanoparticles was obtained by the same procedure as that in Example 4A, except that the same amount of distilled water was used instead of the ion-exchanged water for the preparation of the stock solution.

Example 5

Production of α-Lipoic Acid-$CaCO_3$ Nanoparticles

Example 5A 0.5 g of α-lipoic acid was added to 9 mL of ion-exchanged water and mixed, and 5M NaOH was added to this mixed liquid to adjust the pH of the mixed liquid to 7.1. When the pH reached 7.1, the powder of α-lipoic acid disappeared, and a transparent appearance such as in a solution was obtained. Ion-exchanged water was added to this solution to result in a volume of 10 mL. This solution was used as a stock solution, and an aliquot of 50 μL was collected. This was added to 0.95 mL of distilled water containing 0.05 g of HCO-60, and stirred satisfactorily. Stirring was carried out for about 30 minutes, then the pH of the solution was adjusted with 0.1M HCl or 0.1M NaOH to 6.6, and then 10 μL of 0.5M $CaCl_2$ was added and stirred. Stirring was carried out for about 30 minutes, 10 μL of 0.1M $Na_2CO_3$ was added to this solution, and then further stirred. Thereby, a transparent dispersion liquid containing α-lipoic acid-$CaCO_3$ nanoparticles was obtained. This transparent dispersion liquid was stirred for a whole day (24 hours), and then the dispersion liquid was freeze-dried overnight to obtain a paste.

Example 5B

A paste containing α-lipoic acid-$CaCO_3$ nanoparticles was obtained by the same procedure as that in Example 5A, except that the same amount of distilled water was used instead of the ion-exchanged water for the preparation of the stock solution.

Example 6

Production of α-Lipoic Acid-CaCO₃ Nanoparticles

Example 6A 0.5 g of α-lipoic acid was added to 9 mL of ion-exchanged water and mixed, and 5M NaOH was added to this mixed liquid to adjust the pH of the mixed liquid to 7.0. When the pH reached 7.0, the powder of α-lipoic acid disappeared, and a transparent appearance such as in a solution was obtained. Ion-exchanged water was added to this solution to result in a volume of 10 mL. This solution was used as a stock solution, and an aliquot of 20 µL was collected. This was added to 0.98 mL of distilled water containing 0.02 g of EMULGEN 2020G-HA, and stirred satisfactorily. Stirring was carried out for about 30 minutes, then the pH of the solution was adjusted with 0.1M HCl or 0.1M NaOH to 6.2, and then 5 µL of 0.5M CaCl₂ was added and stirred. Stirring was carried out for 30 minutes, and then 5 µL of 0.1M Na₂CO₃ was added to this solution, and then further stirred. Thereby, a transparent dispersion liquid containing α-lipoic acid-CaCO₃ nanoparticles was obtained.

Example 6B

A transparent dispersion liquid containing α-lipoic acid-CaCO₃ nanoparticles was obtained by the same procedure as that in Example 6A, except that the same amount of distilled water was used instead of the ion-exchanged water for the preparation of the stock solution.

Example 7

Production of α-Lipoic Acid-CaPO₄ Nanoparticles

Example 7A 0.5 g of α-lipoic acid was added to 9 mL of ion-exchanged water and mixed, and 5M NaOH was added to this mixed liquid to adjust the pH of the mixed liquid to 6.9. When the pH reached 6.9, the powder of α-lipoic acid disappeared, and a transparent appearance such as in a solution was obtained. Ion-exchanged water was added to this solution to result in a volume of 10 mL. This solution was used as a stock solution, and an aliquot of 20 µL was collected. This was added to 0.98 mL of distilled water containing 0.02 g of HCO-60, and stirred satisfactorily. Stirring was carried out for about 30 minutes, then the pH of the solution was adjusted with 0.1M HCl or 0.1M NaOH to 6.4, and then 5 µL of 0.5M CaCl₂ was added and stirred. Stirring was carried out for 30 minutes, 5 µL of 0.1M Na₂HPO₄ was added to this solution, and then further stirred. Thereby, a transparent dispersion liquid containing α-lipoic acid-CaPO₄ nanoparticles was obtained. This transparent dispersion liquid was stirred for a whole day (24 hours), and then the dispersion liquid was freeze-dried overnight to obtain a paste.

Example 7B

A paste containing α-lipoic acid-CaPO₄ nanoparticles was obtained by the same procedure as that in Example 7A, except that the same amount of distilled water was used instead of the ion-exchanged water for the preparation of the stock solution.

Example 8

Production of α-Lipoic Acid-CaCO₃ Nanoparticles

Example 8A 0.5 g of α-lipoic acid was added to 9 mL of ion-exchanged water and mixed, and 1M NaOH was added to this mixed liquid to adjust the pH of the mixed liquid to 11.7. When the pH reached 11.7, the powder of α-lipoic acid disappeared, and a transparent appearance such as in a solution was obtained. Ion-exchanged water was added to this solution to result in a volume of 10 mL. This solution was used as a stock solution, and an aliquot of 100 µL was collected. This was added to 0.9 mL of distilled water containing 0.1 g of POE (20)POP (8) cetyl ether (PBC44), and stirred satisfactorily. Stirring was carried out for about 30 minutes, then the pH of the solution was adjusted with 0.1M HCl or 0.1M NaOH to 11.0, and then 40 µL of 0.5M CaCl₂ was added and stirred. Stirring was carried out for 30 minutes, and then 4 µL of 0.1M Na₂CO₃ was added to this solution, and then further stirred. Thereby, a transparent dispersion liquid containing α-lipoic acid-CaCO₃ nanoparticles was obtained.

Example 8B

A transparent dispersion liquid containing α-lipoic acid-CaCO₃ nanoparticles was obtained by the same procedure as that in Example 8A, except that the same amount of distilled water was used instead of the ion-exchanged water for the preparation of the stock solution.

Example 9

Production of α-Lipoic Acid-CaCO₃ Nanoparticles

Example 9A 0.5 g of α-lipoic acid was added to 9 mL of ion-exchanged water and mixed, and 1M NaOH was added to this mixed liquid to adjust the pH of the mixed liquid to 11.5. When the pH reached 11.5, the powder of α-lipoic acid disappeared, and a transparent appearance such as in a solution was obtained. Ion-exchanged water was added to this solution to result in a volume of 10 mL. This solution was used as a stock solution, and an aliquot of 100 µL was collected. This was added to 0.9 mL of distilled water containing 0.02 g of POE (20) stearyl ether, and stirred satisfactorily. Stirring was carried out for about 30 minutes, then the pH of the solution was adjusted with 0.1M HCl or 0.1M NaOH to 10.8, and then 40 µL of 0.5M CaCl₂ was added and stirred. Stirring was carried out for 30 minutes, and then 4 µL of 0.1M Na₂CO₃ was added to this solution, and then further stirred. Thereby, a transparent dispersion liquid containing α-lipoic acid-CaCO₃ nanoparticles was obtained.

Example 9B

A transparent dispersion liquid containing α-lipoic acid-CaCO₃ nanoparticles was obtained by the same procedure as that in Example 9A, except that the same amount of distilled water was used instead of the ion-exchanged water for the preparation of the stock solution.

Example 10

Production of α-Lipoic Acid-ZnCO$_3$ Nanoparticles

Example 10A 0.5 g of α-lipoic acid was added to 9 mL of ion-exchanged water and mixed, and 5M NaOH was added to this mixed liquid to adjust the pH of the mixed liquid to 6.8. When the pH reached 6.8, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then the pH of the solution was adjusted to 5.0 with 0.1M HCl, and then 20 μL of 5% zinc gluconate solution was added and stirred. Stirring was carried out for 30 minutes, and then 20 μL of 0.1M Na$_2$CO$_3$ was added to this solution, and then further stirred. Thereby, a transparent dispersion liquid containing α-lipoic acid-ZnCO$_3$ nanoparticles was obtained.

Example 10B

A transparent dispersion liquid containing α-lipoic acid-ZnCO$_3$ nanoparticles was obtained by the same procedure as that in Example 10A, except that the same amount of distilled water was used instead of the ion-exchanged water for the preparation of the stock solution.

Example 11

Production of α-Lipoic Acid-ZnCO$_3$ Nanoparticles

Example 11A 0.5 g of α-lipoic acid was added to 9 mL of ion-exchanged water and mixed, and 5M NaOH was added to this mixed liquid to adjust the pH of the mixed liquid to 6.9. When the pH reached 6.9, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then the pH of the solution was adjusted to 5.0 with 0.1M HCl, and then 20 μL of 0.5M zinc acetate solution was added and stirred. Stirring was carried out for 30 minutes, and then 20 μL of 0.1M Na$_2$CO$_3$ was added to this solution, and then further stirred. Thereby, a transparent dispersion liquid containing α-lipoic acid-ZnCO$_3$ nanoparticles was obtained.

Example 11B

A transparent dispersion liquid containing α-lipoic acid-ZnCO$_3$ nanoparticles was obtained by the same procedure as that in Example 11A, except that the same amount of distilled water was used instead of the ion-exchanged water for the preparation of the stock solution.

Example 12

Production of α-Lipoic Acid-MgCO$_3$ Nanoparticles

Example 12A 0.5 g of α-lipoic acid was added to 9 mL of ion-exchanged water and mixed, and 5M NaOH was added to this mixed liquid to adjust the pH of the mixed liquid to 6.9. When the pH reached 6.9, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of Ryoto Sugar Ester L-1695, and stirred satisfactorily. Stirring was carried out for about 30 minutes, and then the pH of the solution was adjusted to 6.8 with 0.1M HCl, and then 40 μL of 0.5M magnesium chloride solution was added and stirred. Stirring was carried out for 30 minutes, and then 80 μL of 0.1M Na$_2$CO$_3$ was added to this solution, and then further stirred. Thereby, a transparent dispersion liquid containing α-lipoic acid-MgCO$_3$ nanoparticles was obtained.

Example 12B

A transparent dispersion liquid containing α-lipoic acid-MgCO$_3$ nanoparticles was obtained by the same procedure as that in Example 12A, except that the same amount of distilled water was used instead of the ion-exchanged water for the preparation of the stock solution.

Example 13

Production of α-Lipoic Acid-ZnCO$_3$ Nanoparticles

Example 13A 0.5 g of α-lipoic acid was added to 9 mL of ion-exchanged water and mixed, and 5M NaOH was added to this mixed liquid to adjust the pH of the mixed liquid to 6.9. When the pH reached 6.9, the powder of α-lipoic acid disappeared, and a transparent appearance such as in a solution was obtained. Ion-exchanged water was added to this solution to result in a volume of 10 mL. This solution was used as a stock solution, and an aliquot of 100 μl was collected. This was added to 0.9 mL of distilled water containing 0.1 g of HCO-60, and stirred satisfactorily. Stirring was carried out for about 30 minutes, and then the pH of the solution was adjusted to 3.9 with 0.1M HCl, and then 20 μL of 0.5M zinc acetate solution was added and stirred. Stirring was carried out for 30 minutes, and then 20 μL of 0.1M Na$_2$CO$_3$ was added to this solution, and then further stirred. Thereby, a transparent dispersion liquid containing α-lipoic acid-ZnCO$_3$ nanoparticles was obtained.

Example 13B

A transparent dispersion liquid containing α-lipoic acid-ZnCO$_3$ nanoparticles was obtained by the same procedure as that in Example 13A, except that the same amount of distilled water was used instead of the ion-exchanged water for the preparation of the stock solution.

Example 14

Production of α-Lipoic Acid-CaCO$_3$ Nanoparticles

Example 14A 0.5 g of α-lipoic acid was added to 9 mL of ion-exchanged water and mixed, and 5M NaOH was added to this mixed liquid to adjust the pH of the mixed liquid to 10.9. When the pH reached 10.9, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then the pH of the solution was adjusted to 6.4 with 0.1M HCl, and then 40 μL of 0.5M calcium chloride solution was added and stirred. Stirring was carried out for 30 minutes, and then 40 μL of 0.1M $Na_2CO_3$ was added to this solution, and then further stirred. Thereby, a transparent dispersion liquid containing α-lipoic acid-$CaCO_3$ nanoparticles was obtained.

Example 14B

A transparent dispersion liquid containing α-lipoic acid-$CaCO_3$ nanoparticles was obtained by the same procedure as that in Example 14A, except that the same amount of distilled water was used instead of the ion-exchanged water for the preparation of the stock solution.

Example 15

Production of α-Lipoic Acid-$CaCO_3$ Nanoparticles

Example 15A 0.5 g of α-lipoic acid was added to 9 mL of ion-exchanged water and mixed, and 5M NaOH was added to this mixed liquid to adjust the pH of the mixed liquid to 8.7. When the pH reached 8.7, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then the pH of the solution was adjusted to 6.3 with 0.1M HCl, and then 40 μL of 0.5M calcium chloride solution was added and stirred. Stirring was carried out for 30 minutes, and then 40 μL of 0.1M $Na_2CO_3$ was added to this solution, and then further stirred. Thereby, a transparent dispersion liquid containing α-lipoic acid-$CaCO_3$ nanoparticles was obtained.

Example 15B

A transparent dispersion liquid containing α-lipoic acid-$CaCO_3$ nanoparticles was obtained by the same procedure as that in Example 15A, except that the same amount of distilled water was used instead of the ion-exchanged water for the preparation of the stock solution.

Example 16

Production of α-Lipoic Acid-$CaCO_3$ Nanoparticles

Example 16A 0.5 g of α-lipoic acid was added to 9 mL of ion-exchanged water and mixed, and 5M NaOH was added to this mixed liquid to adjust the pH of the mixed liquid to 6.9. When the pH reached 6.9, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then the pH of the solution was adjusted to 6.4 with 0.1M HCl, and then 20 μL of 0.5M calcium chloride solution was added and stirred. Stirring was carried out for 30 minutes, and then 40 μL of 0.1M $Na_2CO_3$ was added to this solution, and then further stirred. Thereby, a transparent dispersion liquid containing α-lipoic acid-$CaCO_3$ nanoparticles was obtained.

Example 16B

A transparent dispersion liquid containing α-lipoic acid-$CaCO_3$ nanoparticles was obtained by the same procedure as that in Example 16A, except that the same amount of distilled water was used instead of the ion-exchanged water for the preparation of the stock solution.

Example 17

Production of α-Lipoic Acid-$CaCO_3$ Nanoparticles

Example 17A 0.5 g of α-lipoic acid was added to 9 mL of ion-exchanged water and mixed, and 5M NaOH was added to this mixed liquid to adjust the pH of the mixed liquid to 6.9. When the pH reached 6.9, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of EMULGEN 2020G-HA, and stirred satisfactorily. Stirring was carried out for about 30 minutes, and then the pH of the solution was adjusted to 6.7 with 0.1M HCl, and then 20 μL of 0.5M calcium chloride solution was added and stirred. Stirring was carried out for 30 minutes, and then 40 μL of 0.1M $Na_2CO_3$ was added to this solution, and then further stirred. Thereby, a transparent dispersion liquid containing α-lipoic acid-$CaCO_3$ nanoparticles was obtained.

Example 17B

A transparent dispersion liquid containing α-lipoic acid-$CaCO_3$ nanoparticles was obtained by the same procedure as that in Example 17A, except that the same amount of distilled water was used instead of the ion-exchanged water for the preparation of the stock solution.

Example 18

Production of α-Lipoic Acid-$CaCO_3$ Nanoparticles

Example 18A 0.5 g of α-lipoic acid was added to 9 mL of ion-exchanged water and mixed, and 5M NaOH was added to this mixed liquid to adjust the pH of the mixed liquid to 11.8. When the pH reached 11.8, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of HCO-60, and stirred satisfactorily. Stirring was carried out for about 30 minutes, and then the pH of the solution was adjusted to 10.9 with 0.1M HCl, and then 20 μL of 0.5M $CaCl_2$ was added and stirred. Stirring was carried out for 30 minutes, and then 20 μL of 0.1M $Na_2CO_3$ was added to this solution, and then further stirred. Thereby, a transparent dispersion liquid containing α-lipoic acid-CaCO$_3$ nanoparticles was obtained.

Example 18B

A transparent dispersion liquid containing α-lipoic acid-CaCO$_3$ nanoparticles was obtained by the same procedure as that in Example 18A, except that the same amount of distilled water was used instead of the ion-exchanged water for the preparation of the stock solution.

Example 19

Production of α-Lipoic Acid-MgCO$_3$ Nanoparticles

Example 19A 0.5 g of α-lipoic acid was added to 9 mL of ion-exchanged water and mixed, and 5M NaOH was added to this mixed liquid to adjust the pH of the mixed liquid to 9.1. When the pH reached 9.1, the powder of α-lipoic acid disappeared, and a transparent appearance such as in a solution was obtained. Ion-exchanged water was added to this solution to result in a volume of 10 mL. This solution was used as a stock solution, and an aliquot of 100 μL was collected. This was added to 0.9 mL of distilled water containing 0.1 g of Ryoto Sugar Ester L-1695, and stirred satisfactorily. Stirring was carried out for about 30 minutes, and then the pH of the solution was adjusted to 8.5 with 0.1M HCl, and then 20 μL of 0.5M MgCl$_2$ solution was added and stirred. Stirring was carried out for 30 minutes, and then 20 μL of 0.1M Na$_2$CO$_3$ was added to this solution, and then further stirred. Thereby, a transparent dispersion liquid containing α-lipoic acid-MgCO$_3$ nanoparticles was obtained.

Example 19B

A transparent dispersion liquid containing α-lipoic acid-MgCO$_3$ nanoparticles was obtained by the same procedure as that in Example 19A, except that the same amount of distilled water was used instead of the ion-exchanged water for the preparation of the stock solution.

Example 20

Production of α-Lipoic Acid-MgCO$_3$ Nanoparticles

Example 20A 0.28 g of 1M NaOH was added to 0.05 g of α-lipoic acid, mixed and stirred until it was completely dissolved. To this, 9.328 ml of water for injection (Japan Parmacopeia water for injection manufactured by Otsuka Pharmaceutical Co., Ltd.) was added and mixed. To this mixed liquid, 0.3 g of POE (20) stearyl ether was added and stirred for 30 minutes or longer, and then the pH of the solution was adjusted to 7.0 with 5N HCl. To this, 40 μL of 2.5M MgCl$_2$ was added and stirred satisfactorily, and then 2 μL of 1M Na$_2$CO$_3$ was added and further stirred, and water for injection was added to result in a volume of 10 mL. Thereby, a transparent dispersion liquid containing α-lipoic acid-MgCO$_3$ nanoparticles was obtained.

Example 20B

A transparent dispersion liquid containing α-lipoic acid-MgCO$_3$ nanoparticles was obtained by the same procedure as that in Example 20A, except that ion-exchanged water was used instead of the water for injection.

Example 21

Production of α-Lipoic Acid-MgCO$_3$ Nanoparticles

Example 21A

950 μL of 0.26M NaOH was added to 0.05 g of α-lipoic acid, mixed and stirred until it was completely dissolved. To this, 0.25 g of POE (20) stearyl ether was added and stirred satisfactorily, and then 3.626 mL of ion-exchanged water was added to this and stirred for 30 minutes or longer. pH of the solution was adjusted to 5.5 with 5N HCl. To this, 48 μL of 2.5M MgCl$_2$ was added and stirred satisfactorily, and then 48 μL of 1M Na$_2$CO$_3$ was added and further stirred, and ion-exchanged water was added to result in 5 mL. Thereby, a transparent dispersion liquid containing α-lipoic acid-MgCO$_3$ nanoparticles was obtained.

Example 21B

A transparent dispersion liquid containing α-lipoic acid-MgCO$_3$ nanoparticles was obtained by the same procedure as that in Example 21A, except that the same amount of distilled water was used instead of the ion-exchanged water.

Comparative Example 22-1

Production of α-Lipoic Acid Dispersion Liquid

Comparative Example 22-1A

To 4.0 g of polyoxyethylene hydrogenated castor oil (HCO-60) which has been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 6.8 with 5M NaOH, and then distilled water was further added to result in a volume of 50 ml. Thereby, an α-lipoic acid dispersion liquid was obtained.

Comparative Example 22-1B

An α-lipoic acid dispersion liquid was obtained by the same procedure as that in Comparative Example 22-1A, except that the same amount of ion-exchanged water was used instead of the distilled water.

Comparative Example 22-2

Production of α-Lipoic Acid Dispersion Liquid

Comparative Example 22-2A

To 5.0 g of polyoxyethylene hydrogenated castor oil (HCO-60) which has been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 7.0 with 5M NaOH, and then ion-exchanged water was further added to result in a volume of 50 ml. Thereby, an α-lipoic acid dispersion liquid was obtained.

Comparative Example 22-2B

An α-lipoic acid dispersion liquid was obtained by the same procedure as that in Comparative Example 22-2A, except that the same amount of distilled water was used instead of the ion-exchanged water.

Example 22

Production of α-Lipoic Acid-CaCO$_3$ Nanoparticles

Example 22A

To 4.0 g of polyoxyethylene hydrogenated castor oil (HCO-60) which has been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.6 with 5M NaOH. To this, 0.48 ml of 5 M CaCl$_2$ aqueous solution was added and mixed, and then 0.96 ml of 1 M Na$_2$CO$_3$ aqueous solution was added and further mixed. The pH of this solution was measured and adjusted to pH 6.7 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 22B

A transparent dispersion liquid containing α-lipoic acid-CaCO$_3$ nanoparticles was obtained by the same procedure as that in Example 22A, except that the same amount of ion-exchanged water was used instead of the distilled water.

Example 23

Production of α-Lipoic Acid-MgCO$_3$ Nanoparticles

Example 23A

To 4.0 g of polyoxyethylene hydrogenated castor oil (HCO-60) which has been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.6 with 5M NaOH. To this, 0.96 ml of 2.5 M MgCl$_2$ aqueous solution was added and mixed, and then 0.96 ml of 1 M Na$_2$CO$_3$ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-MgCO$_3$ nanoparticles was obtained.

Example 23B

A transparent dispersion liquid containing α-lipoic acid-MgCO$_3$ nanoparticles was obtained by the same procedure as that in Example 23A, except that the same amount of distilled water was used instead of the ion-exchanged water.

Example 24

Production of α-Lipoic Acid-CaCO$_3$ Nanoparticles

Example 24A

To 4.0 g of polyoxyethylene hydrogenated castor oil (HCO-60) which has been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.3 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.7 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 24B

A transparent dispersion liquid containing α-lipoic acid-CaCO$_3$ nanoparticles was obtained by the same procedure as that in Example 24A, except that the same amount of ion-exchanged water was used instead of the distilled water.

Example 25

Production of α-Lipoic Acid-MgCO$_3$ Nanoparticles

Example 25a

To 3.5 g of polyoxyethylene hydrogenated castor oil (HCO-60) which has been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.5 with 5M NaOH. To this, 0.48 ml of 2.5M MgCl$_2$ aqueous solution was added and mixed, and then 0.24 ml of 1 M Na$_2$CO$_3$ aqueous solution was added and further mixed. The pH of this solution was measured and adjusted to pH 6.3 with 1M NaOH or 1M HCl. Distilled water was further added to result in a volume of 50 ml. Thereby, a transparent dispersion liquid containing α-lipoic acid-MgCO$_3$ nanoparticles was obtained.

Example 25B

A transparent dispersion liquid containing α-lipoic acid-MgCO$_3$ nanoparticles was obtained by the same procedure as that in Example 25A, except that the same amount of ion-exchanged water was used instead of the distilled water.

Example 26

Production of α-Lipoic Acid-CaCO$_3$ Nanoparticles

Example 26A

To 3.5 g of polyoxyethylene hydrogenated castor oil (HCO-60) which has been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.2 with 5M NaOH. To this, 0.24 ml of 5 M CaCl$_2$ aqueous solution was added and mixed, and then 0.72 ml of 1 M Na$_2$CO$_3$ aqueous solution was added and further mixed. The pH of this solution was measured and adjusted to pH 6.9 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 26B

A transparent dispersion liquid containing α-lipoic acid-CaCO$_3$ nanoparticles was obtained by the same procedure as that in Example 26A, except that the same amount of ion-exchanged water was used instead of the distilled water.

Example 27

Production of α-Lipoic Acid-CaCO$_3$ Nanoparticles

Example 27A

To 4.5 g of polyoxyethylene hydrogenated castor oil (HCO-60) which has been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.5 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-CaCO$_3$ nanoparticles was obtained.

Example 27B

A transparent dispersion liquid containing α-lipoic acid-CaCO$_3$ nanoparticles was obtained by the same procedure as that in Example 27A, except that the same amount of distilled water was used instead of the ion-exchanged water.

Example 28

Production of α-Lipoic Acid-MgCO$_3$ Nanoparticles

Example 28A

To 4.5 g of polyoxyethylene hydrogenated castor oil (HCO-60) which has been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.5 with 5M NaOH. To this, 0.48 ml of 2.5 M MgCl$_2$ aqueous solution was added and mixed, and then 0.48 ml of 1 M Na$_2$CO$_3$ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-MgCO$_3$ nanoparticles was obtained.

Example 28B

A transparent dispersion liquid containing α-lipoic acid-MgCO$_3$ nanoparticles was obtained by the same procedure as that in Example 28A, except that the same amount of distilled water was used instead of the ion-exchanged water.

Example 29

Production of α-Lipoic Acid-MgCO$_3$ Nanoparticles

Example 29A

To 5.0 g of polyoxyethylene hydrogenated castor oil (HCO-60) which has been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.6 with 5M NaOH. To this, 0.96 ml of 2.5 M MgCl$_2$ aqueous solution was added and mixed, and then 1.44 ml of 1 M Na$_2$CO$_3$ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-MgCO$_3$ nanoparticles was obtained.

Example 29B

A transparent dispersion liquid containing α-lipoic acid-MgCO$_3$ nanoparticles was obtained by the same procedure as that in Example 29A, except that the same amount of distilled water was used instead of the ion-exchanged water.

Example 30

Production of α-Lipoic Acid-CaCO$_3$ Nanoparticles

Example 30A

To 5.0 g of polyoxyethylene hydrogenated castor oil (HCO-60) which has been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.6 with 5M NaOH. To this, 0.48 ml of 5M CaCl$_2$ aqueous solution was added and mixed, and then 0.48 ml of 1 M Na$_2$CO$_3$ aqueous solution was added and further mixed. The pH of this solution was measured and adjusted to pH 6.6 with 1M NaOH or 1 M HCl. Ion-exchanged water was further added to result in a volume of 50 ml. Thereby, a transparent dispersion liquid containing α-lipoic acid-CaCO$_3$ nanoparticles was obtained.

Example 30B

A transparent dispersion liquid containing α-lipoic acid-CaCO$_3$ nanoparticles was obtained by the same procedure as that in Example 30A, except that the same amount of distilled water was used instead of the ion-exchanged water.

Example 31

Production of α-Lipoic Acid-CaCO$_3$ Nanoparticles

Example 31A

To 4.0 g of polyoxyethylene (20) stearyl ether which has been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.3 with 5M NaOH. To this, 0.24 ml of 5 M CaCl$_2$ aqueous solution was added and mixed, and then 0.48 ml of 1 M Na$_2$CO$_3$ aqueous solution was added and further mixed. The pH of this solution was measured and adjusted to pH 6.9 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 31B

A transparent dispersion liquid containing α-lipoic acid-CaCO$_3$ nanoparticles was obtained by the same procedure as that in Example 31A, except that the same amount of ion-exchanged water was used instead of the distilled water.

Example 32

Production of α-Lipoic Acid-CaCO₃ Nanoparticles

Example 32a

To 7.0 g of EMULGEN 2020G-HA which has been previously heated and melted, 1.0 g of an α-lipoic acid powder was added and mixed to dissolve the α-lipoic acid. About 70 ml of distilled water was added to this mixture and mixed for 30 minutes or longer. The pH was adjusted to 4.6 with 5M NaOH. To this, 0.24 ml of 5 M $CaCl_2$ aqueous solution was added and mixed, and then 0.24 ml of 1 M $Na_2CO_3$ aqueous solution was added and further mixed. The pH of this solution was measured and adjusted to pH 6.8 with 1M NaOH or 1 M HCl. Distilled water was further added to result in a volume of 50 ml. Thereby, a transparent dispersion liquid containing α-lipoic acid-CaCO₃ nanoparticles was obtained.

Example 32B

A transparent dispersion liquid containing α-lipoic acid-CaCO₃ nanoparticles was obtained by the same procedure as that in Example 32A, except that the same amount of ion-exchanged water was used instead of the distilled water.

Example 33

Production of α-Lipoic Acid-CaCO₃ Nanoparticles

Example 33A

To 7.0 g of Polysorbate (80) which has been previously heated and melted, 0.25 g of an α-lipoic acid powder was added and mixed to dissolve the α-lipoic acid. About 35 ml of distilled water was added to this mixture and mixed for 30 minutes or longer. The pH was adjusted to 4.3 with 5M NaOH. To this, 0.12 ml of 5 M $CaCl_2$ aqueous solution was added and mixed, and then 0.12 ml of 1 M $Na_2CO_3$ aqueous solution was added and further mixed. The pH of this solution was measured and adjusted to pH 6.5 with 1M NaOH or 1 M HCl. Distilled water was further added to result in a volume of 50 ml. Thereby, a transparent dispersion liquid containing α-lipoic acid-CaCO₃ nanoparticles was obtained.

Example 33B

A transparent dispersion liquid containing α-lipoic acid-CaCO₃ nanoparticles was obtained by the same procedure as that in Example 33A, except that the same amount of ion-exchanged water was used instead of the distilled water.

Example 34

Production of α-Lipoic Acid-MgCO₃ Nanoparticles

Example 34A

To 7.0 g of Polysorbate (80) which has been previously heated and melted, 0.25 g of an α-lipoic acid powder was added and mixed to dissolve the α-lipoic acid. About 35 ml of distilled water was added to this mixture and mixed for 30 minutes or longer. The pH was adjusted to 4.5 with 5M NaOH. To this, 0.24 ml of 2.5 M $MgCl_2$ aqueous solution was added and mixed, and then 0.12 ml of 1 M$Na_2CO_3$ aqueous solution was added and further mixed. The pH of this solution was measured and adjusted to pH 6.8 with 1M NaOH or 1 M HCl. Distilled water was further added to result in a volume of 50 ml. Thereby, a transparent dispersion liquid containing α-lipoic acid-MgCO₃ nanoparticles was obtained.

Example 34B

A transparent dispersion liquid containing α-lipoic acid-MgCO₃ nanoparticles was obtained by the same procedure as that in Example 34A, except that the same amount of ion-exchanged water was used instead of the distilled water.

Example 35

Production of α-Lipoic Acid-CaCO₃ Nanoparticles

Example 35A

To 7.0 g of Polysorbate (80) which has been previously heated and melted, 0.25 g of an α-lipoic acid powder was added and mixed to dissolve the α-lipoic acid. About 35 ml of distilled water was added to this mixture and mixed for 30 minutes or longer. The pH was adjusted to 4.3 with 5M NaOH. To this, 0.24 ml of 5 M $CaCl_2$ aqueous solution was added and mixed, and then 0.48 ml of 1 M$Na_2CO_3$ aqueous solution was added and further mixed. The pH of this solution was measured and adjusted to pH 6.5 with 1M NaOH or 1 M HCl. Distilled water was further added to result in a volume of 50 ml. Thereby, a transparent dispersion liquid containing α-lipoic acid-CaCO₃ nanoparticles was obtained.

Example 35B

A transparent dispersion liquid containing α-lipoic acid-CaCO₃ nanoparticles was obtained by the same procedure as that in Example 35A, except that the same amount of ion-exchanged water was used instead of the distilled water.

Example 36

Production of α-Lipoic Acid-MgCO₃ Nanoparticles

Example 36A

To 7.0 g of Polysorbate (80) which has been previously heated and melted, 0.25 g of an α-lipoic acid powder was added and mixed to dissolve the α-lipoic acid. About 35 ml of distilled water was added to this mixture and mixed for 30 minutes or longer. The pH was adjusted to 4.5 with 5M NaOH. To this, 0.48 ml of 2.5 M $MgCl_2$ aqueous solution was added and mixed, and then 0.48 ml of 1 M $Na_2CO_3$ aqueous solution was added and further mixed. The pH of this solution was measured and adjusted to pH 6.9 with 1M NaOH or 1 M HCl. Distilled water was further added to result in a volume of 50 ml. Thereby, a transparent dispersion liquid containing α-lipoic acid-MgCO₃ nanoparticles was obtained.

Example 36B

A transparent dispersion liquid containing α-lipoic acid-MgCO₃ nanoparticles was obtained by the same procedure as that in Example 36A, except that the same amount of ion-exchanged water was used instead of the distilled water.

Example 37

Production of α-Lipoic Acid-CaCO$_3$ Nanoparticles

Example 37A

To 4.0 g of polyoxyethylene (20) stearyl ether and 1.0 g of polyethylene glycol (1000) which have been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.5 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.6 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 37B

A transparent dispersion liquid containing α-lipoic acid-CaCO$_3$ nanoparticles was obtained by the same procedure as that in Example 37A, except that the same amount of ion-exchanged water was used instead of the distilled water.

Example 38

Production of α-Lipoic Acid-CaCO$_3$ Nanoparticles

Example 38A

To 4.0 g of polyoxyethylene (20) stearyl ether and 1.5 g of polyethylene glycol (4000) which have been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.3 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.8 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 38B

A transparent dispersion liquid containing α-lipoic acid-CaCO$_3$ nanoparticles was obtained by the same procedure as that in Example 38A, except that the same amount of ion-exchanged water was used instead of the distilled water.

Example 39

Production of α-Lipoic Acid-CaCO$_3$ Nanoparticles

Example 39A

To 4.0 g of polyoxyethylene (20) stearyl ether and 2.0 g of polyethylene glycol (4000) which have been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.5 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.5 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 39B

A transparent dispersion liquid containing α-lipoic acid-CaCO$_3$ nanoparticles was obtained by the same procedure as that in Example 39A, except that the same amount of ion-exchanged water was used instead of the distilled water.

Example 40

Production of α-Lipoic Acid-CaCO$_3$ Nanoparticles

Example 40A

To 4.0 g of polyoxyethylene (20) stearyl ether and 2.0 g of polyethylene glycol (1000) which have been previously heated and melted, 0.5 g of an α-lipoic acid powder was added and mixed to dissolve the α-lipoic acid. About 35 ml of distilled water was added to this mixture and mixed for 30 minutes or longer. The pH was adjusted to 4.4 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.9 with 1M NaOH or 1 M HCl. Distilled water was further added to result in a volume of 50 ml. Thereby, a transparent dispersion liquid containing α-lipoic acid-CaCO$_3$ nanoparticles was obtained.

Example 40B

A transparent dispersion liquid containing α-lipoic acid-CaCO$_3$ nanoparticles was obtained by the same procedure as that in Example 40A, except that the same amount of ion-exchanged water was used instead of the distilled water.

Example 41

Production of α-Lipoic Acid-MgCO$_3$ Nanoparticles

Example 41A

To 4.0 g of polyoxyethylene (20) stearyl ether and 1.5 g of polyethylene glycol (1000) which have been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.5 with 5M NaOH. To this, 0.48 ml of 2.5 M MgCl$_2$ aqueous solution was added and mixed, and then 0.24 ml of 1 MNa$_2$CO$_3$ aqueous solution was added and further mixed. The pH of this solution was measured and adjusted to pH 6.4 with 1M NaOH or 1 M HCl. Ion-exchanged water was further added to result in a volume of 50 ml. Thereby, a transparent dispersion liquid containing α-lipoic acid-MgCO$_3$ nanoparticles was obtained.

Example 41B

A transparent dispersion liquid containing α-lipoic acid-MgCO$_3$ nanoparticles was obtained by the same procedure as that in Example 41A, except that the same amount of distilled water was used instead of the ion-exchanged water.

Example 42

Production of α-Lipoic Acid-MgCO₃ Nanoparticles

Example 42A

To 4.0 g of polyoxyethylene (20) stearyl ether and 1.5 g of polyethylene glycol (4000) which have been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.6 with 5M NaOH. To this, 0.48 ml of 2.5 M MgCl₂ aqueous solution was added and mixed, and then 0.24 ml of 1 M Na₂CO₃ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-MgCO₃ nanoparticles was obtained.

Example 42B

A transparent dispersion liquid containing α-lipoic acid-MgCO₃ nanoparticles was obtained by the same procedure as that in Example 42A, except that the same amount of distilled water was used instead of the ion-exchanged water.

Example 43

Production of α-Lipoic Acid-MgCO₃ Nanoparticles

Example 43A

To 5.0 g of polyoxyethylene (20) stearyl ether and 1.5 g of polyethylene glycol (1000) which have been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.5 with 5M NaOH. To this, 0.48 ml of 2.5 M MgCl₂ aqueous solution was added and mixed, and then 0.48 ml of 1 M Na₂CO₃ aqueous solution was added and further mixed. The pH of this solution was measured and adjusted to pH 6.7 with 1M NaOH or 1 M HCl. Ion-exchanged water was further added to result in a volume of 50 ml. Thereby, a transparent dispersion liquid containing α-lipoic acid-MgCO₃ nanoparticles was obtained.

Example 43B

A transparent dispersion liquid containing α-lipoic acid-MgCO₃ nanoparticles was obtained by the same procedure as that in Example 43A, except that the same amount of distilled water was used instead of the ion-exchanged water.

Example 44

Production of α-Lipoic Acid-CaCO₃ Nanoparticles

Example 44A

To 5.0 g of polyoxyethylene (20) stearyl ether and 1.5 g of polyethylene glycol (1000) which have been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.6 with 5M NaOH. To this, 0.24 ml of 5 M CaCl₂ aqueous solution was added and mixed, and then 0.72 ml of 1 M Na₂CO₃ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-CaCO₃ nanoparticles was obtained.

Example 44B

A transparent dispersion liquid containing α-lipoic acid-CaCO₃ nanoparticles was obtained by the same procedure as that in Example 44A, except that the same amount of distilled water was used instead of the ion-exchanged water.

Example 45

Production of α-Lipoic Acid-MgCO₃ Nanoparticles

Example 45A

To 5.0 g of polyoxyethylene (20) stearyl ether and 1.5 g of polyethylene glycol (1000) which have been previously heated and melted, 0.5 g of an α-lipoic acid powder was added and mixed to dissolve the α-lipoic acid. About 35 ml of ion-exchanged water was added to this mixture and mixed for 30 minutes or longer. The pH was adjusted to 4.5 with 5M NaOH. To this, 0.48 ml of 2.5 M MgCl₂ aqueous solution was added and mixed, and then 0.72 ml of 1 M Na₂CO₃ aqueous solution was added and further mixed. The pH of this solution was measured and adjusted to pH 6.6 with 1M NaOH or 1 M HCl. Ion-exchanged water was further added to result in a volume of 50 ml. Thereby, a transparent dispersion liquid containing α-lipoic acid-MgCO₃ nanoparticles was obtained.

Example 45B

A transparent dispersion liquid containing α-lipoic acid-MgCO₃ nanoparticles was obtained by the same procedure as that in Example 45A, except that the same amount of distilled water was used instead of the ion-exchanged water.

Example 46

Production of α-Lipoic Acid-CaCO₃ Nanoparticles

Example 46A

To 5.0 g of polyoxyethylene (20) stearyl ether which has been previously heated and melted, 0.5 g of an α-lipoic acid powder was added and mixed to dissolve the α-lipoic acid. To this, 15 ml of polyethylene glycol (1000) solution, which was made by dissolving 10 g of polyethylene glycol (1000) in ion-exchanged water to result in 100 ml, was added and mixed. About 20 mL of ion-exchanged water was further added and mixed for 30 minutes or longer. The pH was adjusted to 4.5 with 5M NaOH. To this, 0.24 ml of 5 M CaCl₂ aqueous solution was added and mixed, and then 0.24 ml of 1 M Na₂CO₃ aqueous solution was added and further mixed. The pH of this solution was measured and adjusted to pH 6.7 with 1M NaOH or 1 M HCl. Ion-exchanged water was further added to result in a volume of 50 ml. Thereby, a transparent dispersion liquid containing α-lipoic acid-CaCO$_3$ nanoparticles was obtained.

Example 46B

A transparent dispersion liquid containing α-lipoic acid-CaCO$_3$ nanoparticles was obtained by the same procedure as that in Example 46A, except that the same amount of distilled water was used instead of the ion-exchanged water.

Example 47

Production of α-Lipoic Acid-CaCO$_3$ Nanoparticles

Example 47A

To 5.0 g of polyoxyethylene (20) stearyl ether which has been previously heated and melted, 0.5 g of an α-lipoic acid powder was added and mixed to dissolve the α-lipoic acid. To this, 15 ml of polyethylene glycol (4000) solution, which was made by dissolving 10 g of polyethylene glycol (4000) in ion-exchanged water to result in a volume of 100 ml, was added and mixed. About 20 ml of ion-exchanged water was further added and mixed for 30 minutes or longer. The pH was adjusted to 4.3 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.6 with 1M NaOH or 1 M HCl. Ion-exchanged water was further added to result in a volume of 50 ml. Thereby, a transparent dispersion liquid containing α-lipoic acid-CaCO$_3$ nanoparticles was obtained.

Example 47B

A transparent dispersion liquid containing α-lipoic acid-CaCO$_3$ nanoparticles was obtained by the same procedure as that in Example 47A, except that the same amount of distilled water was used instead of the ion-exchanged water.

Example 48

Production of α-Lipoic Acid-CaCO$_3$ Nanoparticles

Example 48A

To 5.0 g of polyoxyethylene (20) stearyl ether which has been previously heated and melted, 0.5 g of an α-lipoic acid powder was added and mixed to dissolve the α-lipoic acid. To this, 15 ml of polyethylene glycol (6000) solution, which was made by dissolving 10 g of polyethylene glycol (6000) in ion-exchanged water to result in a volume of 100 ml, was added and mixed. About 20 ml of ion-exchanged water was further added and mixed for 30 minutes or longer. The pH was adjusted to 4.4 with 5M NaOH. To this, 0.24 ml of 5 M CaCl$_2$ aqueous solution was added and mixed, and then 0.24 ml of 1 M Na$_2$CO$_3$ aqueous solution was added and further mixed. The pH of this solution was measured and adjusted to pH 6.8 with 1M NaOH or 1 M HCl. Ion-exchanged water was further added to result in a volume of 50 ml. Thereby, a transparent dispersion liquid containing α-lipoic acid-CaCO$_3$ nanoparticles was obtained.

Example 48B

A transparent dispersion liquid containing α-lipoic acid-CaCO$_3$ nanoparticles was obtained by the same procedure as that in Example 48A, except that the same amount of distilled water was used instead of the ion-exchanged water.

Example 49

Production of Highly Concentrated α-Lipoic Acid-MgCO$_3$ Nanoparticles

Example 49A 2.85 ml of 0.26M NaOH was added to 0.15 g of α-lipoic acid, mixed and stirred until it was completely dissolved. To this, 0.75 g of POE (20) stearyl ether was added and stirred satisfactorily, and then 0.5 ml of distilled water was added to this and stirred for 30 minutes or longer. The pH of the solution was adjusted to 5.5 with 5N HCl. To this, 144 µL of 2.5M MgCl$_2$ was added and stirred for 12 hours or longer, and then 144 µL of 1M Na$_2$CO$_3$ was added and stirred for further 12 hours or longer, and to this, distilled water was added to result in a volume of 5.0 ml. Thereby, a transparent dispersion liquid containing α-lipoic acid-MgCO$_3$ nanoparticles was obtained.

Example 49B

A transparent dispersion liquid containing α-lipoic acid-MgCO$_3$ nanoparticles was obtained by the same procedure as that in Example 49A, except that ion-exchanged water was used instead of the distilled water.

Example 50

Production of α-Lipoic Acid-MgCO$_3$ Nanoparticles

Example 50A 0.28 g of 1M NaOH was added to 0.05 g of α-lipoic acid, mixed and stirred until it was completely dissolved. To this, 9.35 ml of water for injection (Japan Parmacopeia water for injection manufactured by Otsuka Pharmaceutical Co., Ltd.) was added and mixed. To this mixed liquid, 0.3 g of polyoxyethylene hydrogenated castor oil (HCO-60) was added and stirred for 30 minutes or longer. Then, the pH of the solution was adjusted to 7.0 with 5N HCl. To this, 40 µL of 2.5M MgCl$_2$ was added and stirred satisfactorily, and then 20 µL of 1M Na$_2$CO$_3$ was added and further stirred, and water for injection was added to result in a volume of 10 mL. Thereby, a transparent dispersion liquid containing α-lipoic acid-MgCO$_3$ nanoparticles was obtained.

Example 50B

A transparent dispersion liquid containing α-lipoic acid-MgCO$_3$ nanoparticles was obtained by the same procedure as that in Example 50A, except that ion-exchanged water was used instead of the water for injection.

The results of these Examples 1A to 50B and Comparative Examples 1A, 1B, 22-1A to 22-2B are summarized in the following Table 1-1 to Table 1-3. It is noted that in Examples 1A to 21B and 49A to 50B, a procedure was used in which an α-lipoic acid-containing aqueous dispersion liquid is prepared and then a nonionic surfactant is added, and in Examples 22A to 48B, a procedure was used in which α-lipoic acid is dissolved in a nonionic surfactant and then water is added.

TABLE 1-1

Table of Examples and Comparative Examples (1)

| Example No. | pH of α-LP solution | Nonionic surfactant | Kind of surfactant | Adjusted pH | Divalent metal salt (A) | Salt carrying divalent anion (B) | A:B (molar ratio) |
|---|---|---|---|---|---|---|---|
| 1A, 1B | 7.2 | Ryoto Sugar Ester L-1695 | Sucrose fatty acid ester | — | $MgCl_2$ | $Na_2CO_3$ | 5:1 |
| Comparative Examples 1A, 1B | 7.2 | Ryoto Sugar Ester L-1695 | Sucrose fatty acid ester | — | — | — | — |
| 2A, 2B | 7.1 | Ryoto Sugar Ester L-1695 | Sucrose fatty acid ester | — | $MgCl_2$ | $Na_2CO_3$ | 5:1 |
| 3A, 3B | 7.0 | HCO-60 | Polyoxyethylene hydrogenated castor oil | — | $MgCl_2$ | $Na_2CO_3$ | 5:1 |
| 4A, 4B | 7.3 | EMULGEN 2020G-HA | Polyoxyethylene octyl dodecyl ether | — | $MgCl_2$ | $Na_2CO_3$ | 5:1 |
| 5A, 5B | 7.1 | HCO-60 | Polyoxyethylene hydrogenated castor oil | 6.6 | $CaCl_2$ | $Na_2CO_3$ | 5:1 |
| 6A, 6B | 7.0 | EMULGEN 2020G-HA | Polyoxyethylene octyl dodecyl ether | 6.2 | $CaCl_2$ | $Na_2CO_3$ | 5:1 |
| 7A, 7B | 6.9 | HCO-60 | Polyoxyethylene (60) hydrogenated castor oil | 6.4 | $CaCl_2$ | $Na_2HPO_4$ | 5:1 |
| 8A, 8B | 11.7 | PBC44 | POE (20) POP (8) cetyl ether | 11.0 | $CaCl_2$ | $Na_2CO_3$ | 50:1 |
| 9A, 9B | 11.5 | POE (20) stearyl ether | Polyoxyethylene alkyl ether | 10.8 | $CaCl_2$ | $Na_2CO_3$ | 50:1 |
| 10A, 10B | 6.8 | HCO-60 | Polyoxyethylene hydrogenated castor oil | 5.0 | Zinc gluconate | $Na_2CO_3$ | — |
| 11A, 11B | 6.9 | HCO-60 | Polyoxyethylene hydrogenated castor oil | 5.0 | $Zn(COOH)_2$ | $Na_2CO_3$ | 5:1 |
| 12A, 12B | 6.9 | Ryoto Sugar Ester L-1695 | Sucrose fatty acid ester | 6.8 | $MgCl_2$ | $Na_2CO_3$ | 5:2 |
| 13A, 13B | 6.9 | HCO-60 | Polyoxyethylene hydrogenated castor oil | 3.9 | $Zn(COOH)_2$ | $Na_2CO_3$ | 5:1 |
| 14A, 14B | 10.9 | HCO-60 | Polyoxyethylene hydrogenated castor oil | 6.4 | $CaCl_2$ | $Na_2CO_3$ | 5:1 |
| 15A, 15B | 8.7 | HCO-60 | Polyoxyethylene hydrogenated castor oil | 6.3 | $CaCl_2$ | $Na_2CO_3$ | 5:1 |
| 16A, 16B | 6.9 | HCO-60 | Polyoxyethylene hydrogenated castor oil | 6.4 | $CaCl_2$ | $Na_2CO_3$ | 5:2 |
| 17A, 17B | 6.9 | EMULGEN 2020G-HA | Polyoxyethylene octyl dodecyl ether | 6.7 | $CaCl_2$ | $Na_2CO_3$ | 5:2 |
| 18A, 18B | 11.8 | HCO-60 | Polyoxyethylene hydrogenated castor oil | 10.9 | $CaCl_2$ | $Na_2CO_3$ | 5:1 |
| 19A, 19B | 9.1 | Ryoto Sugar Ester L-1695 | Sucrose fatty acid ester | 8.5 | $MgCl_2$ | $Na_2CO_3$ | 5:1 |
| 20A, 20B | — | POE (20) stearyl ether | Polyoxyethylene alkyl ether | 7.0 | $MgCl_2$ | $Na_2CO_3$ | 50:1 |
| 21A, 21B | — | POE (20) stearyl ether | Polyoxyethylene alkyl ether | 5.5 | $MgCl_2$ | $Na_2CO_3$ | 5:2 |
| 49A, 49B | — | POE (20) stearyl ether | Polyoxyethylene alkyl ether | 5.5 | $MgCl_2$ | $Na_2CO_3$ | 5:2 |
| 50A, 50B | — | HCO-60 | Polyoxyethylene hydrogenated castor oil | 7.0 | $MgCl_2$ | $Na_2CO_3$ | 5:1 |

TABLE 1-2

Table of Examples and Comparative Examples (2)

| Example No. | pH before addition of metal ion | Nonionic surfactant | Kind of surfactant | Final pH | Divalent metal salt (A) | Salt carrying divalent anion (B) | A:B (molar ratio) |
|---|---|---|---|---|---|---|---|
| 22A, 22B | 4.6 | HCO-60 | Polyoxyethylene hydrogenated castor oil | 6.7 | $CaCl_2$ | $Na_2CO_3$ | 5:2 |
| Comparative Examples 22-1A, B | — | HCO-60 | Polyoxyethylene hydrogenated castor oil | 6.8 | — | — | — |
| Comparative Examples 22-2A, B | — | HCO-60 | Polyoxyethylene hydrogenated castor oil | 7.0 | — | — | — |
| 23A, 23B | 4.6 | HCO-60 | Polyoxyethylene hydrogenated castor oil | 6.8 | $MgCl_2$ | $Na_2CO_3$ | 5:2 |
| 24A, 24B | 4.3 | HCO-60 | Polyoxyethylene hydrogenated castor oil | 6.7 | $CaCl_2$ | $Na_2CO_3$ | 5:1 |
| 25A, 25B | 4.5 | HCO-60 | Polyoxyethylene hydrogenated castor oil | 6.3 | $MgCl_2$ | $Na_2CO_3$ | 5:1 |
| 26A, 26B | 4.2 | HCO-60 | Polyoxyethylene hydrogenated castor oil | 6.9 | $CaCl_2$ | $Na_2CO_3$ | 5:3 |
| 27A, 27B | 4.5 | HCO-60 | Polyoxyethylene hydrogenated castor oil | 6.8 | $CaCl_2$ | $Na_2CO_3$ | 5:1 |
| 28A, 28B | 4.5 | HCO-60 | Polyoxyethylene hydrogenated castor oil | 6.8 | $CaCl_2$ | $Na_2CO_3$ | 5:2 |
| 29A, 29B | 4.6 | HCO-60 | Polyoxyethylene hydrogenated castor oil | 6.8 | $MgCl_2$ | $Na_2CO_3$ | 5:3 |
| 30A, 30B | 4.6 | HCO-60 | Polyoxyethylene hydrogenated castor oil | 6.6 | $CaCl_2$ | $Na_2CO_3$ | 5:1 |
| 31A, 31B | 4.3 | POE (20) stearyl ether | Polyoxyethylene alkyl ether | 6.9 | $CaCl_2$ | $Na_2CO_3$ | 5:2 |
| 32A, 32B | 4.6 | EMULGEN 2020G-HA | Polyoxyethylene octyl dodecyl ether | 6.8 | $CaCl_2$ | $Na_2CO_3$ | 5:1 |
| 33A, 33B | 4.3 | Polysorbate 80 | Polyoxyethylene sorbitan fatty acid ester | 6.5 | $CaCl_2$ | $Na_2CO_3$ | 5:1 |
| 34A, 34B | 4.5 | Polysorbate 80 | Polyoxyethylene sorbitan fatty acid ester | 6.8 | $MgCl_2$ | $Na_2CO_3$ | 5:1 |
| 35A, 35B | 4.3 | Polysorbate 80 | Polyoxyethylene sorbitan fatty acid ester | 6.5 | $CaCl_2$ | $Na_2CO_3$ | 5:2 |
| 36A, 36B | 4.5 | Polysorbate 80 | Polyoxyethylene sorbitan fatty acid ester | 6.9 | $MgCl_2$ | $Na_2CO_3$ | 5:2 |

TABLE 1-3

Table of Examples and Comparative Examples (3)

| Example No. | pH before addition of metal ion | Nonionic surfactant | Kind of surfactant | Final pH | Divalent metal salt (A) | Salt carrying divalent anion (B) | A:B (molar ratio) |
|---|---|---|---|---|---|---|---|
| 37A, 37B | 4.5 | POE (20) stearyl ether | Polyoxyethylene alkyl ether | 6.6 | $CaCl_2$ | $Na_2CO_3$ | 5:1 |
| 38A, 38B | 4.3 | POE (20) stearyl ether | Polyoxyethylene alkyl ether | 6.8 | $CaCl_2$ | $Na_2CO_3$ | 5:1 |
| 39A, 39B | 4.5 | POE (20) stearyl ether | Polyoxyethylene alkyl ether | 6.5 | $CaCl_2$ | $Na_2CO_3$ | 5:1 |
| 40A, 40B | 4.4 | POE (20) stearyl ether | Polyoxyethylene alkyl ether | 6.9 | $CaCl_2$ | $Na_2CO_3$ | 5:1 |
| 41A, 41B | 4.5 | POE (20) stearyl ether | Polyoxyethylene alkyl ether | 6.4 | $MgCl_2$ | $Na_2CO_3$ | 5:1 |
| 42A, 42B | 4.6 | POE (20) stearyl ether | Polyoxyethylene alkyl ether | 6.8 | $MgCl_2$ | $Na_2CO_3$ | 5:1 |
| 43A, 43B | 4.5 | POE (20) stearyl ether | Polyoxyethylene alkyl ether | 6.7 | $MgCl_2$ | $Na_2CO_3$ | 5:2 |
| 44A, 44B | 4.6 | POE (20) stearyl ether | Polyoxyethylene alkyl ether | 6.8 | $CaCl_2$ | $Na_2CO_3$ | 5:3 |
| 45A, 45B | 4.5 | POE (20) stearyl ether | Polyoxyethylene alkyl ether | 6.6 | $MgCl_2$ | $Na_2CO_3$ | 5:3 |
| 46A, 46B | 4.5 | POE (20) stearyl ether | Polyoxyethylene alkyl ether | 6.7 | $CaCl_2$ | $Na_2CO_3$ | 5:1 |
| 47A, 47B | 4.3 | POE (20) stearyl ether | Polyoxyethylene alkyl ether | 6.6 | $CaCl_2$ | $Na_2CO_3$ | 5:1 |
| 48A, 48B | 4.4 | POE (20) stearyl ether | Polyoxyethylene alkyl ether | 6.8 | $CaCl_2$ | $Na_2CO_3$ | 5:1 |
| 43A, 43B | 4.5 | POE (20) stearyl ether | Polyoxyethylene alkyl ether | 6.7 | $MgCl_2$ | $Na_2CO_3$ | 5:2 |
| 44A, 44B | 4.6 | POE (20) stearyl ether | Polyoxyethylene alkyl ether | 6.8 | $CaCl_2$ | $Na_2CO_3$ | 5:3 |
| 45A, 45B | 4.5 | POE (20) stearyl ether | Polyoxyethylene alkyl ether | 6.6 | $MgCl_2$ | $Na_2CO_3$ | 5:3 |
| 46A, 46B | 4.5 | POE (20) stearyl ether | Polyoxyethylene alkyl ether | 6.7 | $CaCl_2$ | $Na_2CO_3$ | 5:1 |
| 47A, 47B | 4.3 | POE (20) stearyl ether | Polyoxyethylene alkyl ether | 6.6 | $CaCl_2$ | $Na_2CO_3$ | 5:1 |
| 48A, 48B | 4.4 | POE (20) stearyl ether | Polyoxyethylene alkyl ether | 6.8 | $CaCl_2$ | $Na_2CO_3$ | 5:1 |

POE (20) stearyl ether = Polyoxyethylene (20) stearyl ether
Polysorbate 80 = Polyoxyethylene (20) sorbitan monooleate, also referred to as oleic acid polyoxyethylene sorbitan.
Examples 37A, 37B, 40A, 40B, 41A, 41B, 43A, 43B, 44A, 44B, 45A, 45B, 46A and 46B contain polyethylene glycol (1000) as an additive.
Examples 38A, 38B, 39A, 39B, 42A, 42B, 47A and 47B contain polyethylene glycol (4000) as an additive.
Examples 48A and 48B contain polyethylene glycol (6000) as an additive.

Test Example 1

Thermostability Test of Preparation

Figure 3:
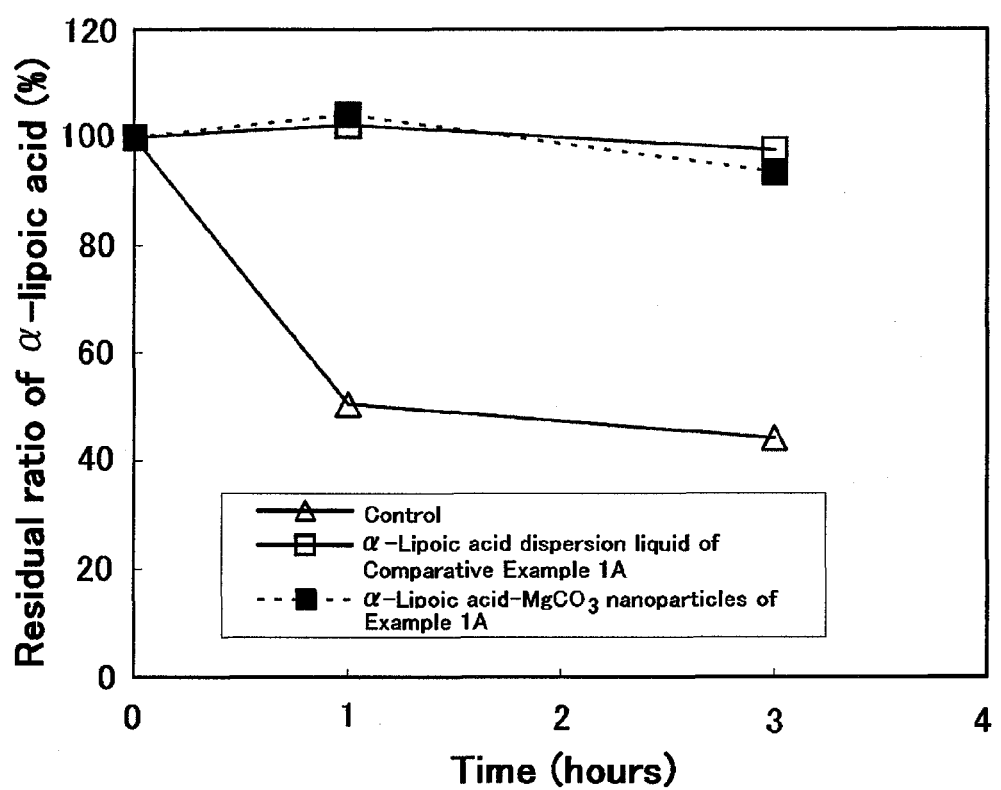
FIG. 3 shows the results of the residual ratio of α-lipoic acid. Symbol Δ represents the results for the reagent α-lipoic acid which is a control, symbol ■ represents the results for the α-lipoic acid nanoparticles of Comparative Example 1, and symbol □ represents the results for the α-lipoic acid-$MgCO_3$ nanoparticles of Example 1.

The α-lipoic acid-$MgCO_3$ nanoparticles produced in Example 1A, and the α-lipoic acid nanoparticles produced in Comparative Example 1A without adding magnesium chloride and sodium carbonate were respectively heated at 60° C., and the amounts of α-lipoic acid in the sample after one hour of heating and after 3 hours of heating were analyzed by HPLC. As a control, a reagent α-lipoic acid was used. The amount of α-lipoic acid after heating was divided by the amount of α-lipoic acid before heating, and the result was multiplied by 100 such that the residual ratio of α-lipoic acid was calculated. The results of the residual ratio of α-lipoic acid are presented in Table 2 below and in FIG. 3. Symbol Δ represents the results of control reagent of α-lipoicacid, symbol ■ represents the results of the α-lipoic acid dispersion liquid of Comparative Example 1, and symbol □ represents the results of the α-lipoic acid-$MgCO_3$ nanoparticles of Example 1A.

TABLE 2

| | | Heating time (hrs) | | |
|---|---|---|---|---|
| | | 0 | 1 | 3 |
| Residual ratio(%) | Control(reagent α-lipoic acid) | 100 | 50.51 | 44.20 |
| | α-Lipoic acid nanoparticles of Comparative Example 1A | 100 | 102.30 | 97.68 |
| | α-Lipoic acid-$MgCO_3$ nanoparticles of Example 1A | 100 | 104.22 | 93.59 |

As a result, while the amount of the α-lipoic acid of a reagent was reduced by about 55% after 3 hours of heating, in the α-lipoic acid-$MgCO_3$ of Example 1A and the α-lipoic acid nanoparticles produced without adding magnesium chloride and sodium carbonate, no substantial reduction in the amount of the α-lipoic acid was observed. As it is clear from a comparison with the control, it is understood that the preparation of the present invention is very excellent in the stability of α-lipoic acid.

Test Example 2

Improvement in Sulfurous Odor

The paste after freeze-drying of the α-lipoic acid-$MgCO_3$ nanoparticles produced in Example 1A, and the paste after freeze-drying of the α-lipoic acid nanoparticles produced in Comparative Example 1A without adding magnesium chloride and sodium carbonate, were respectively dispersed in distilled water such that the final concentration of α-lipoic acid reached 0.1%. The dispersions were placed in transparent test tubes made of resin, and the test tubes were left to stand indoors under sunlight. As a control, an aqueous dispersion liquid having α-lipoic acid dissolved in water (final concentration of α-lipoic acid 0.1%), which was prepared by adding an alkali (5M NaOH) to reagent α-lipoic acid, and thereby adjusting the pH to 7 to 7.5, was also left to stand in the same manner.

As a result, after a lapse of two weeks, the characteristic sulfurous odor strongly emanated from the control solution and the dispersion liquid of α-lipoic acid nanoparticles produced in Comparative Example 1A without adding magnesium chloride and sodium carbonate. The level was the same as the level of the aqueous dispersion liquid having α-lipoic acid dissolved in water, which was used as the control. On the contrary, no odor emanated from the α-lipoic acid-$MgCO_3$ nanoparticle dispersion liquid.

Test Example 3

Test for Suppression Effect of α-Lipoic Acid-$MgCO_3$ Nanoparticles on Ultraviolet-Induced Pigmentation in Colored Guinea Pig The dorsal part of a colored guinea pig (Weiser Maples, 5 weeks old, male) having melanogenic cells, was shaved in an area of 2 cm×2 cm, and the α-lipoic acid-MgCO₃ nanoparticle dispersion liquid (containing 350 μg of α-lipoic acid) obtained in Example 3A was applied in an amount of 80 mg per day, once a day, 5 days per week (from Monday to Friday). After the application, on each of the application initiation days (Monday) and after 2, 4 and 7 days (Wednesday, Friday and next Monday), irradiation with UV-A at 8 J/cm² and UV-B at 12 mJ/cm² were carried out. As an index of melanogenesis in the guinea pig skin, the brightness (L* value) of the skin was measured using a color-difference meter, and the amount of reduction of brightness was used as an index of the degree of blackening. In regard to the brightness, a larger L* value represents a whiter color. The absolute values of the amount of change in the brightness (ΔL* value) due to melanogenesis from the test initiation day were compared. Guinea pigs that were applied with only water which did not contain α-lipoic acid, were taken as a control group, and a comparison was made.

As a result, the group applied with the α-lipoic acid-MgCO₃ nanoparticles exhibited less reduction in the brightness as compared with the control group, that is, blackening of the skin was suppressed, throughout the whole test period. The absolute value of the ΔL* value at the time of completion of the test was 8.3 for the control group, while the absolute value was 6.6 for the group applied with the α-lipoic acid-MgCO₃ nanoparticles.

Figure 4:
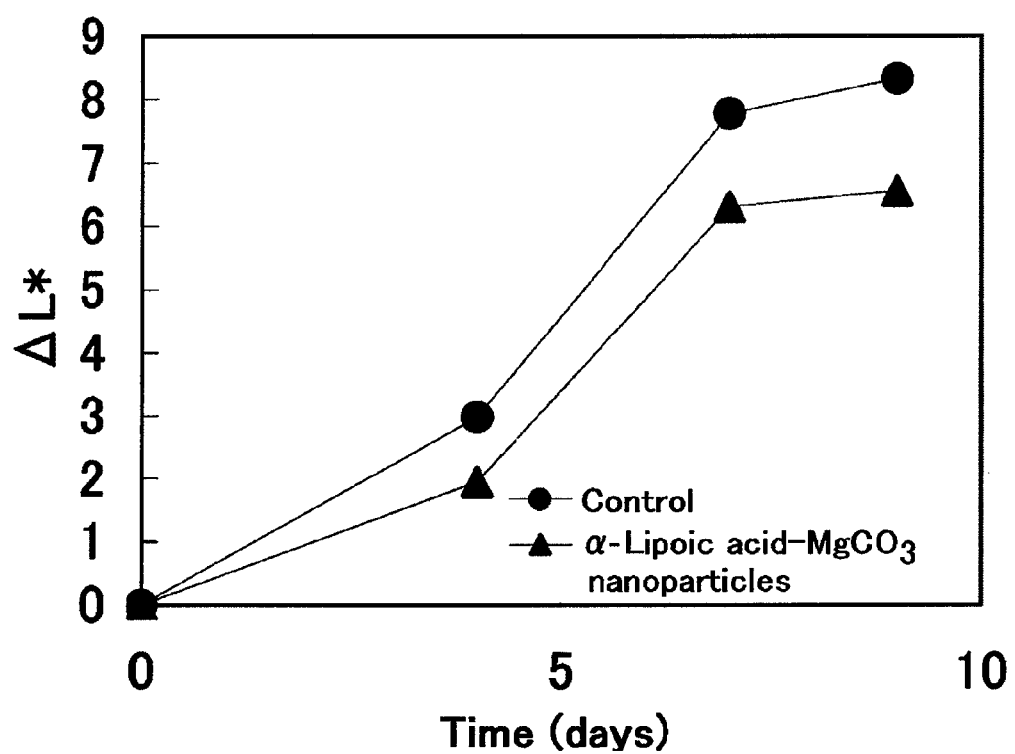
FIG. 4 shows the results of Test Example 3.

In Table 3 below and in FIG. 4, the absolute values of the ΔL* values measured after zero days (Monday), after 4 days (Friday), after 7 days (Monday) and after 9 days (Wednesday) are presented. It was confirmed by the results obtained as shown above, that the α-lipoic acid nanoparticles are absorbed into the skin and can suppress pigmentation caused by ultraviolet rays.

TABLE 3

| Sample | Time (days) | | | |
|---|---|---|---|---|
| | 0 | 4 | 7 | 9 |
| Control (water) | 0 | 3.0 | 7.8 | 8.3 |
| α-Lipoic acid-MgCO₃ nanoparticle dispersion liquid | 0 | 2.0 | 6.3 | 6.6 |

Test Example 4

Test for Verifying Effects of α-Lipoic Acid-MgCO₃ Nanoparticles on Skin Moisture, Barrier Function and Recovery from Wrinkles in Photoaging Model Mouse The dorsal part of a hairless mouse (Hos: HR-1, 7 weeks old, male) was irradiated with UV-B at 55 mJ/cm² per day for 2 months, 5 days per week (that is, irradiated only from Monday to Friday, not irradiated on Saturdays and Sundays), and thereby a photoaging model mouse was produced. The α-lipoic acid-MgCO₃ nanoparticle dispersion liquid (containing 350 μg of α-lipoic acid) obtained by Example 3A was applied on this mouse in an amount of 80 mg per day, once a day, 5 days per week (that is, applied only from Monday to Friday, not applied on Saturdays and Sundays) for 1 month. The mouse skin was subjected, at the time of the initiation of application and at the time of the completion of application, to an observation of the skin condition by visual inspection, and measurement of the amount of moisture in the stratum corneum and the amount of transepidermal water loss (TEWL), to evaluate the conditions of wrinkles and stratum corneum moisture, and the skin barrier functions.

Figure 5:
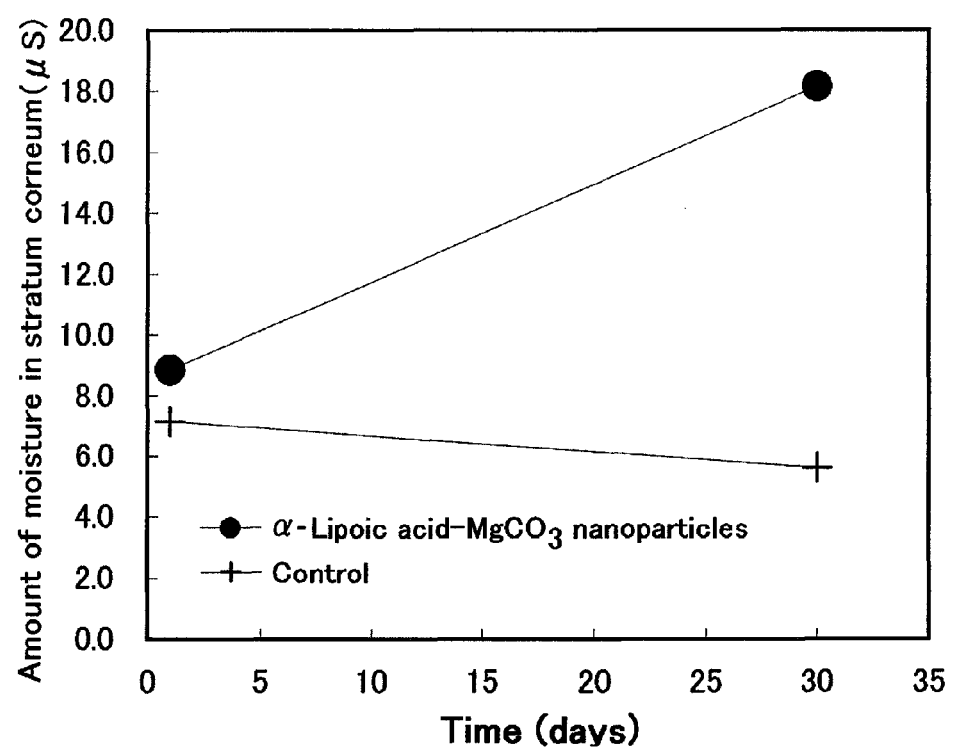
FIG. 5 shows the results of Test Example 4.
Figure 6:
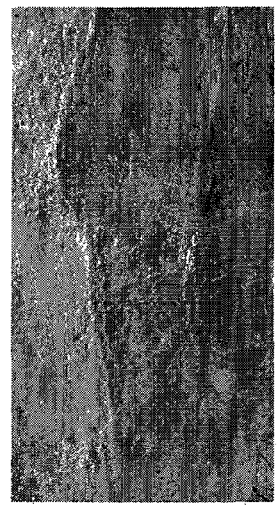
FIG. 6 shows a replica of the wrinkles in Test Example 4.
Figure 6:
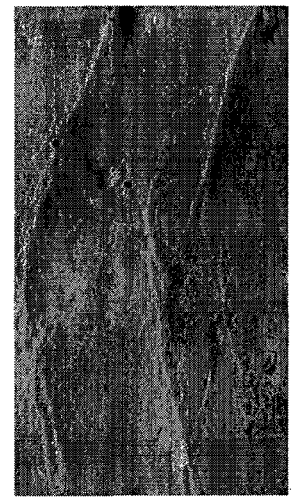
Figure 6:
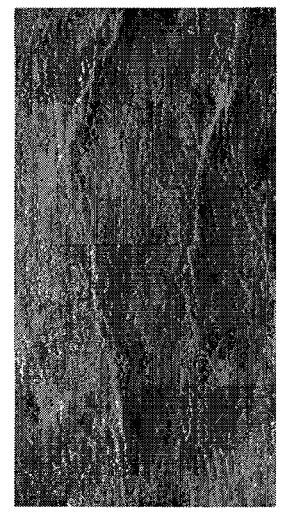
Figure 6:
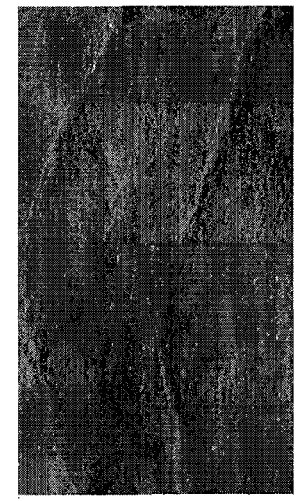

As a result, as shown in Table 4 below and in FIG. 5, the group applied with the α-lipoic acid-MgCO₃ nanoparticles was recognized to have a recovery of the amount of moisture in the stratum corneum as compared with those at the time of application initiation. On the other hand, the control group (similarly applied with only water which did not contain α-lipoic acid) was not recognized to have a recovery in the amount of moisture in the stratum corneum. The amount of moisture in the stratum corneum at the time of completion of the test was 18.2 (μs) for the group applied with the α-lipoic acid-MgCO₃ nanoparticles, while the amount was 5.6 (μs) for the control group. Furthermore, the TEWL value on the last day of the test was 15.7 (g/h·m²) for the group applied with the α-lipoic acid-MgCO₃ nanoparticles, while the TEWL value was 32.6 (g/h·m²) for the control group. Thus, it was confirmed that application with the α-lipoic acid-MgCO₃ nanoparticles caused the recovery of the barrier function of the skin. A photograph of the replica of wrinkles is presented in FIG. 6. Any changes in the wrinkle state as compared with the time of initiation of test was not recognized in the control group, but in the group applied with the α-lipoic acid-MgCO₃ nanoparticles, an obvious decrease in wrinkles was recognized. From the results shown above, the following effects were confirmed. The α-lipoic acid nanoparticles are absorbed into the skin and these nanoparticles return a photoaged skin state into a healthy state.

TABLE 4

Amount of moisture in stratum corneum

| | Time (days) | |
|---|---|---|
| | 1 | 30 |
| α-Lipoic acid-MgCO₃ nanoparticle dispersion liquid | 8.9 | 18.2 |
| Control (water) | 7.2 | 5.6 |

Measurement Example 2

Measurement of Particle Size

Figure 7:
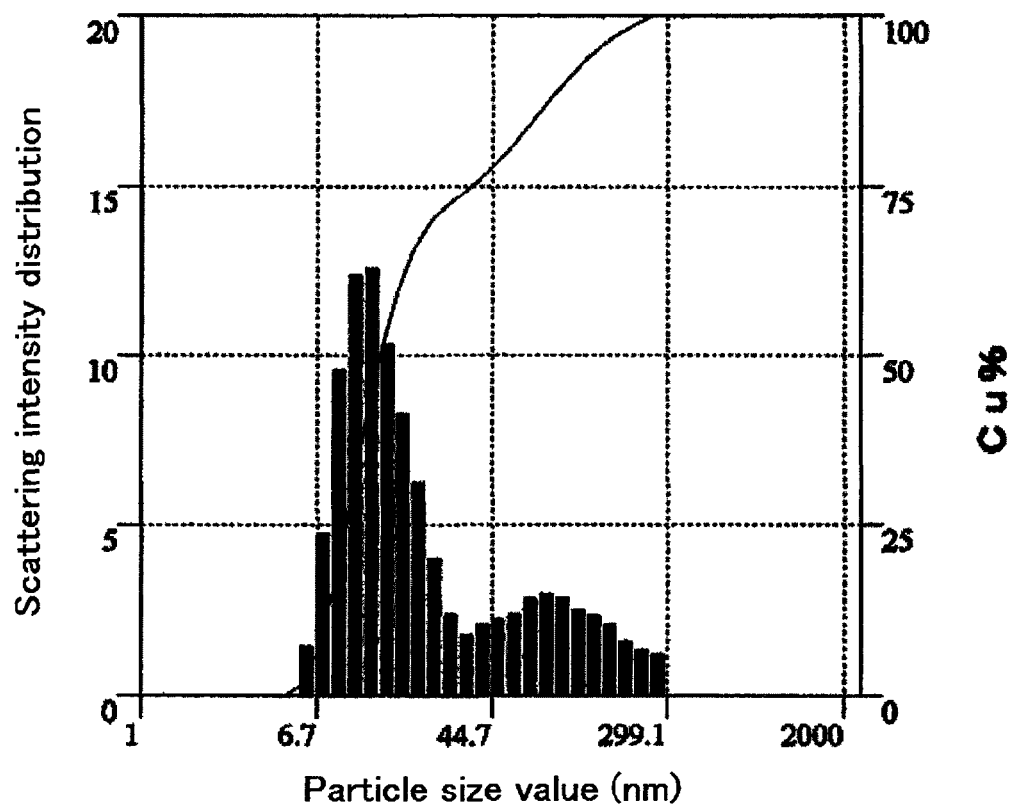
FIG. 7 shows the result of the particle size distribution of the α-lipoic acid-$CaCO_3$ nanoparticles produced by using distilled water in Example 22A, as measured using a light scattering photometer (Otsuka Electronics Co., Ltd., FPAR1000).

The solution of α-lipoic acid-CaCO₃ nanoparticles produced in Example 22A was subjected to the measurement of particle size with a light scattering photometer (Otsuka Electronics Co., Ltd., FPAR1000). As a result, it was confirmed that the particle size of the α-lipoic acid-CaCO₃ nanoparticles produced in Example 22A was about 20 nm. The particle sizes were almost the same both when distilled water was used and when ion-exchanged water was used. The results of the particle size distribution of the α-lipoic acid-CaCO₃ nanoparticles produced in Example 22A using distilled water, as measured using Otsuka Electronics Co., Ltd., FPAR1000 are presented in FIG. 7.

Measurement Example 3

Measurement of Particle Size

Figure 8:
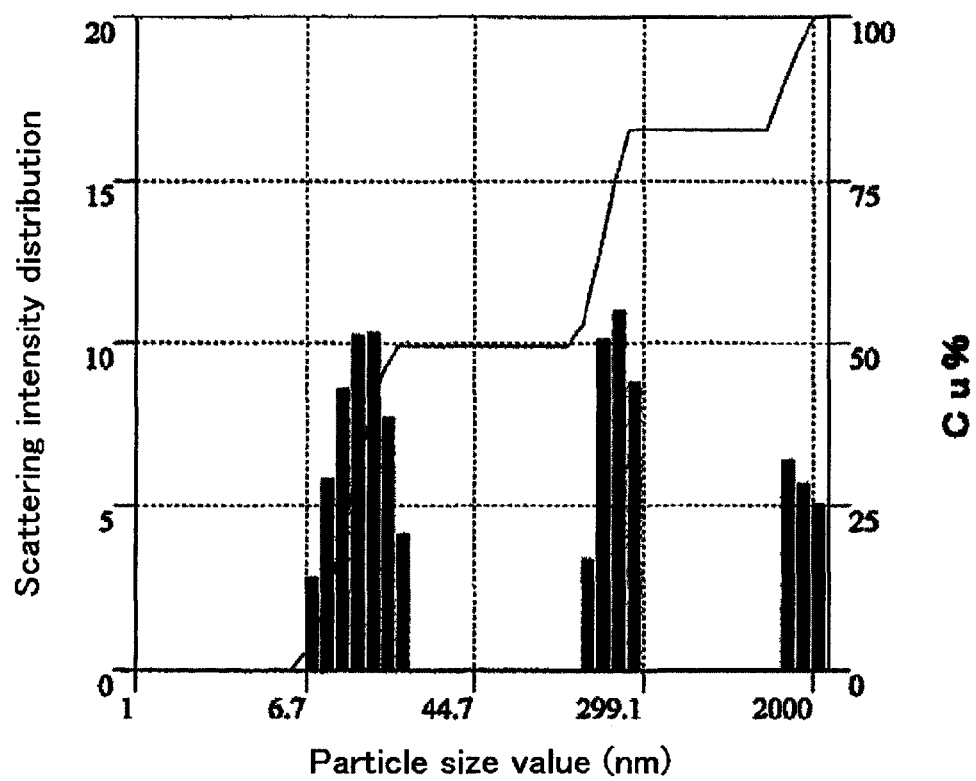
FIG. 8 shows the result of the particle size distribution of the α-lipoic acid-$MgCO_3$ nanoparticles produced by using distilled water in Example 29B, as measured using a light scattering photometer (Otsuka Electronics Co., Ltd., FPAR1000).

The particle size of solution of α-lipoic acid-MgCO₃ nanoparticles produced in Example 29A was measured by a light scattering photometer (Otsuka Electronics Co., Ltd., FPAR1000). From the fact that the solution was perfectly transparent and the results of the measurement of particle size, it was confirmed that the α-lipoic acid-MgCO₃ nanoparticles produced in Example 29A form weak clusters having average particle sizes of 200 nm and 1700 nm in which primary particles have an average particle size of about 12 nm. The particle sizes were almost the same both when distilled water was used and when ion-exchanged water was used. The result of the particle size distribution of the α-lipoic acid-MgCO₃ nanoparticles produced by using ion-exchanged water in Example 29A, as measured with Otsuka Electronics Co., Ltd., FPAR1000, is presented in FIG. 8.

Measurement Example 4

Measurement of Particle Size

For each of the solutions of α-lipoic acid-MgCO₃ nanoparticles produced in Examples 24A, 24B, 25A, 25B, 33A, 33B, 36A and 36B, the particle size was measured with a light scattering photometer (Otsuka Electronics Co., Ltd., FPAR1000).

The average particle sizes (nm) of the respective α-lipoic acid nanoparticles measured in Measurement Examples 1 to 4 are summarized in Table 5 below.

TABLE 5

| | | Average particle size (nm) |
|---|---|---|
| Examples 1A, 1B | α-Lipoic acid-MgCO₃ nanoparticles | 10 |
| Comparative Example 1A | α-Lipoic acid dispersion liquid | 760 |
| Examples 22A, B | α-Lipoic acid-CaCO₃ nanoparticles | 19.3 |
| Examples 24A, B | α-Lipoic acid-CaCO₃ nanoparticles | 17.8 |
| Examples 25A, B | α-Lipoic acid-MgCO₃ nanoparticles | 55.9 |
| Examples 29A, B | α-Lipoic acid-MgCO₃ nanoparticles | 109.2 |
| Examples 33A, B | α-Lipoic acid-CaCO₃ nanoparticles | 82.7 |
| Examples 36A, B | α-Lipoic acid-MgCO₃ nanoparticles | 11 |

Test Example 5

Thermostability Test of Preparation

Figure 9:
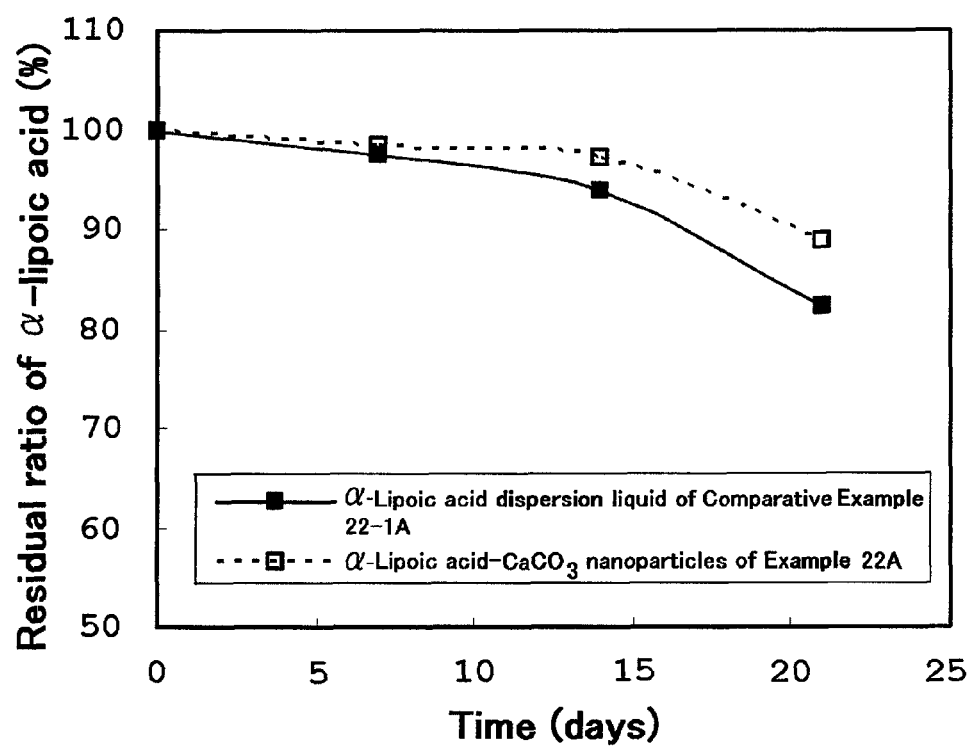
FIG. 9 shows the results of Test Example 5.

The α-lipoic acid-CaCO₃ nanoparticles produced in Example 22A and the α-lipoic acid dispersion liquid produced in Comparative Example 22-1A (neither calcium chloride nor sodium carbonate were added) were respectively stored at 60° C. (storage under heating), and the amount of α-lipoic acid in the solution was analyzed by HPLC once every week up to 3 weeks. The amount of α-lipoic acid after storage under heating was divided by the amount of α-lipoic acid before heating, and the result was multiplied by 100 such that the residual ratio of α-lipoic acid was calculated. The results of the residual ratio of α-lipoic acid are presented in Table 6 below and in FIG. 9. Symbol ■ indicates the results for the α-lipoic acid dispersion liquid of Comparative Example 22-1A, and symbol □ indicates the results for the α-lipoic acid-CaCO₃ nanoparticles of Example 22A.

TABLE 6

| | | Time elapsed (days) | | | |
|---|---|---|---|---|---|
| | | 0 | 7 | 14 | 21 |
| Residual ratio (%) | α-Lipoic acid dispersion liquid of Comparative Example 22-1A | 100.0 | 97.5 | 93.9 | 82.1 |
| | α-Lipoic acid-CaCO₃ nanoparticles of Example 22A | 100.0 | 98.4 | 97.2 | 88.7 |

As a result, after a storage for 3 weeks at 60° C., the α-lipoic acid nanoparticles produced in Comparative Example 22-1A without adding magnesium chloride and sodium carbonate showed a reduction of about 18%, but in the α-lipoic acid-CaCO₃ nanoparticles of Example 22A, the reduction of α-lipoic acid was suppressed to about 11%. Accordingly, it is understood that the preparation of the present invention is quite excellent in the stability of α-lipoic acid.

Test Example 6

Thermostability Test of Preparation

Figure 10:
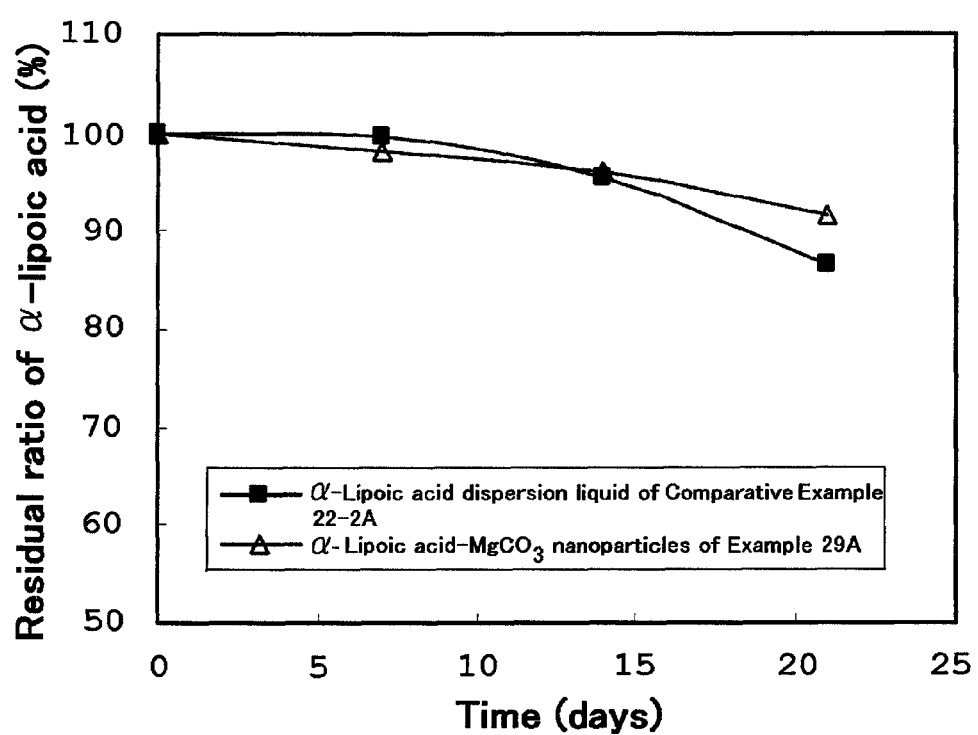
FIG. 10 shows the results of Test Example 6.

The α-lipoic acid-MgCO₃ nanoparticles produced in Example 29A and the α-lipoic acid nanoparticles produced in Comparative Example 22-2A without adding magnesium chloride and sodium carbonate were respectively stored at 60° C., and the amount of α-lipoic acid in the solution was analyzed by HPLC once every week up to 3 weeks. The amount of α-lipoic acid after storage under heating was divided by the amount of α-lipoic acid before heating, and the result was multiplied by 100 such that the residual ratio of α-lipoic acid was calculated. The results of the residual ratio of α-lipoic acid are presented in Table 7 below and in FIG. 10. Symbol ■ indicates the results for the α-lipoic acid nanoparticles of Comparative Example 22-2A, and symbol Δ indicates the results for the α-lipoic acid-MgCO₃ nanoparticles of Example 29A.

TABLE 7

| | | Time elapsed (days) | | | |
|---|---|---|---|---|---|
| | | 0 | 7 | 14 | 21 |
| Residual ratio (%) | α-Lipoic acid dispersion liquid of Comparative Example 22-2A | 100.0 | 99.6 | 95.3 | 86.6 |
| | α-Lipoic acid-MgCO₃ nanoparticles of Example 29A | 100.0 | 98.1 | 96.1 | 91.5 |

As a result, after a storage for 3 weeks at 60° C., the α-lipoic acid nanoparticles produced in Comparative Example 22-2A without adding magnesium chloride and sodium carbonate showed a reduction of about 13%, but in the α-lipoic acid-MgCO₃ nanoparticles of Example 29A, the reduction of α-lipoic acid was suppressed to about 8%. Accordingly, it is understood that the preparation of the present invention is quite excellent in the stability of α-lipoic acid.

Test Example 7

Test on Function of α-Lipoic Acid-MgCO$_3$ Nanoparticles in Connection with Differentiation of Preadipocytes)

1.5 ml of D-MEM medium (D-MEM medium supplemented with 10% FCS, 100 units/ml of penicillin, and 100 µg/ml of streptomycin, all at final concentrations) was added to a plastic petri dish having a diameter of 3.5 cm. To this, 5.0×10$^4$ cells of 3T3-L1 cells, which are preadipocytes, were suspended, and precultured for 3 days to result in a confluent state. Thereafter, the medium was replaced with 3 ml of an adipocyte differentiation induction medium (D-MEM supplemented with 10% FCS, 100 units/ml of penicillin, 100 µg/ml of streptomycin, 5 µg/ml of insulin, 0.25 µM of dexamethasone, and 0.5 mM of isobutyl-methylxanthine (IBMX), all at final concentrations). After another 2 days, the medium was replaced with 3 ml of the adipocyte differentiation induction medium of the same composition, and then the culturing was carried out for 2 days. Thus, the culturing in the adipocyte differentiation induction medium was carried out for 4 days in total. During this culturing, an α-lipoic acid solution or the α-lipoic acid-MgCO$_3$ nanoparticle solution of Example 20A was added to the adipocyte differentiation induction medium to result in 0, 100, 250 or 500 µM of α-lipoic acid concentration. The culturing were all carried out under the conditions of 5% CO$_2$ and 37° C.

The amount of accumulated lipids in the cultured cells thus obtained was measured. The cells were washed with 1 ml of a PBS buffer solution, and then the cells were fixed for 5 minutes with neutral buffered formalin. The cells were further washed with a 70% ethanol solution and distilled water. Subsequently, 1 ml of an Oil Red O solution (a staining solution prepared by mixing a saturated Oil Red O/isopropanol solution and distilled water at a ratio of 6:4 and filtering the mixture) was added, and left to stand for 15 minutes. The staining solution was removed, and the cells were washed with a 70% ethanol solution until the dye no longer diffused. Then, 0.75 ml of a 4% Nonidet P-40/isopropanol solution was added, stirred for 30 minutes, and the dye was allowed to elute out. The whole amount of this solution was recovered, and the absorbance at a wavelength of 520 nm was measured with a spectrophotometer.

Figure 11:
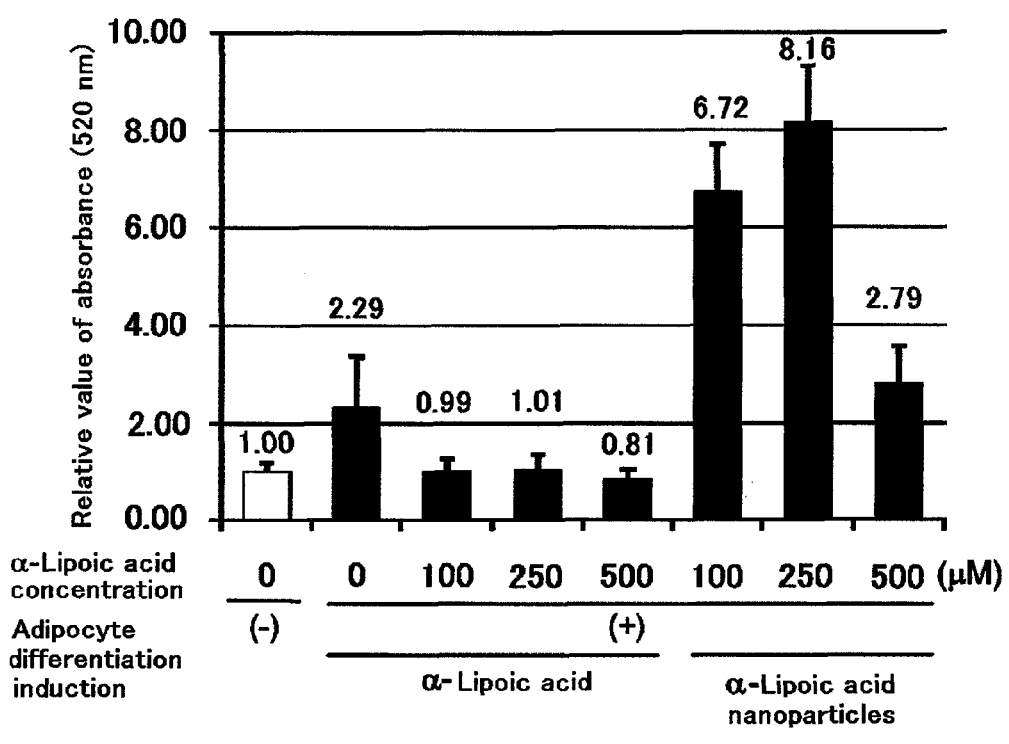
FIG. 11 shows the results obtained in Test Example 7 by adding α-lipoic acid-$MgCO_3$ nanoparticles into a 3T3-L1 cell culture medium, staining the lipids accumulated in immature adipocytes with Oil Red O, and measuring with a spectrophotometer (wavelength 520 nm).

As a result, while the addition of α-lipoic acid resulted the reduction of the accumulation of lipids, it was recognized that the addition of α-lipoic acid-MgCO$_3$ nanoparticles has an action of accumulating lipids in the cells (FIG. 11). That is, it was suggested that the α-lipoic acid-MgCO$_3$ nanoparticles has a function of allowing efficient incorporation of sugar into immature adipocytes. Since the α-lipoic acid nanoparticles accelerated the incorporation of sugar in the test described above, an effect of improving the blood glucose level, which has not been recognized with α-lipoic acid alone, can be expected for the α-lipoic acid nanoparticles, and this suggested the usefulness of the nanoparticles as a therapeutic drug for diabetes.

Test Example 8

Test on Function of α-Lipoic Acid-MgCO$_3$ Nanoparticles in Connection with Dedifferentiation of Mature Adipocytes 1.5 ml of D-MEM medium (D-MEM medium supplemented with 10% FCS, 100 units/ml of penicillin, and 100 µg/ml of streptomycin, all at final concentrations) was added to a plastic petri dish having a diameter of 3.5 cm. To this, 5.0×10$^4$ cells of 3T3-L1 cells, which are preadipocytes, were suspended, and precultured for 3 days to result in a confluent state. Thereafter, the medium was replaced with 3 ml of an adipocyte differentiation induction medium (D-MEM medium supplemented with 10% FCS, 100 units/ml of penicillin, 100 µg/ml of streptomycin, 5 µg/ml of insulin, 0.25 µM of dexamethasone, and 0.5 mM of isobutyl-methylxanthine, all at final concentrations), and the culturing was carried out for 4 days to induce the differentiation into adipocytes. Thereafter, the medium was replaced with an adipocyte maturation medium (D-MEM medium supplemented with 10% FCS, 100 units/ml of penicillin, 100 µg/ml of streptomycin, and 5 µg/ml of insulin, all at final concentrations), and the culturing was carried out for 7 days. Thereafter, the medium was replaced with a test medium, and culturing was carried out for another 4 days. The test medium was prepared by adding an α-lipoic acid solution or the α-lipoic acid-MgCO$_3$ nanoparticle solution of Example 20A to the adipocyte maturation medium to result in 0, 100, 250 or 500 µM of α-lipoic acid concentration. Each of the media was replaced with the same medium every other day during the culture. The culture was all carried out under the conditions of 5% CO$_2$ and 37° C.

The amount of accumulated lipids in the cultured cells thus obtained was measured. The cells were washed with 1 ml of a PBS buffer solution, and then the cells were fixed for 5 minutes with neutral buffered formalin. The cells were further washed with a 70% ethanol solution and distilled water. To this, 1 ml of an Oil. Red O solution was added, and left to stand for 15 minutes. After the staining, the cells were washed with a 70% ethanol solution until the dye no longer diffused. To this, 0.75 ml of a 4% Nonidet P-40/isopropanol solution was added, stirred for 30 minutes, and the dye was allowed to elute out. The total amount of this solution was recovered, and the absorbance at a wavelength of 520 nm was measured with a spectrophotometer.

Figure 12:
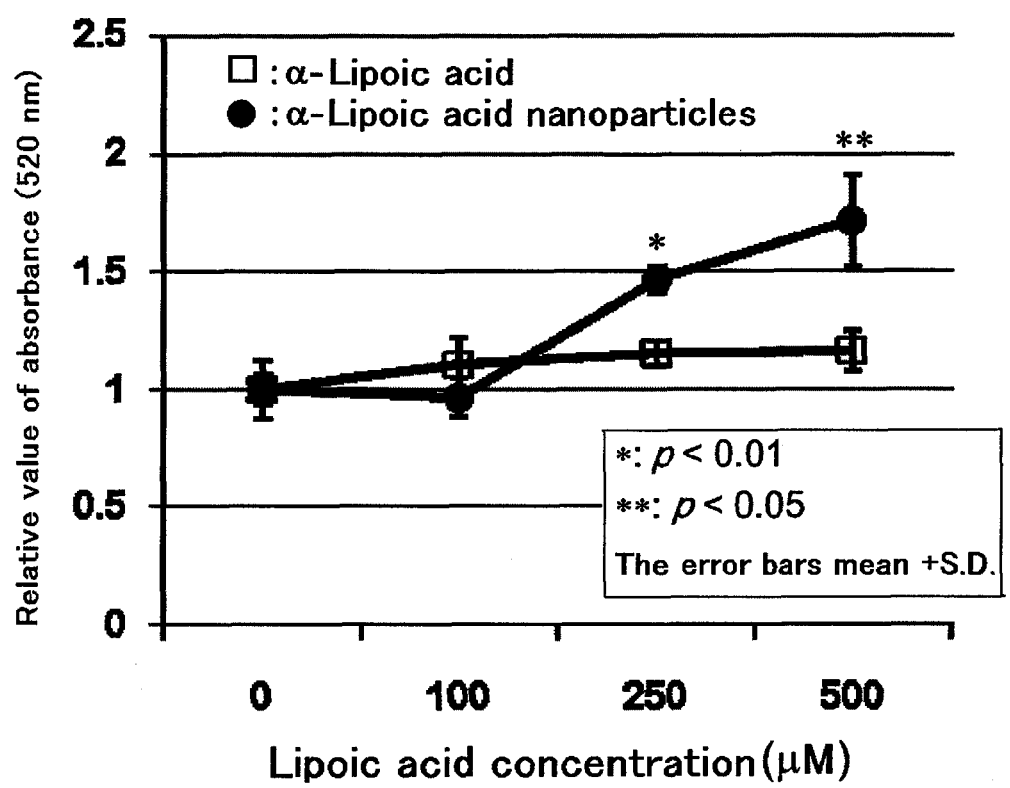
FIG. 12 shows the results obtained in Test Example 8 by adding α-lipoic acid-$MgCO_3$ nanoparticles into a 3T3-L1 cell culture medium, staining the lipids accumulated in mature adipocytes with Oil Red O, and measuring with a spectrophotometer (wavelength 520 nm).

As a result, in the α-lipoic acid-added group, the amount of lipid accumulation was almost indifferent from that of the non-added group; however, in the group added with the α-lipoic acid-MgCO$_3$ nanoparticles, an action of accumulating lipids in the cells was recognized (FIG. 12). That is, it is suggested that, similarly to Test Example 7, the α-lipoic acid-MgCO$_3$ nanoparticles have an action of allowing efficient incorporation of sugar into mature adipocytes. Particularly with regard to adipocytes, it was confirmed that they have the action of allowing accumulation of lipids at all stages of differentiation. From the results obtained above, a high effect of improving blood glucose levels, which has not been recognized with α-lipoic acid alone, can be expected for the α-lipoic acid nanoparticles, and this suggested the usefulness of the nanoparticles as a therapeutic drug for diabetes.

Test Example 9

Analysis of Stability of α-Lipoic Acid-MgCO$_3$ Nanoparticles in Culture Medium and Cellular Localization of the Nanoparticles Culturing was carried out in the same manner as those in Test Example 7. α-Lipoic acid and the α-lipoic acid-MgCO$_3$ nanoparticles of Example 20A were respectively added at a final concentration of 250 µM. The total amount of the supernatant of these culture media of cells was recovered and was designated as a culture supernatant fraction. The cells were further washed with a PBS buffer solution, and then recovery and washing of the cells was carried out by conventional methods. The cells were precipitated by centrifugation, and the cells were suspended in 500 μL of purified water and disrupted by ultrasonication. This disrupted cell fluid was centrifuged for 15 minutes at 4° C. at 15000 rotations per minute, and the supernatant was recovered and designated as a cell disrupted fluid fraction. The residual α-lipoic acid concentration of each fraction was quantified using a high performance liquid chromatography-mass spectrometer.

Figure 13:
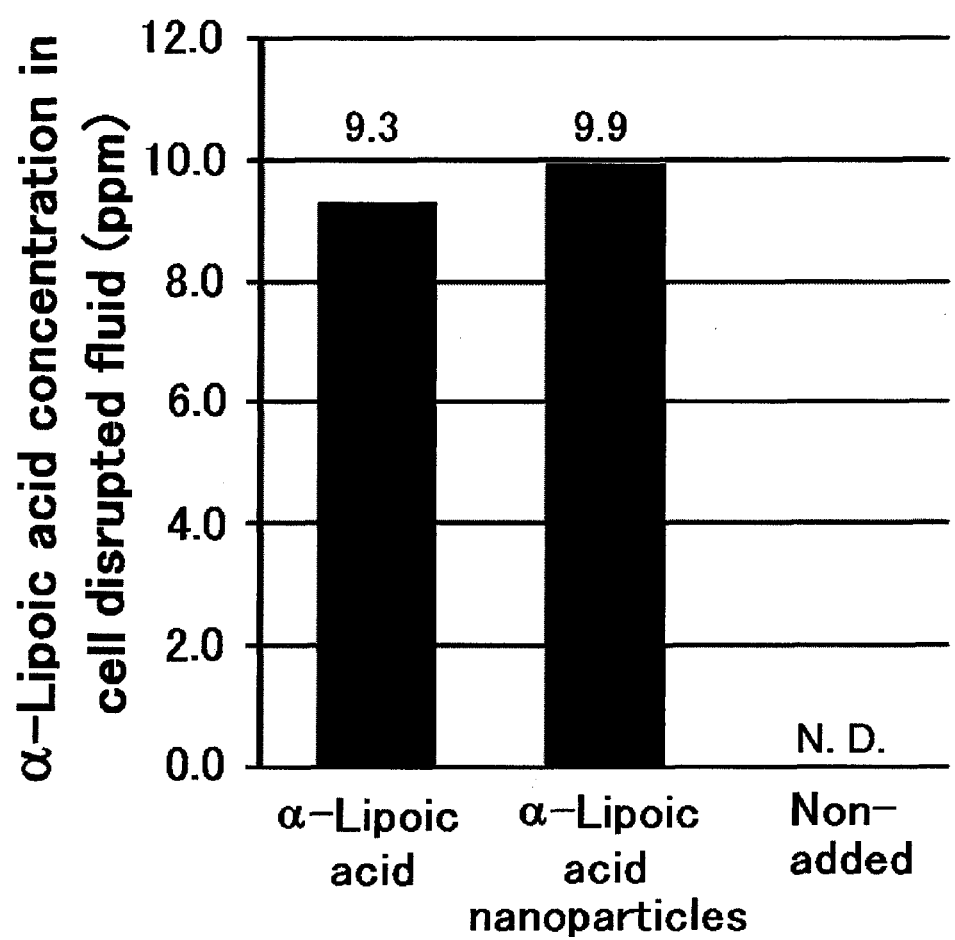
FIG. 13 shows the results obtained in Test Example 9 by measuring the α-lipoic acid concentration in the cell disrupted fluid obtained by disrupting immature adipocytes cultured in a 3T3-L1 cell culture medium with α-lipoic acid-$MgCO_3$ nanoparticles added therein, using a high performance liquid chromatograph-mass spectrometer.
Figure 14:
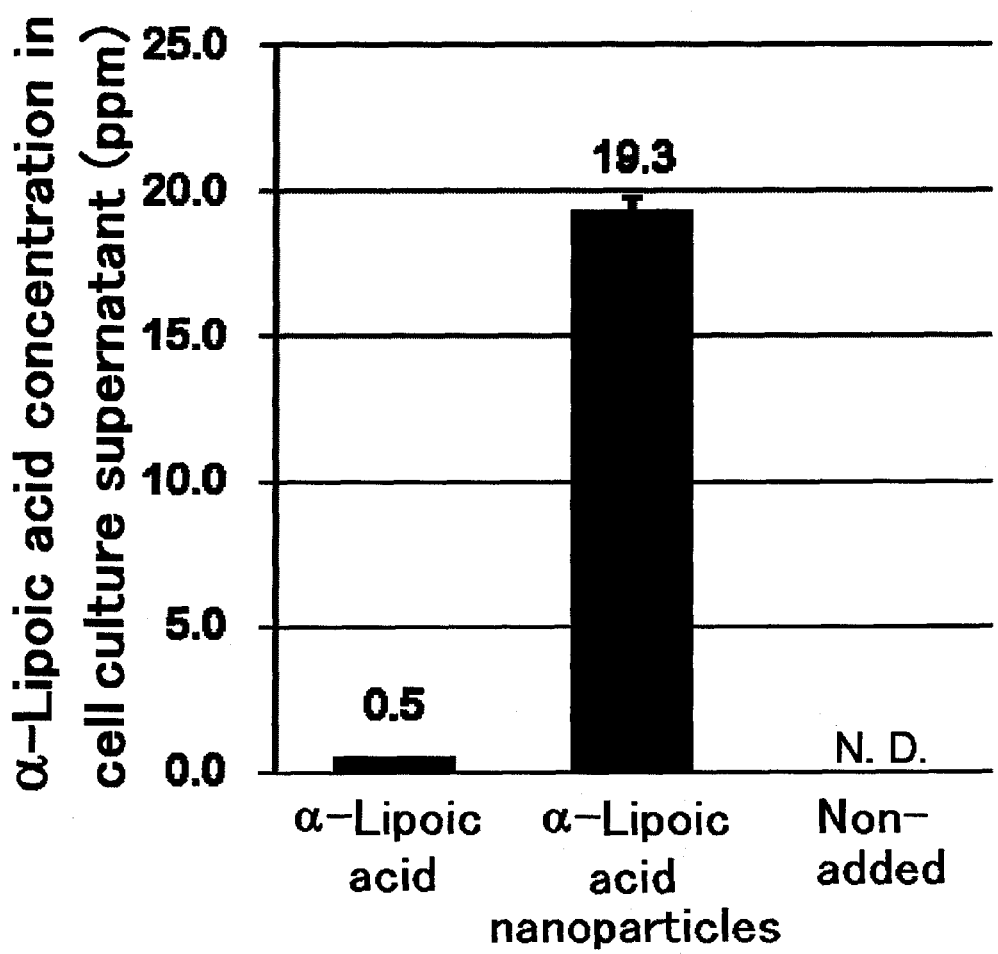
FIG. 14 shows the results obtained in Test Example 9 by measuring the α-lipoic acid concentration in the supernatant of the immature adipocyte culture cultured in a 3T3-L1 cell culture medium with α-lipoic acid-$MgCO_3$ nanoparticles added therein, using a high performance liquid chromatograph-mass spectrometer.

As a result, no difference in concentration was recognized in the cell disrupted fluid fraction (FIG. 13). However, in the culture supernatant fraction, a high α-lipoic acid residual was confirmed for the experimental group added with α-lipoic acid-$MgCO_3$ nanoparticles (FIG. 14). From the results obtained above, it was confirmed that the α-lipoic acid-$MgCO_3$ nanoparticles were quite stable in the culture medium. Furthermore, it was suggested that the difference in the action between the α-lipoic acid and the α-lipoic acid-$MgCO_3$ nanoparticles as observed in Test Example 7 is not due to the difference in the α-lipoic acid concentration in the cells, but is due to the difference in the physicochemical properties possessed by the α-lipoic acid-$MgCO_3$ nanoparticles.

Test Example 10

Figure 15:
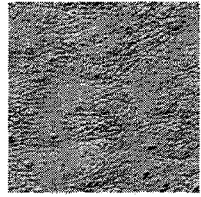
FIG. 15 shows the example criteria for evaluation of the wrinkle model mouse produced in Test Example 10.
Figure 15:
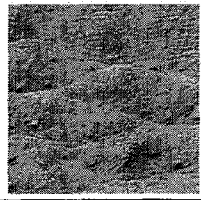
Figure 15:
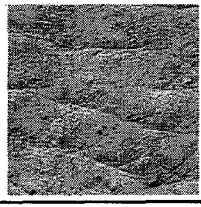
Figure 15:
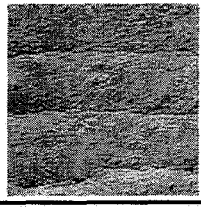

Test on Anti-Wrinkle Effect of α-Lipoic Acid-$MgCO_3$ Nanoparticle Application in Wrinkle Model Mouse A hairless mouse (Hr/kud, 9 weeks old, male) was irradiated with ultraviolet rays, and thus a wrinkle model mouse was produced. In the production of this wrinkle model, the mouse was irradiated with ultraviolet rays over 13 weeks (5 days/week, from Monday to Friday), such that the total exposure doses of UVA and UVB were 148.99 $J/cm^2$ and 3.49 $J/cm^2$, respectively. After the production of the wrinkle model, a commercially available cosmetic product containing 0.01% α-lipoic acid and the 0.01% α-lipoic acid-$MgCO_3$ nanoparticle-containing aqueous dispersion liquid of Example 21A were applied on the dorsal part of the mouse in an amount of 30 $mg/cm^2$/day each, 5 times per week (from Monday to Friday), and this was carried out for 6 weeks. As control groups, an unapplied group in which the mice were bred for 6 weeks without applying any preparation and an untreated group in which the mice were bred concurrently without being subjected to wrinkle formation by UV irradiation, were used. The produced wrinkle model was evaluated by a replica method. Based on the originally established scoring criteria shown in FIG. 15, the degrees of wrinkles were compared by visual inspection, and scoring of the wrinkle model mouse was performed. Furthermore, paraffin-embedded sections of the mouse dorsal skin were produced, were stained for hyaluronic acid and thereby their total amounts were compared. The staining for hyaluronic acid was carried out using a method in which biotin-labeled hyaluronic acid-bound protein (biotin-labeled HABP, Seikagaku Corp.) was used as a probe and was detected by a streptavidin-labeled fluorescent dye (Cy3 streptavidin, Jackson ImmunoResearch LABORATORIES).

Figure 16:
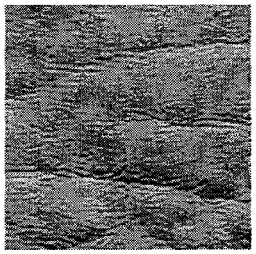
FIG. 16 shows a mouse wrinkle replica obtained by applying α-lipoic acid-$MgCO_3$ nanoparticles on a wrinkle model mouse produced in Test Example 10 for 6 weeks, and the scores for wrinkle evaluation.
Figure 16:
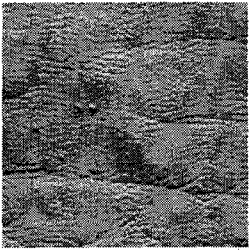
Figure 16:
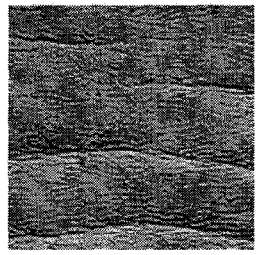
Figure 16:
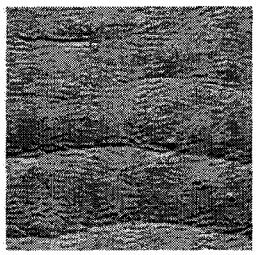
Figure 16:
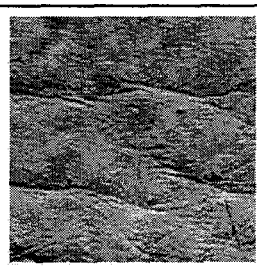
Figure 16:
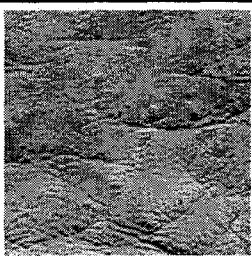

As a result, from the analysis of the replica of the mouse dorsal part where 6 weeks application was carried out, a higher wrinkle improving effect was observed in the group applied with a 0.01% α-lipoic acid-$MgCO_3$ nanoparticle-containing aqueous dispersion liquid as compared with the 0.01% α-lipoic acid-containing commercial product (FIG. 16). Also, in the scoring, a wrinkle improving effect was confirmed (Table 8).

Figure 17:
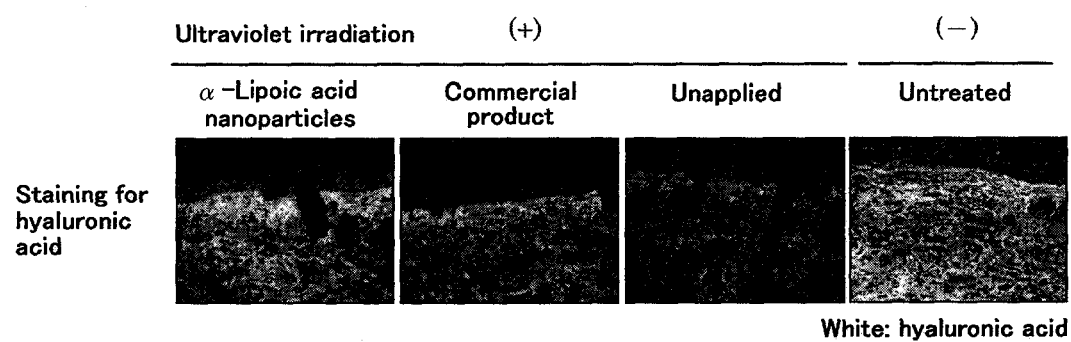
FIG. 17 shows the results of hyaluronic acid staining of the wrinkle model mouse skin section produced in Test Example 10.

Staining for hyaluronic acid of the same mouse skin sections was carried out, and as a result, reduction of hyaluronic acid was observed in the group of 0.01% α-lipoic acid-containing commercial product or unapplied group, but accumulation of hyaluronic acid to the same extent as that of the untreated group was observed in the group applied with 0.01% α-lipoic acid-$MgCO_3$ nanoparticles (FIG. 17). It is known that reduction of hyaluronic acid in the dermis is related to the formation of wrinkles. From the results shown above, it was confirmed that the α-lipoic acid-$MgCO_3$ nanoparticles have an action of increasing the amount of hyaluronic acid, which is an extracellular matrix, in the dermal layer which has been damaged by ultraviolet rays, and wrinkles were improved by such an effect.

TABLE 8

Wrinkle improving effect by application of α-lipoic acid-$MgCO_3$ nanoparticles

| Test group | | Before test | After 6 weeks |
|---|---|---|---|
| Wrinkle model | α-Lipoic acid nanoparticles (n = 5) | 2.94 ± 0.75 | 2.40 ± 0.59 |
| | Commercial product (n = 6) | 3.00 ± 0.71 | 2.63 ± 0.77 |
| | Unapplied (n = 5) | 3.00 ± 0.70 | 3.04 ± 0.61 |
| | Untreated (n = 5) | 1.00 ± 0.00 | 1.03 ± 0.07 |

Average ± S.D.

Test Example 11

Test on Human Wrinkle Improving Effect by Application of α-Lipoic Acid-$MgCO_3$ Nanoparticles A male subject, whose age was in the thirties (Subject 1) was made to evenly apply a 0.01% α-lipoic acid-containing aqueous dispersion liquid on one half of his face and the 0.01% α-lipoic acid-$MgCO_3$ nanoparticle-containing aqueous dispersion liquid of Example 21A on the other half of his face, two times a day everyday. Also, a female subject, whose age was in the fifties (Subject 2) was made to evenly apply the 0.01% α-lipoic acid-$MgCO_3$ nanoparticle-containing aqueous dispersion liquid of Example 21A on one half of her face everyday, and the other half of her face was left unapplied. The test period was 16 weeks respectively, and the evaluation of wrinkles was carried out by producing replicas of the crow's feet area before the test and after 16 weeks.

Figure 18:
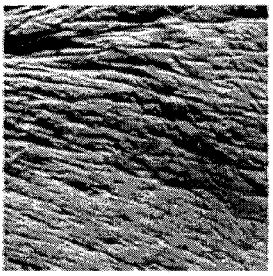
FIG. 18 shows the wrinkle replica of Test Example 11.
Figure 18:
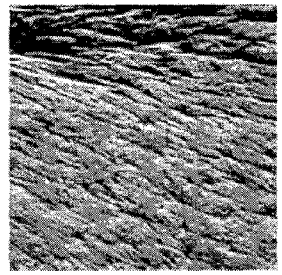
Figure 18:
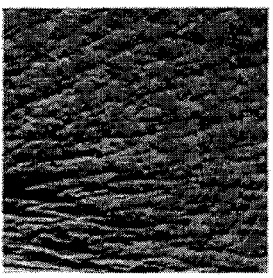
Figure 18:
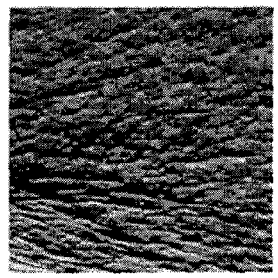
Figure 18:
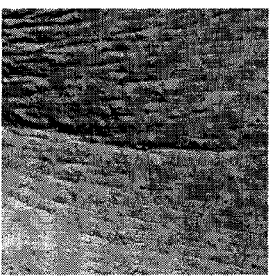
Figure 18:
Figure 18:
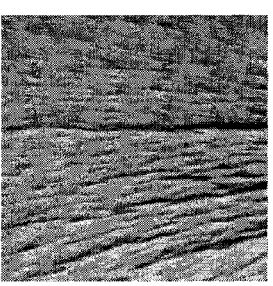
Figure 18:
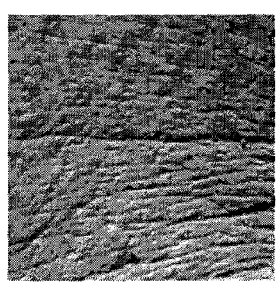

As a result, in both of the subjects, an improvement in wrinkles was observed on the side applied with the 0.01% α-lipoic acid-$MgCO_3$ nanoparticle-containing aqueous dispersion liquid, as compared with the opposite side, which was applied with the 0.01% α-lipoic acid-containing aqueous dispersion liquid or unapplied (FIG. 18). From the results shown above, it was confirmed that α-lipoic acid-$MgCO_3$ nanoparticles have an effect of improving human wrinkles.

Test Example 12

Test for Hyaluronic Acid Accumulation by α-Lipoic Acid-$MgCO_3$ Nanoparticles 3 ml of D-MEM medium (D-MEM medium supplemented with 10% FCS, 100 units/ml of penicillin, and 100 μg/ml of streptomycin, all at final concentrations) was added to a plastic petri dish having a diameter of 6.0 cm. To this, $1.5 \times 10^5$ cells of 3T3-L1 cells, which are preadipocytes, were suspended, and precultured for 3 days to result in a confluent state. Thereafter, the medium was replaced with 3 ml of an adipocyte differentiation induction medium (D-MEM supplemented with 10% FCS, 100 units/ml of penicillin, 100 µg/ml of streptomycin, 5 µg/ml of insulin, 0.25 µM of dexamethasone, and 0.5 mM of isobutyl-methylxanthine, all at final concentrations). After another 2 days, the medium was replaced with 3 ml of the adipocyte differentiation induction medium of the same composition, and then the culturing was carried out for 2 days. Thus, the culturing in the adipocyte differentiation induction medium was carried out for 4 days in total. Either an α-lipoic acid solution or the α-lipoic acid-$MgCO_3$ nanoparticle solution of Example 50A was added to the adipocyte differentiation induction medium to result in 0, 100, 250 or 500 µg of α-lipoic acid concentration. After the culturing, 1 ml of a PBS buffer solution was added to the petri dish, from which the culture supernatant was removed, and the cells were harvested with a cell scraper. The cells thus harvested were disrupted by ultrasonication to result in a cell disrupted fluid. The amount of hyaluronic acid contained therein was quantified by an enzyme-linked immunosorbent assay (ELISA). The experimental method of hyaluronic acid ELISA was carried out according to the method described in Annica Jacobson, et al., Int. J. Cancer, 102:212-219 (2002). The culture was all carried out under the conditions of 5% $CO_2$ and 37° C.

Figure 19:
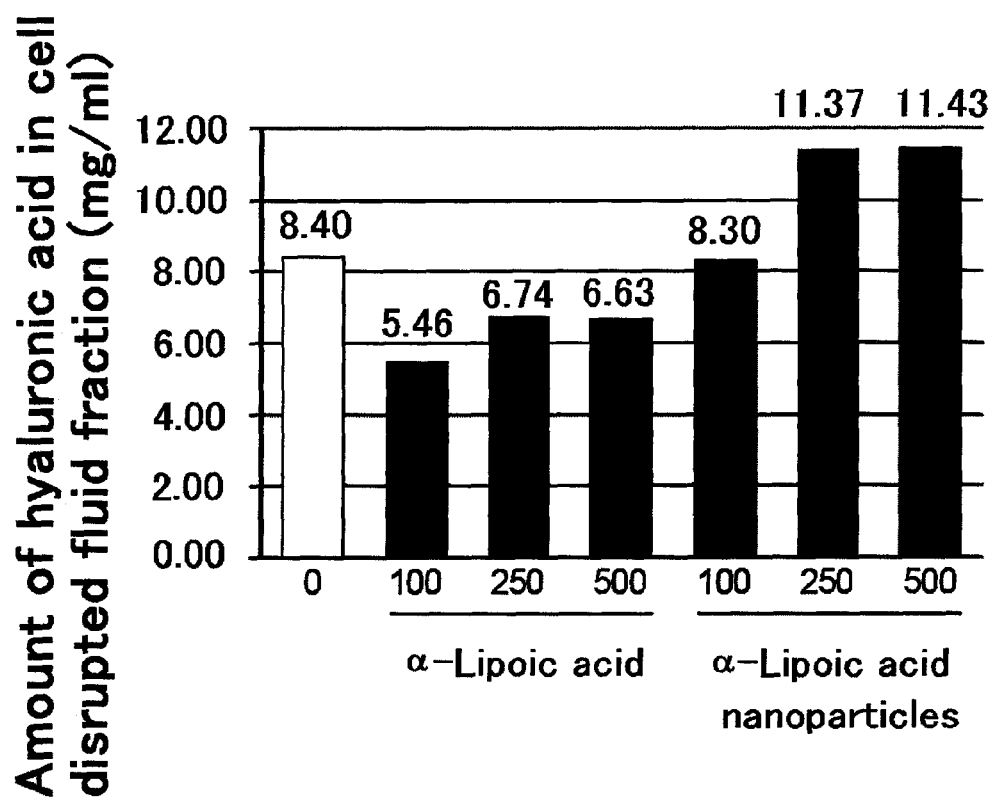
FIG. 19 shows the results of hyaluronic acid ELISA for the cell disrupted fluid fraction of Test Example 12.

As a result, the α-lipoic acid-$MgCO_3$ nanoparticle-added group showed a higher hyaluronic acid amount as compared with the α-lipoic acid-added group (FIG. 19). From the results shown above, it was confirmed that the α-lipoic acid-$MgCO_3$ nanoparticles have the action of causing hyaluronic acid to be accumulated on the cell surface. Accordingly, it was suggested that the α-lipoic acid-$MgCO_3$ nanoparticles improve wrinkles by enhancing the water retentivity of the dermal layer of the skin. Furthermore, an effect of reducing damages between joint cartilage tissues by accumulating and concentrating hyaluronic acid at the cartilage cell surfaces in joints, is expected, and thus the usefulness of the nanoparticles as a therapeutic drug for osteoarthritis was also suggested.

Example 51

Production of an Ointment for External Use

An ointment for external use is produced by mixing the materials of the formulation shown in Table 9 below according to a method conventionally carried out in the art.

TABLE 9

| Formulation of ointment for external use | |
|---|---|
| α-Lipoic acid-phosphate Ca nanoparticle paste of Example 7A | 5.0 |
| White petrolatum | 93.5 |
| Carboxymethylcellulose | 1.2 |
| Methylparaben | 0.3 |
| Total | 100.00 parts by weight |

Example 52

Production of a Cosmetic Emulsion

A cosmetic emulsion is produced by mixing the materials of the formulation shown in Table 10 below according to a method conventionally carried out in the art.

TABLE 10

| Formulation of a cosmetic emulsion | |
|---|---|
| α-Lipoic acid-$CaCO_3$ nanoparticle dispersion liquid of Example 14A | 0.10 |
| Cetyl alcohol | 1.5 |
| Petrolatum | 12.00 |
| Liquid paraffin | 8.00 |
| Polyoxyethylene (10) sorbitan monostearate | 10.00 |
| Polyethylene glycol (1500) | 3.00 |
| Triethanolamine | 1.00 |
| Tocopherol acetate | 0.30 |
| Sodium hydrogen sulfite | 0.01 |
| Carboxyvinyl polymer | 0.05 |
| Fragrance | Appropriate amount |
| Methylparaben | Appropriate amount |
| Water | Balance |
| Total | 100.00 parts by weight |

Example 53

Production of a Toothpaste

A toothpaste is produced by mixing the materials of the formulation shown in Table 11 below according to a method conventionally carried out in the art.

TABLE 11

| Formulation of a toothpaste | |
|---|---|
| α-Lipoic acid-$ZnCO_3$ nanoparticle dispersion liquid of Example 10B | 2.00 |
| Calcium hydrogen phosphate | 45.00 |
| Glycerin | 8.00 |
| Sorbitol | 20.00 |
| Carboxymethylcellulose sodium | 1.00 |
| Sodium lauryl sulfate | 1.50 |
| Saccharin sodium | 0.10 |
| Flavor | 1.00 |
| Sodium benzoate | 0.30 |
| Water | Balance |
| Total | 100.00 parts by weight |

Example 54

Production of a Tablet

A tablet is produced by mixing the materials of the formulation shown in Table 12 below according to a method conventionally carried out in the art.

TABLE 12

| Formulation of a tablet | |
|---|---|
| Polydextrose | 9.7 |
| Sugar ester | 2.0 |
| Flavor | 0.3 |
| Sorbitol | 27.0 |
| Palatinose | 60.0 |
| α-Lipoic acid-$CaCO_3$ nanoparticle paste of Example 1A | 1.0 |
| Total | 100.0 parts by weight |

Example 55

Production of an Injection Liquid

An injection liquid is produced by mixing the materials of the formulation shown in Table 13 below according to a method conventionally carried out in the art.

TABLE 13

| Formulation of an injection liquid | |
|---|---|
| Physiological saline of Japanese Pharmacopoeia | 95.0 |
| α-Lipoic acid-CaCO₃ nanoparticle paste of Example 5B | 5.0 |
| Total | 100.0 parts by weight |

Example 56

Production of a Skin Toner

A skin toner is produced by mixing the materials of the formulation shown in Table 14 below according to a method conventionally carried out in the art.

TABLE 14

| Formulation of a skin toner | |
|---|---|
| α-Lipoic acid-Ca nanoparticle dispersion liquid of Example 22A | 1.0 |
| 1,3-Butylene glycol | 1.0 |
| Polyethylene glycol 1000 | 1.0 |
| Glycerin | 1.0 |
| 1% Hyaluronic acid | 1.0 |
| Methylparaben | 0.1 |
| Water | 94.9 |
| Total | 100.0 parts by weight |

Example 57

Production of an External Lotion for Skin

A external lotion for skin is produced by mixing the materials of the formulation shown in Table 15 below according to a method conventionally carried out in the art.

TABLE 15

| Formulation of a lotion | |
|---|---|
| α-Lipoic acid-Ca nanoparticle dispersion liquid of Example 22B | 5.0 |
| Dipropylene glycol | 3.0 |
| Hydroxyethylcellulose | 0.2 |
| Xanthan gum | 0.1 |
| Glycerin | 2.0 |
| 1% Hyaluronic acid Na | 2.0 |
| Dextrin | 0.8 |
| Methylparaben | 0.2 |
| Water | 86.7 |
| Total | 100.00 parts by weight |

Test Example 13

Test for Verifying the Effect of α-Lipoic Acid Nanoparticle-Containing External Lotion for Skin, on the Decrease of Barrier Function of Hairless Mouse Skin Due to UV-B Irradiation The dorsal part of a hairless mouse (Hos: HR-1, 25 weeks old, male) was irradiated one time with UV-B at 70 mJ/cm². After the ultraviolet irradiation, the α-lipoic acid-CaCO₃ nanoparticle-containing external lotion for skin obtained in Example 57 was applied on this mouse using 100 μl per day, once a day, for consecutive 4 days. Transepidermal water loss (TEWL) was measured immediately before ultraviolet irradiation and on the 4th day and 5th day from the day of ultraviolet irradiation, and thereby the state of skin barrier function was checked. The amount of increase of the TEWL value from TEWL immediately before the ultraviolet irradiation to TEWL on each measurement day, was defined as ΔTEWL, and this was used as a criterion for a decrease in the skin barrier function.

As shown in Table 16, it was confirmed that for all of the measurement days, the group applied with the α-lipoic acid-CaCO₃ nanoparticle-containing external lotion for skin (n=3) was suppressed an increase in the TEWL value, that is, a decrease in the skin barrier function was suppressed, as compared with those for the control groups (applied similarly with only water that did not contain α-lipoic acid, n=3). From the results shown above, it was confirmed that the α-lipoic acid-CaCO₃ nanoparticle-containing external lotion for skin acts on the skin after ultraviolet irradiation, and exhibits an effect of reducing the functional disorder of the skin due to ultraviolet stimulation.

TABLE 16

| | | Time elapsed (days) | | |
|---|---|---|---|---|
| | | 0 | 3 | 4 |
| ΔTEWL (g·m²/h) average value | Group applied with distilled water | 0 | 63.2 | 165.4 |
| | Group applied with α-lipoic acid-CaCO₃ nanoparticle-containing external lotion for skin of Example 57 | 0 | 31.9 | 137.0 |

Example 58

Production of a Drink Preparation

A drink preparation was produced by mixing the materials of the formulation shown in Table 17 below according to a method conventionally carried out in the art.

TABLE 17

| Formulation of a drink preparation | |
|---|---|
| α-Lipoic acid-Ca nanoparticle dispersion liquid of Example 22B | 10.0 |
| Sucrose | 27.0 |
| Water | Balance |
| Total | 100.00 parts by weight |

A comparative article was produced by replacing the α-lipoic acid-Ca nanoparticle solution in the Table 17 described above, with a 1% aqueous solution obtained by neutralizing and dissolving α-lipoic acid using a minimal amount of 0.25M aqueous sodium hydroxide solution. 5 expert panelists performed an organoleptic evaluation of the drink preparation of Example 58 and the comparative article. As a result, all of the experts evaluated that the drink preparation of the present Example has a reduced sulfurous odor and a reduced tingling sensation of the tongue which are caused by α-lipoic acid, as compared with the comparative article, thus having excellent palatability.

Example 59

Production of a Refreshing Beverage

A refreshing beverage was produced by mixing the materials of the formulation shown in Table 18 below according to a method conventionally carried out in the art.

TABLE 18

| Formulation of a refreshing beverage | |
| --- | --- |
| α-Lipoic acid-Mg nanoparticle dispersion liquid of Example 29B | 10.0 |
| Sucrose | 9.0 |
| Citric acid | 1.4 |
| Malic acid | 0.5 |
| Water | Balance |
| Total | 100.00 parts by weight |

A comparative article was produced by replacing the α-lipoic acid-Mg nanoparticle solution in Table 18 described above, with a 1% aqueous solution obtained by neutralizing and dissolving α-lipoic acid using a minimal amount of 0.25 M aqueous solution of sodium hydroxide. 5 expert panelists performed an organoleptic evaluation of the refreshing beverage (drink preparation) of Example 59 and the comparative article. As a result, all of the panelists evaluated that the refreshing beverage (drink preparation) of the present Example has a reduced sulfurous odor and a reduced tingling sensation at the tongue which are caused by α-lipoic acid, as compared with the comparative article, thus having excellent palatability.

As such, the present invention has been exemplified using preferred embodiments of the present invention, but the present invention should not be construed to be limited to these embodiments. It is understood that the scope of the present invention should be interpreted only by the claims. It is understood that a person skilled in the art will understand that from the descriptions of the specific preferred embodiments of the present invention, equivalent scope can be carried out based on the description of the present invention and common technical knowledge. It is understood that all patents, patent applications, and documents cited in this specification should be herein incorporated by reference for the content thereof to the same extent as if the contents themselves were specifically described in the present specification.

INDUSTRIAL APPLICABILITY

The subject nanoparticles maintain the form of a transparent solution when dissolved in water, and are less irritant since α-lipoic acid is coated with a coating of a polyvalent metal inorganic salt. Therefore, it is possible to administer such in the form of subcutaneously and intravenously injectable preparations.

When the subject nanoparticles are administered by applying in the form of an external preparation, or through the oral mucosa such as the gingiva in the form of a composition for oral cavity, the nanoparticles are satisfactorily transdermally absorbed, and do not cause inflammation since the nanoparticles are not irritant. α-Lipoic acid is released from the nanoparticles in a sustained release manner, and thus effects such as activation of the skin, suppression of photoaging, recovery from photoaging, and suppression of melanogenesis due to ultraviolet stimulation can be manifested.

When the subject nanoparticles are utilized in foods, since the sulfurous odor characteristic of α-lipoic acid is reduced, the value as an article of preference is enhanced, as well as the amount of formulation of α-lipoic acid can also be increased. Thus, a composition which may more easily exhibit the effectiveness of α-lipoic acid can be obtained. Furthermore, since the subject nanoparticles have a very large specific surface, they are very satisfactorily absorbed into the body. Moreover, since the subject nanoparticles are water-soluble, use in a wide variety of forms of foods such as beverages is made possible.

The invention claimed is:

1. α-Lipoic acid nanoparticles comprising α-lipoic acid, a nonionic surfactant, a divalent metal ion, and a carbonate ion or a phosphate ion, wherein the divalent metal ion is a calcium ion, a zinc ion or a magnesium ion, wherein mixed micelles of the α-lipoic acid and the nonionic surfactant are formed, and wherein a coating of a polyvalent metal inorganic salt is formed at the micelle surface.

2. The α-lipoic acid nanoparticles according to claim 1, wherein the nonionic surfactant is selected from the group consisting of polyoxyethylene hydrogenated castor oils, polyoxyethylene alkyl ethers, polyoxyethylene sorbitan fatty acid esters, polyoxyethylene polyoxypropylene alkyl ethers, sucrose fatty acid esters and polyglycerin fatty acid esters.

3. The α-lipoic acid nanoparticles according to claim 1, further comprising polyethylene glycol.

4. An external preparation for skin, comprising the α-lipoic acid nanoparticles according to claim 1.

5. A pharmaceutical product comprising the α-lipoic acid nanoparticles according to claim 1.

6. A composition for oral cavity, comprising the α-lipoic acid nanoparticles according to claim 1.

7. A food comprising the α-lipoic acid nanoparticles according to claim 1.

8. The α-lipoic acid nanoparticles according to claim 1, wherein the nanoparticles can be dispersed transparently in water.

9. α-Lipoic acid nanoparticles comprising:
   a mixed micelle of α-lipoic acid and a nonionic surfactant; and a coating of a polyvalent metal inorganic salt formed with a divalent metal ion, and a carbonate ion or a phosphate ion,
   wherein the divalent metal ion is a calcium ion, a zinc ion or a magnesium ion, wherein the coating of a polyvalent metal inorganic salt is formed at the micelle surface.

* * * * *